US010369198B2

(12) United States Patent
Wollert et al.

(10) Patent No.: US 10,369,198 B2
(45) Date of Patent: Aug. 6, 2019

(54) FACTOR 1 PROTEIN, FACTOR 2 PROTEIN AND INHIBITORS THEREOF FOR USE IN TREATING OR PREVENTING DISEASES

(71) Applicant: MEDIZINISCHE HOCHSCHULE HANNOVER, Hannover (DE)

(72) Inventors: Kai Christoph Wollert, Hannover (DE); Mortimer Korf-Klingebiel, Duderstadt (DE)

(73) Assignee: MEDIZINISCHE HOCHSCHULE HANNOVER, Hanover (DE)

( * ) Notice: Subject to any disclaimer, the term of this patent is extended or adjusted under 35 U.S.C. 154(b) by 0 days.

(21) Appl. No.: 14/759,852

(22) PCT Filed: Jan. 16, 2014

(86) PCT No.: PCT/EP2014/050788
§ 371 (c)(1),
(2) Date: Jul. 8, 2015

(87) PCT Pub. No.: WO2014/111458
PCT Pub. Date: Jul. 24, 2014

(65) Prior Publication Data
US 2015/0352186 A1 Dec. 10, 2015

(30) Foreign Application Priority Data

Jan. 17, 2013 (EP) .................................. 13151593

(51) Int. Cl.
| | |
|---|---|
| A61K 38/16 | (2006.01) |
| A61K 38/18 | (2006.01) |
| A61K 38/17 | (2006.01) |
| C07K 16/22 | (2006.01) |
| C07K 16/28 | (2006.01) |
| A61K 9/00 | (2006.01) |
| A61K 31/7088 | (2006.01) |

(52) U.S. Cl.
CPC ............ *A61K 38/18* (2013.01); *A61K 9/0019* (2013.01); *A61K 31/7088* (2013.01); *A61K 38/177* (2013.01); *A61K 38/1709* (2013.01); *C07K 16/22* (2013.01); *C07K 16/28* (2013.01); *C07K 2317/34* (2013.01); *C07K 2317/76* (2013.01); *C12N 2799/022* (2013.01)

(58) Field of Classification Search
None
See application file for complete search history.

(56) References Cited

U.S. PATENT DOCUMENTS

| | | |
|---|---|---|
| 8,486,438 B2 | 7/2013 | Mathiowitz et al. |
| 2003/0166547 A1 | 9/2003 | Oliviero |
| 2004/0185049 A1 | 9/2004 | Hunter et al. |
| 2004/0214229 A1 | 10/2004 | Bergamnn et al. |
| 2007/0160985 A1 | 7/2007 | Gallaher et al. |
| 2008/0004232 A1 | 1/2008 | Wilkins et al. |

FOREIGN PATENT DOCUMENTS

| | | |
|---|---|---|
| EP | 2 130 547 A | 12/2009 |
| WO | 1998/011217 A2 | 3/1998 |

OTHER PUBLICATIONS

The International Search Report for PCT/EP2014/05788 dated Apr. 14, 2014, pp. 1-8.
Database WPI, Week 200308 Thomson Scientific, London AN2003-092937—XP002697500.
Database WPI, Week 201265 Thomson Scientific, London an 2012-L82618—XP002697501.
Meg, Q. et al. "IL-25 and its receptor (IL-25R) in allergic inflammation: its role in VEGF-mediated Angiogenesis" Journal of Allergy and Clinical Immunology (2009), vol. 123(2), p. S58.
Corrigan, C.J. et al. "T-helper cell type 2 (TH2) memory T cell-potentiating cytokine IL-25 has the potential to promote angiogenesis in asthma" Proceedings of the National Academy of Sciences (2001), vol. 108(4), pp. 1579-1584.
Office Action in corresponding JP case, dated Dec. 12, 2017.
Sunagozaka, et al., "Indentification of a secretory protein c19orf10 activated in heptocellular carcinoma,"Int. J. Cancer, 2011, vol. 129, pp. 1576-1585.

*Primary Examiner* — Christine J Saoud
*Assistant Examiner* — Jon M Lockard
(74) *Attorney, Agent, or Firm* — McDonnell Boehnen Hulbert & Berghoff LLP

(57) ABSTRACT

The present invention relates to proteins comprising amino acid sequences encoded by nucleic acids derived from the human chromosomal region C19Orf10 termed Factor1 and/or C19Orf63 termed Factor 2 for the use in enhancing proliferation and/or healing and/or inhibiting apoptosis of none-transformed tissue or none-transformed cell or inhibitors thereof. The invention further relates to the use of inhibitors of factor1 and factor 2 for medical use, preferably for use in treating or preventing a disease in which angiogenesis contributes to disease development or progression.

9 Claims, 12 Drawing Sheets
Specification includes a Sequence Listing.

Figure 6

```
CLUSTAL 2.1 multiple sequence alignment

SEQ_ID_NO_2      MAAPSGGWNG-VGASLWAALLLGAVALRPAEAVSEPTTVAFDVRPGGVVHSFSHNVGPGD 59
SEQ_ID_NO_12     MAAPSGGWNG-VGASLWAALLLGAVALSPAEAVSEPTTVAFDVRPGGVVHSFSHNVGPGD 59
SEQ_ID_NO_14     MAAPSGRRNGSGGANLWVSLLLAAAALRPVETVSEPTTVAFDVRPGGVVHSFSQNVGPGD 60
SEQ_ID_NO_17     MAAPSERRNG-GGASLWAALLLAAAALRPAEAVSEPTTVAFDVRPGGVVHSFSQNVGPGD 59
SEQ_ID_NO_15     MAAPRGRRNGSAGASMWGALLLAAVALRSVEAVSEPTTVAFDVRPGGVVHSFSHSAGPGD 60
SEQ_ID_NO_16     MAAPRGNSDG-CGGAWFAALLLAAVALRPAEAVSEPTTVAFDVRPGGVVHSFSQNVGPGD 59
SEQ_ID_NO_13     MAAPS--------GGFWTAVVLAAAALKLAAAVSEPTTVPFDVRPGGVVHSFSQDVGPGN 52
SEQ_ID_NO_18     MAAPCGRSSR----WLWAAVVPAAVLCLAVRAAEEASTAEFDVRPGGEVHFFSRSLG--- 53
SEQ_ID_NO_20     MATYG---------IICAFLLLAVCS----AQEKSSTEEFDVRPGGLQHSFTSKLG--- 44
SEQ_ID_NO_19     MARQSNTCAG--NLAFLFALALIAARVPAEASEEQAKTVEFNVKPGGVVHTFSEGIG--- 55
                 **              :    *.       :  :..*  *:*:***   * *:    *

SEQ_ID_NO_2      KYTCMFTYASQGGTNEQWQMSLGTSEDHQHFTCTIWRPQGKSYLYFTQFKAEVRGAEIEY 119
SEQ_ID_NO_12     KYTCMFTYASQGGTNEQWQMSLGTSEDHQHFTCTIWRPQGKSYLYFTQFKAEVRGAEIEY 119
SEQ_ID_NO_14     KYTCVFTYASQGGTNEKWQMSLGTSEDHQHFTCTIWRPQGKSYLYFTQFKAEVRGAEIEY 120
SEQ_ID_NO_17     KYTCAFTYASQGGTNEKWQMSLGISEDHQHFTCTIWRPQGKSYLYFTQFRAEVRGAEIEY 119
SEQ_ID_NO_15     RFTCTFTYASQGGTNEQWQMSLGTSEDHQHFTCTIWRPQGKSYLYFTQFKAEVRGAQIEY 120
SEQ_ID_NO_16     KFTCTFTYASQGGTNEQWQMSLGTSEDHQHFTCIIWRPQGKSYLYFTQFKAEVHGAEIEY 119
SEQ_ID_NO_13     KFTCTFTYASQGGTNEQWQMSLGTSEDSQHFTCTIWRPQGKSYLYFTQFKAELRGAEIEY 112
SEQ_ID_NO_18     DYTCTFTYSAQGGTNEQWQMNIGVSEDNLLFSCSVWRPQGKSYLFFTQFKAEVKGAKIEY 113
SEQ_ID_NO_20     DYACTFTYAAQGGTNEKWHMSVGLSDDNQHFSCSIWRPQGKSYLFFTGFKAEVTGGKIEF 104
SEQ_ID_NO_19     EYECSFTYASQGGTNEQWLMSVGLTDDNRLFSCSVWRPQGKSYLFFTQFKAELKGTKIEY 115
                  : * ***::******:* *.:*  ::*   *:*  :**********:**  *:**:

SEQ_ID_NO_2      AMAYSKAAFERESDVPLKTEEFEVTKTAVAHRPGAFKAELSKLVIVAKASRTEL 173
SEQ_ID_NO_12     AMAYSKAAFERESDVPLKTEEFEVTKTAVAHRPGAFKAELSKLVIVAKASRTEL 173
SEQ_ID_NO_14     GMAYSKAAFEKESDVPLKNEEFEVTKTAVFHRPGAFKAELSKLVIVAKATRSEL 174
SEQ_ID_NO_17     GMAYSKAAFERESDVPLKSEEFEVTKTAVSHRPGAFKAELSKLVIVAKASRSEL 173
SEQ_ID_NO_15     GMAYSKAASERESDVPLKNEEFEVTKTTVAHRPGAFKAELSKLVIVAKASHSEL 174
SEQ_ID_NO_16     AMAYSKAAFERESDVPLKNEEFEVTKAAVAHRPGAFRAELSKLVIVAKEAHSEL 173
SEQ_ID_NO_13     AMAYSKAAFERESDVPLKSEEFEVTKTAVSHRPGAFKAELSKLVIVAKAARSEL 166
SEQ_ID_NO_18     AMAYSQAAVGAQSDIPLKQEEFEITETTVSHREGKFRFELSKLMIVAKTPHDEL 167
SEQ_ID_NO_20     SEAYSQASSDGSSDVKLKSSEYDVTDNVVSHRPGSFSSSLCKLVLVARSEHDEL 158
SEQ_ID_NO_19     ANAYSQSAAGGQSDVPLKPEEFTIGESTVTHKDGKFSAQLSKLTVIGRTQKDEL 169
                 . ***::.   .**: **  .*: :  ..* *:  * *  .*.** ::.: : **
```

Figure 7

```
CLUSTAL 2.1 multiple sequence alignment

SEQ_ID_NO_2         MAAPSGGWNG-VGASLWAALLLGAVALRPAEAVSEPTTVAFDVRPGGVVHSFSHNVGPGD 59
SEQ_ID_NO_12        MAAPSGGWNG-VGASLWAALLLGAVALSPAEAVSEPTTVAFDVRPGGVVHSFSHNVGPGD 59
SEQ_ID_NO_15        MAAPRGRRNGSAGASMWGALLLAAVALRSVEAVSEPTTVAFDVRPGGVVHSFSHSAGPGD 60
SEQ_ID_NO_16        MAAPRGNSDG-CGGAWFAALLLAAVALRPAEAVSEPTTVAFDVRPGGVVHSFSQNVGPGD 59
SEQ_ID_NO_14        MAAPSGRRNGSGGANLWVSLLLAAAALRPVETVSEPTTVAFDVRPGGVVHSFSQNVGPGD 60
SEQ_ID_NO_17        MAAPSERRNG-GGASLWAALLLAAAALRPAEAVSEPTTVAFDVRPGGVVHSFSQNVGPGD 59
SEQ_ID_NO_13        MAAPS--------GGFWTAVVLAAAALKLAAAVSEPTTVPFDVRPGGVVHSFSQDVGPGN 52
                    ****         .  : :::*.*.**  . :*******.**************:..***:

SEQ_ID_NO_2         KYTCMFTYASQGGTNEQWQMSLGTSEDHQHFTCTIWRPQGKSYLYFTQFKAEVRGAEIEY 119
SEQ_ID_NO_12        KYTCMFTYASQGGTNEQWQMSLGTSEDHQHFTCTIWRPQGKSYLYFTQFKAEVRGAEIEY 119
SEQ_ID_NO_15        RFTCTFTYASQGGTNEQWQMSLGTSEDHQHFTCTIWRPQGKSYLYFTQFKAEVRGAQIEY 120
SEQ_ID_NO_16        KFTCTFTYASQGGTNEQWQMSLGTSEDHQHFTCIIWRPQGKSYLYFTQFKAEVHGAEIEY 119
SEQ_ID_NO_14        KYTCVFTYASQGGTNEKWQMSLGTSEDHQHFTCTIWRPQGKSYLYFTQFKAEVRGAEIEY 120
SEQ_ID_NO_17        KYTCAFTYASQGGTNEKWQMSLGISEDHQHFTCTIWRPQGKSYLYFTQFRAEVRGAEIEY 119
SEQ_ID_NO_13        KFTCTFTYASQGGTNEQWQMSLGTSEDSQHFTCTIWRPQGKSYLYFTQFKAELRGAEIEY 112
                    ::**  ************:****** ***  ***** ******************:**::**:***

SEQ_ID_NO_2         AMAYSKAAFERESDVPLKTEEFEVTKTAVAHRPGAFKAELSKLVIVAKASRTEL 173
SEQ_ID_NO_12        AMAYSKAAFERESDVPLKTEEFEVTKTAVAHRPGAFKAELSKLVIVAKASRTEL 173
SEQ_ID_NO_15        GMAYSKAASERESDVPLKNEEFEVTKTTVAHRPGAFKAELSKLVIVAKASHSEL 174
SEQ_ID_NO_16        AMAYSKAAFERESDVPLKNEEFEVTKAAVAHRPGAFRAELSKLVIVAKEAHSEL 173
SEQ_ID_NO_14        GMAYSKAAFEKESDVPLKNEEFEVTKTAVFHRPGAFKAELSKLVIVAKATRSEL 174
SEQ_ID_NO_17        GMAYSKAAFERESDVPLKSEEFEVTKTAVSHRPGAFKAELSKLVIVAKASRSEL 173
SEQ_ID_NO_13        AMAYSKAAFERESDVPLKSEEFEVTKTAVSHRPGAFKAELSKLVIVAKAARSEL 166
                    .****** *:*******.*******::* ******:************ :::**
```

Figure 8

```
CLUSTAL 2.1 multiple sequence alignment

SEQ_ID_NO_4         ----MAAASAGAT-RLLLLLLMAVAAPSRARGSGCRAGTGARGAGAEGREGEACGTVGLL  55
SEQ_ID_NO_21        ----MAATSGGAT-RLLLLLLMAVAAPSRARGSGCRAGTGARGAGAEGREGEACGTVGLL  55
SEQ_ID_NO_25        ----MAAAGAGAT-RLLLLLLMAAAAPSRARGSGCRPGTAARGAGAEGREGEGCGPVGLL  55
SEQ_ID_NO_23        ----MAAAGAVVT-RLFLLLLMAAAAPSRARGSGCRSGAALRGAGAEGRESEGCGTVGLL  55
SEQ_ID_NO_22        ----MAAAGAGAP-RLLLLLLIVAAAPSRARGSSCRAGAATRGVGAEGREGESCGTVGLL  55
SEQ_ID_NO_24        ----MVAAGAGVT-RLLVLLLMVAAAPSRARGSGCRVGASARGTGADGREAEGCGTVALL  55
SEQ_ID_NO_26        GGQRAGPLSSIVTGNCWVWLIALPFLAVTAQGSVCRLKTG------DGRESESCGTN-LE  53
SEQ_ID_NO_27        -----MAPIRVLS---LVLPILSTVPLLLTQFGECNNGRRS----GDAVDTDFSGFS-VP  47
                         .     .    : :         :: . *.        :. : : .*   :

SEQ_ID_NO_4         LEHSFEIDDSANFRKRGSLLWN-QQDGTLSLSQRQLSEEERGRLRDVAALNGLYRVRIPR 114
SEQ_ID_NO_21        LEHSFEIDDSANFRKRGSLLWN-QQDGTLSLSQRQLSEEERGRLRDVAALNGLYRVRVPR 114
SEQ_ID_NO_25        LEHSFEIDDNAHFRKRGSLLWN-QQDGTLSLSQRQLSEEERGRLRDVAALNGLYRVRVPR 114
SEQ_ID_NO_23        LEHSFEIDDSAHFRKRGSLLWN-QQDGTLSLSQRQLNEEERGRLRDVAALNGLYRVRVPQ 114
SEQ_ID_NO_22        LEHSFEIDDTAQFRKRGSLLWN-QQDGTLSLSQRQLNEEERGRLRDVAALNGLYRVRVPR 114
SEQ_ID_NO_24        LEHSFELGDGANFQKRGLLLWN-QQDGTLSATQRQLSEEERGRLRDVAAVNGLYRVRVPR 114
SEQ_ID_NO_26        LEHSFELDDSIHFTKRGSLFWSGTAEQSISILQKQLTEDERNKLRDIANLNGLYRIRIPR 113
SEQ_ID_NO_27        LEHSFEVDDVPRFRLRGALQFRGGRENSVYLSQNQLSEKDRNTLKDVAAVDGLYRIRVPR 107
                    ******:.*  .*  ** * :     : ::    *.**.*.:*. *:*:* ::****:*:*:

SEQ_ID_NO_4         R---PGALDGLEAGGYVSSFVPACSLVESHLSDQLTLHVDVAGNVVGVSVVTHPGGCRGH 171
SEQ_ID_NO_21        R---PGALDGLEASGYVSSFVPACSLVESHLSDQLTLHVDVAGNVVGVSVVTHPGGCRGH 171
SEQ_ID_NO_25        R---PGTPDGLEAGGYVSSFVPACSLVESHLSDQLTLHVDVAGNVVGVSVVTHPGGCRGH 171
SEQ_ID_NO_23        R---PGVPDGAEAGGYVSSFVPACSLVESHLSDQLTLHVDVAGNVVGVSVVTHPGGCRGH 171
SEQ_ID_NO_22        R---PGALDSAEAGGYVSSFVPACSLVESHLSDQLTLHVDVAGNVVGVSVVTYPGGCRGH 171
SEQ_ID_NO_24        R---PGTLDGSEAGGHVSSFVPACSLVESHLSDQLTLHVDVAGNVVGLSVVVYPGGCRGS 171
SEQ_ID_NO_26        K---LGITE--EANEYVTSFVRACSMVESHLSDEITVHTDLSGNVIGVSIVTFPGSCNGA 168
SEQ_ID_NO_27        VSLQVDRQTERQYEGYLTAFVRACALVESHLSDVITLHTDVSGYVIGISIVTIPGSCRGI 167
                         .    :    :::::** **::******* :*:*.*::* *:*:*:*. **.*.*

SEQ_ID_NO_4         EVED-VDLELFNTSVQLQPPTTAPGPETAAFIERLEMEQAQKAKNPQEQKSFFAKYWHII 230
SEQ_ID_NO_21        EVED-VDLELFNTSVQLQPPATAPGPETAAFIERLEMEQAQKAKNPQEQKSFFAKYWHII 230
SEQ_ID_NO_25        EVED-VDLELFNTSVQLQPPVTAPGPETAAFIERLEMEQAQKAKNPQEQKSFFAKYWHLI 230
SEQ_ID_NO_23        EVED-VDLELFNTSVHLQPPATAPGPETAAFIERLEMEQAQKAKNPQEQKSFFAKYWHLV 230
SEQ_ID_NO_22        EVED-VDLELFNTSVRLRPPGTAPGPETAAFIERLEMEQAQKAKNPQEQKSFFAKYWHLI 230
SEQ_ID_NO_24        EVED-EDLELFNTSVQLRPPSTAPGPETAAFIERLEMEQAQKAKNPQEQKSFFAKYWHLI 230
SEQ_ID_NO_26        EVED-VDLEMFNTTVHMQQPIPAAVPETAAFIERLEMEQAQKAKNPQEQKSFFAKYWMYI 227
SEQ_ID_NO_27        EVEDEVDLEVFNTTISVMAPVTAPVPETAPYIERMEMEMEKKGKNPQEQKSFFAKYWYLI 227
                    ****  ***:***:: :   * .*. ****.:***:***   :*.************** :

SEQ_ID_NO_4         LGGAVLLTALRPAAPGPAPPPQEA------- 254
SEQ_ID_NO_21        LGGAVLLTALRPAAPGPAPPPQEA------- 254
SEQ_ID_NO_25        LGGAVLLTALRPAAPGPAPPPQEA------- 254
SEQ_ID_NO_23        LGGAVLLTALRPAAPGPTPPPQEA------- 254
SEQ_ID_NO_22        LGGAVLLTALRPAAPGPTPPPQEA------- 254
SEQ_ID_NO_24        LGGAVLLTALRPAAPGPAPAPTEA------- 254
SEQ_ID_NO_26        IPVVLFLMMSGASDAGNQGGNGGGGGGGGGR 258
SEQ_ID_NO_27        LGGAVFLMATSSAQTPPGGAREQS------- 251
                    :  .::*    .: .         
```

Figure 9

CLUSTAL 2.1 multiple sequence alignment

```
SEQ_ID_NO_4      MAAASAGATRLLLLLLMAVAAPSRARGSGCRAGTGARGAGAEGREGEACGTVGLLLEHSF 60
SEQ_ID_NO_21     MAATSGGATRLLLLLLMAVAAPSRARGSGCRAGTGARGAGAEGREGEACGTVGLLLEHSF 60
SEQ_ID_NO_25     MAAAGAGATRLLLLLLMAAAAPSRARGSGCRPGTAARGAGAEGREGEGCGPVGLLLEHSF 60
SEQ_ID_NO_23     MAAAGAVVTRLFLLLLMAAAAPSRARGSGCRSGAALRGAGAEGRESEGCGTVGLLLEHSF 60
SEQ_ID_NO_22     MAAAGAGAPRLLLLLLIVAAAPSRARGSSCRAGAATRGVGAEGREGESCGTVGLLLEHSF 60
SEQ_ID_NO_24     MVAAGAGVTRLLVLLLMVAAAPSRARGSGCRVGASARGTGADGREAEGCGTVALLLEHSF 60
                 *.*:..  ..**::***:..*********.**  *:.  **.**:***.*.**.*.*******

SEQ_ID_NO_4      EIDDSANFRKRGSLLWNQQDGTLSLSQRQLSEEERGRLRDVAALNGLYRVRIPRRPGALD 120
SEQ_ID_NO_21     EIDDSANFRKRGSLLWNQQDGTLSLSQRQLSEEERGRLRDVAALNGLYRVRVPRRPGALD 120
SEQ_ID_NO_25     EIDDNAHFRKRGSLLWNQQDGTLSLSQRQLSEEERGRLRDVAALNGLYRVRVPRRPGTPD 120
SEQ_ID_NO_23     EIDDSAHFRKRGSLLWNQQDGTLSLSQRQLNEEERGRLRDVAALNGLYRVRVPQRPGVPD 120
SEQ_ID_NO_22     EIDDTAQFRKRGSLLWNQQDGTLSLSQRQLNEEERGRLRDVAALNGLYRVRVPRRPGALD 120
SEQ_ID_NO_24     ELGDGANFQKRGLLLWNQQDGTLSATQRQLSEEERGRLRDVAAVNGLYRVRVPRRPGTLD 120
                 *:.*  *:*:***  ***********  :****.************:*******:*:***.  *

SEQ_ID_NO_4      GLEAGGYVSSFVPACSLVESHLSDQLTLHVDVAGNVVGVSVVTHPGGCRGHEVEDVDLEL 180
SEQ_ID_NO_21     GLEASGYVSSFVPACSLVESHLSDQLTLHVDVAGNVVGVSVVTHPGGCRGHEVEDVDLEL 180
SEQ_ID_NO_25     GLEAGGYVSSFVPACSLVESHLSDQLTLHVDVAGNVVGVSVVTHPGGCRGHEVEDVDLEL 180
SEQ_ID_NO_23     GAEAGGYVSSFVPACSLVESHLSDQLTLHVDVAGNVVGVSVVTHPGGCRGHEVEDVDLEL 180
SEQ_ID_NO_22     SAEAGGYVSSFVPACSLVESHLSDQLTLHVDVAGNVVGVSVVTYPGGCRGHEVEDVDLEL 180
SEQ_ID_NO_24     GSEAGGHVSSFVPACSLVESHLSDQLTLHVDVAGNVVGLSVVVYPGGCRGSEVEDEDLEL 180
                 .  **.*:****************************:***.:****** **** ****

SEQ_ID_NO_4      FNTSVQLQPPTTAPGPETAAFIERLEMEQAQKAKNPQEQKSFFAKYWHIILGGAVLLTAL 240
SEQ_ID_NO_21     FNTSVQLQPPATAPGPETAAFIERLEMEQAQKAKNPQEQKSFFAKYWHIILGGAVLLTAL 240
SEQ_ID_NO_25     FNTSVQLQPPVTAPGPETAAFIERLEMEQAQKAKNPQEQKSFFAKYWHLILGGAVLLTAL 240
SEQ_ID_NO_23     FNTSVHLQPPATAPGPETAAFIERLEMEQAQKAKNPQEQKSFFAKYWHLVLGGAVLLTAL 240
SEQ_ID_NO_22     FNTSVRLRPPGTAPGPETAAFIERLEMEQAQKAKNPQEQKSFFAKYWHLILGGAVLLTAL 240
SEQ_ID_NO_24     FNTSVQLRPPSTAPGPETAAFIERLEMEQAQKAKNPQEQKSFFAKYWHLILGGAVLLTAL 240
                 *****:*:** ******************************::**********

SEQ_ID_NO_4      RPAAPGPAPPPQEA 254
SEQ_ID_NO_21     RPAAPGPAPPPQEA 254
SEQ_ID_NO_25     RPAAPGPAPPPQEA 254
SEQ_ID_NO_23     RPAAPGPTPPPQEA 254
SEQ_ID_NO_22     RPAAPGPTPPPQEA 254
SEQ_ID_NO_24     RPAAPGPAPAPTEA 254
                 *******:*.* **
```

Figure 10

```
CLUSTAL 2.1 multiple sequence alignment

SEQ_ID_NO_5        --MAA-------ASAGATRL--LLLLLMAVAAPSRARGSGCRAGTGARGAGAEGREGEAC 49
SEQ_ID_NO_28       --MAA-------ASAGATRL--LLLLLMAVAAPSRARGSSCRAGTGARGAGAEGREGEAC 49
SEQ_ID_NO_31       --MAA-------AGAGATRL--LLLLLMAAAAPSRARGSSCRAGAATRGAGAEGRENEGC 49
SEQ_ID_NO_30       MVMAA-------SGASASRL--LLLLLIVAAAPSRARGSGCRAGAAARGVGAEGREGESC 51
SEQ_ID_NO_29       --MVA-------AGAGVTRL--LVLLLMVAAAPSRARGSGCRVGASARGTGADGREAEGC 49
SEQ_ID_NO_32       --MAAGCLVGQRAGPLSDKLSGYCWVLLPLLLVATAQASVCRLKTG------DGRDSESC 52
SEQ_ID_NO_33       --MAP-----------IRVLSLVLPILSTVPLLLTQFGECNNGRRS----GDAVDTDFS 42
                     *..            ::         ::       ::.*.           :.:: .

SEQ_ID_NO_5        GTVGLLLEHSFEIDDSANFRKRGSLLWN-QQDGTLSLSQRQLSEEERGRLRDVAALNGLY 108
SEQ_ID_NO_28       GTVGLLLEHSFEIDDSANFRKRGSLLWN-QQDGTLSLSQRQLSEEERGRLRDVAALNGLY 108
SEQ_ID_NO_31       GTVGLLLEHSFEIDDAMHFRKRGSLLWN-QQDGTLSLSQRQLSEEERGRLRDVAALNGLY 108
SEQ_ID_NO_30       GTVGLLLEHSFEIDDAAHFRKRGSLLWN-QQDGTLSPSQRQLSEEERGRLRDVAALNGLY 110
SEQ_ID_NO_29       GTVALLLEHSFELGDGANFQKRGSLLWN-QQDGTLSATQRQLSEEERGRLRDVAAVNGLY 108
SEQ_ID_NO_32       GTN-LELEHSFELDDSIHFKKRGSLIWSGTAEQSISILQKQLTEDERNKLRDIANLNGLY 111
SEQ_ID_NO_33       GFS-VPLEHSFEVDDVPRFRLRGALQFRGGRENSVYLSQNQLSEKDRNTLKDVAAVDGLY 101
                    *  : ******:.*  .*: **:*  :     : ::   *.**:*.:*. *:*:* ::***

SEQ_ID_NO_5        RVRIPRR---PGALDGLEAGGYVSSFVPACSLVESHLSDQLTLHVDVAGNVVGVSVVTHP 165
SEQ_ID_NO_28       RVRIPRR---PGALDGLEAGGYVSSFVPACSLVESHLSDQLTLHVDVAGNVVGVSVVTQP 165
SEQ_ID_NO_31       RVRVPRR---PGAPEGPEAGGYVSSFVPACSLVESHLSDQLTLHVDVVGNVVGVSVVTLP 165
SEQ_ID_NO_30       RVRVPRR---PGALDSSEAGGYVSSFVPACSLVESHLSDQLTLHVDVAGNVVGVSVVTDP 167
SEQ_ID_NO_29       RVRVPRR---PGTLDGSEAGGHVSSFVPACSLVESHLSDQLTLHVDVAGNVVGLSVVVYP 165
SEQ_ID_NO_32       RIRVPRK---LGITE--EANEYVTSFVRACSMVESHLSDQISVHTDISGNVVGISIVTFP 166
SEQ_ID_NO_33       RIRVPRVSLQVDRQTERQYEGYLTAFVRACALVESHLSDVITLHTDVSGYVIGISIVTIP 161
                   *:*:**    .       :   :::::** **::******* :::*.*: * *:*:*:*. *

SEQ_ID_NO_5        GGCRGHEVED-VDLELFNTSVQLQPPTTAPGPETAAFIERLEMEQAQKAKNPQEQKSFFA 224
SEQ_ID_NO_28       GGCRGHEVED-VDLELFTTSVQLQPPTTAPGPETAAFIERLEMEQAQKAKNPQEQKSFFA 224
SEQ_ID_NO_31       GGCRGYEVED-VDLELFNTTVQLQPPTTAPGPETAAFIERLEMEQAQKAKNPQEQKSFFA 224
SEQ_ID_NO_30       GGCRGHEVED-VDLELFNTSVQLQPPGTAPGPETAAFIERLEMEQAQKAKNPQEQKSFFA 226
SEQ_ID_NO_29       GGCRGSEVED-EDLELFNTSVQLRPPSTAPGPETAAFIERLEMEQAQKAKNPQEQKSFFA 224
SEQ_ID_NO_32       GSCNGAEVED-VDLEMFNTTVYIQQPIAAAVPETAAFIERLEMEQAQKAKNPQEQKSFFA 225
SEQ_ID_NO_33       GSCRGIEVEDEVDLEVFNTTISVMAPVTAPVPETAPYIERMEMEMEKKGKNPQEQKSFFA 221
                   *.*.* ****   ***:*.*::   *  :*.  ****.:***:***  :*.***********

SEQ_ID_NO_5        KYWMYIIPVVLFLMMSGAPDTGGQGGGGGGGGGGGSGR 262
SEQ_ID_NO_28       KYWMYIIPVVLFLMMSGAPDTGGQGGGGGGGGGGGSGR 262
SEQ_ID_NO_31       KYWMYIIPVVLFLMMSGAPDTGGQGGGGGGGGGGGSGR 262
SEQ_ID_NO_30       KYWMYIIPVVLFLMMSGAPDAGGQGGGGGGGR------ 258
SEQ_ID_NO_29       KYWMYIIPVVLFLMMSGAPDAGGQGGGGGGSSR----- 258
SEQ_ID_NO_32       KYWMYIIPVVLFLMMSGASDAGNQGGNGGGGGGSGGGR 263
SEQ_ID_NO_33       KYWYLILGGAVFLMATSSAQTP-PGGAREQS------- 251
                   ***  *:   .:***  :.:.::    **        .
```

Figure 11

CLUSTAL 2.1 multiple sequence alignment

```
SEQ_ID_NO_5     --MAAASAGATRLLLLLLMAVAAPSRARGSGCRAGTGARGAGAEGREGEACGTVGLLLEH 58
SEQ_ID_NO_28    --MAAASAGATRLLLLLLMAVAAPSRARGSSCRAGTGARGAGAEGREGEACGTVGLLLEH 58
SEQ_ID_NO_31    --MAAACAGATRLLLLLLMAAAAPSRARGSSCRAGAATRGAGAEGRENEGCGTVGLLLEH 58
SEQ_ID_NO_30    MVMAASGASASRLLLLLLIVAAAPSRARGSGCRAGAAARGVGAEGREGESCGTVGLLLEH 60
SEQ_ID_NO_29    --MVAAGAGVTRLLVLLLMVAAAPSRARGSGCRVGASARGTGADGREAEGCGTVALLLEH 58
                  *.*:..*..:***:***:..*********.**.*:..**.**:*** *.****.*****

SEQ_ID_NO_5     SFEIDDSANFRKRGSLLWNQQDGTLSLSQRQLSEEERGRLRDVAALNGLYRVRIPRRPGA 118
SEQ_ID_NO_28    SFEIDDSANFRKRGSLLWNQQDGTLSLSQRQLSEEERGRLRDVAALNGLYRVRIPRRPGA 118
SEQ_ID_NO_31    SFEIDDAMHFRKRGSLLWNQQDGTLSLSQRQLSEEERGRLRDVAALNGLYRVRVPRRPGA 118
SEQ_ID_NO_30    SFEIDDAAHFRKRGSLLWNQQDGTLSPSQRQLSEEERGRLRDVAALNGLYRVRVPRRPGA 120
SEQ_ID_NO_29    SFELGDGANFQKRGSLLWNQQDGTLSATQRQLSEEERGRLRDVAAVNGLYRVRVPRRPGT 118
                ***:.*. :*:****************:.******************:*******:*****:

SEQ_ID_NO_5     LDGLEAGGYVSSFVPACSLVESHLSDQLTLHVDVAGNVVGVSVVTHPGGCRGHEVEDVDL 178
SEQ_ID_NO_28    LDGLEAGGYVSSFVPACSLVESHLSDQLTLHVDVAGNVVGVSVVTQPGGCRGHEVEDVDL 178
SEQ_ID_NO_31    PEGPEAGGYVSSFVPACSLVESHLSDQLTLHVDVVGNVVGVSVVTLPGGCRGYEVEDVDL 178
SEQ_ID_NO_30    LDSSEAGGYVSSFVPACSLVESHLSDQLTLHVDVAGNVVGVSVVTDPGGCRGHEVEDVDL 180
SEQ_ID_NO_29    LDGSEAGGHVSSFVPACSLVESHLSDQLTLHVDVAGNVVGLSVVVYPGGCRGSEVEDEDL 178
                :. ****:**********************.*****:***.  ****** **** **

SEQ_ID_NO_5     ELFNTSVQLQPPTTAPGPETAAFIERLEMEQAQKAKNPQEQKSFFAKYWMYIIPVVLFLM 238
SEQ_ID_NO_28    ELFTTSVQLQPPTTAPGPETAAFIERLEMEQAQKAKNPQEQKSFFAKYWMYIIPVVLFLM 238
SEQ_ID_NO_31    ELFNTTVQLQPPTTAPGPETAAFIERLEMEQAQKAKNPQEQKSFFAKYWMYIIPVVLFLM 238
SEQ_ID_NO_30    ELFNTSVQLQPPGTAPGPETAAFIERLEMEQAQKAKNPQEQKSFFAKYWMYIIPVVLFLM 240
SEQ_ID_NO_29    ELFNTSVQLRPPSTAPGPETAAFIERLEMEQAQKAKNPQEQKSFFAKYWMYIIPVVLFLM 238
                ***.*:***:** ***********************************************

SEQ_ID_NO_5     MSGAPDTGGQGGGGGGGGGGGSGR 262
SEQ_ID_NO_28    MSGAPDTGGQGGGGGGGGGGGSGR 262
SEQ_ID_NO_31    MSGAPDTGGQGGGGGGGGGGGSGR 262
SEQ_ID_NO_30    MSGAPDAGGQGGGGGGGR------ 258
SEQ_ID_NO_29    MSGAPDAGGQGGGGGGGSSR---- 258
                ******:***********
```

Figure 12
A
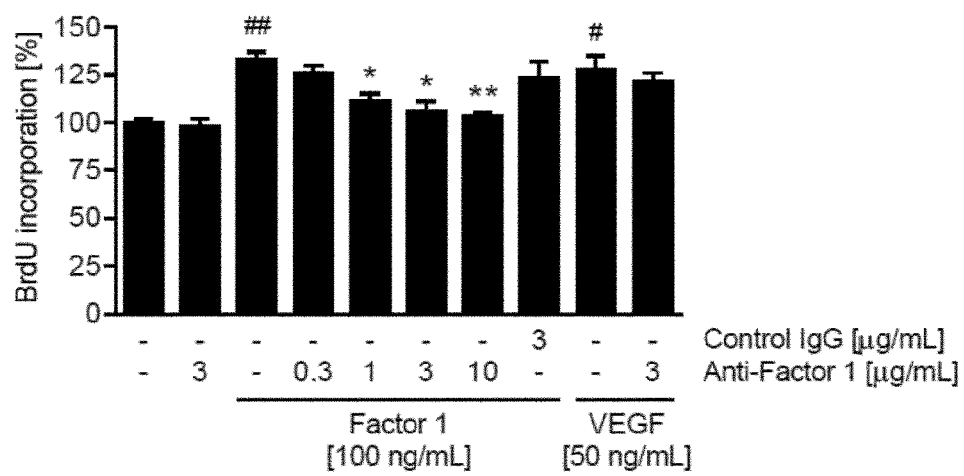
B
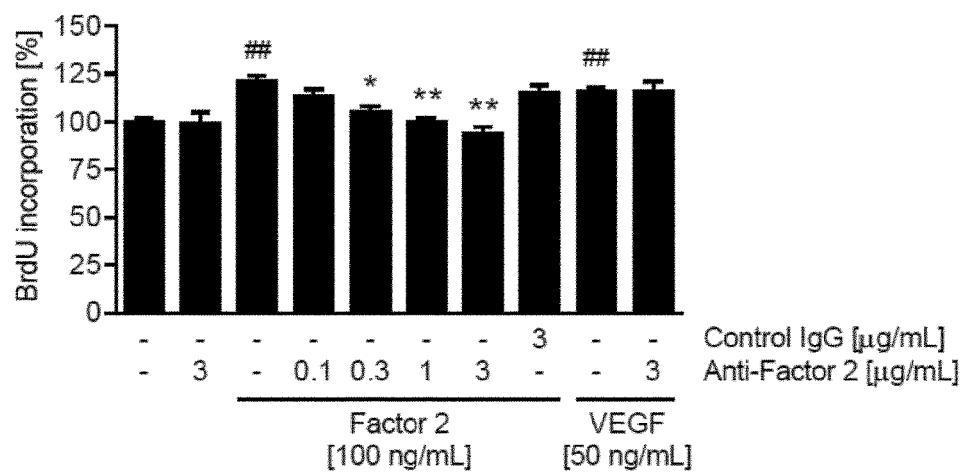

SEQUENCE LISTING

<160> NUMBER OF SEQ ID NOS: 39

<210> SEQ ID NO 1
<211> LENGTH: 142
<212> TYPE: PRT
<213> ORGANISM: Homo sapiens

<400> SEQUENCE: 1

Val Ser Glu Pro Thr Thr Val Ala Phe Asp Val Arg Pro Gly Gly Val
1               5                   10                  15

Val His Ser Phe Ser His Asn Val Gly Pro Gly Asp Lys Tyr Thr Cys
            20                  25                  30

Met Phe Thr Tyr Ala Ser Gln Gly Gly Thr Asn Glu Gln Trp Gln Met
        35                  40                  45

Ser Leu Gly Thr Ser Glu Asp His Gln His Phe Thr Cys Thr Ile Trp
    50                  55                  60

Arg Pro Gln Gly Lys Ser Tyr Leu Tyr Phe Thr Gln Phe Lys Ala Glu
65                  70                  75                  80

Val Arg Gly Ala Glu Ile Glu Tyr Ala Met Ala Tyr Ser Lys Ala Ala
                85                  90                  95

Phe Glu Arg Glu Ser Asp Val Pro Leu Lys Thr Glu Glu Phe Glu Val
            100                 105                 110

Thr Lys Thr Ala Val Ala His Arg Pro Gly Ala Phe Lys Ala Glu Leu
        115                 120                 125

Ser Lys Leu Val Ile Val Ala Lys Ala Ser Arg Thr Glu Leu
    130                 135                 140

<210> SEQ ID NO 2
<211> LENGTH: 173
<212> TYPE: PRT
<213> ORGANISM: Homo sapiens

<400> SEQUENCE: 2

Met Ala Ala Pro Ser Gly Gly Trp Asn Gly Val Gly Ala Ser Leu Trp
1               5                   10                  15

Ala Ala Leu Leu Leu Gly Ala Val Ala Leu Arg Pro Ala Glu Ala Val
            20                  25                  30

```
Ser Glu Pro Thr Thr Val Ala Phe Asp Val Arg Pro Gly Val Val
        35                  40                  45

His Ser Phe Ser His Asn Val Gly Pro Gly Asp Lys Tyr Thr Cys Met
 50                  55                  60

Phe Thr Tyr Ala Ser Gln Gly Gly Thr Asn Glu Gln Trp Gln Met Ser
 65                  70                  75                  80

Leu Gly Thr Ser Glu Asp His Gln His Phe Thr Cys Thr Ile Trp Arg
                 85                  90                  95

Pro Gln Gly Lys Ser Tyr Leu Tyr Phe Thr Gln Phe Lys Ala Glu Val
                100                 105                 110

Arg Gly Ala Glu Ile Glu Tyr Ala Met Ala Tyr Ser Lys Ala Ala Phe
            115                 120                 125

Glu Arg Glu Ser Asp Val Pro Leu Lys Thr Glu Glu Phe Glu Val Thr
        130                 135                 140

Lys Thr Ala Val Ala His Arg Pro Gly Ala Phe Lys Ala Glu Leu Ser
145                 150                 155                 160

Lys Leu Val Ile Val Ala Lys Ala Ser Arg Thr Glu Leu
                165                 170
```

```
<210> SEQ ID NO 3
<211> LENGTH: 200
<212> TYPE: PRT
<213> ORGANISM: Homo sapiens

<400> SEQUENCE: 3
```

```
Ser Gly Cys Arg Ala Gly Thr Gly Ala Arg Gly Ala Gly Ala Glu Gly
 1                5                  10                  15

Arg Glu Gly Glu Ala Cys Gly Thr Val Gly Leu Leu Leu Glu His Ser
            20                  25                  30

Phe Glu Ile Asp Asp Ser Ala Asn Phe Arg Lys Arg Gly Ser Leu Leu
        35                  40                  45

Trp Asn Gln Gln Asp Gly Thr Leu Ser Leu Ser Gln Arg Gln Leu Ser
 50                  55                  60

Glu Glu Glu Arg Gly Arg Leu Arg Asp Val Ala Ala Leu Asn Gly Leu
 65                  70                  75                  80

Tyr Arg Val Arg Ile Pro Arg Arg Pro Gly Ala Leu Asp Gly Leu Glu
                 85                  90                  95

Ala Gly Gly Tyr Val Ser Ser Phe Val Pro Ala Cys Ser Leu Val Glu
                100                 105                 110

Ser His Leu Ser Asp Gln Leu Thr Leu His Val Asp Val Ala Gly Asn
            115                 120                 125

Val Val Gly Val Ser Val Val Thr His Pro Gly Gly Cys Arg Gly His
130                 135                 140

Glu Val Glu Asp Val Asp Leu Glu Leu Phe Asn Thr Ser Val Gln Leu
145                 150                 155                 160

Gln Pro Pro Thr Thr Ala Pro Gly Pro Glu Thr Ala Ala Phe Ile Glu
                165                 170                 175

Arg Leu Glu Met Glu Gln Ala Gln Lys Ala Lys Asn Pro Gln Glu Gln
            180                 185                 190

Lys Ser Phe Phe Ala Lys Tyr Trp
        195                 200
```

```
<210> SEQ ID NO 4
<211> LENGTH: 254
<212> TYPE: PRT
<213> ORGANISM: Homo sapiens
```

```
<400> SEQUENCE: 4

Met Ala Ala Ala Ser Ala Gly Ala Thr Arg Leu Leu Leu Leu Leu
1               5                   10                  15

Met Ala Val Ala Ala Pro Ser Arg Ala Arg Gly Ser Gly Cys Arg Ala
            20                  25                  30

Gly Thr Gly Ala Arg Gly Ala Gly Ala Glu Gly Arg Glu Gly Glu Ala
            35                  40                  45

Cys Gly Thr Val Gly Leu Leu Leu Glu His Ser Phe Glu Ile Asp Asp
50                      55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
                85                  90                  95

Arg Leu Arg Asp Val Ala Ala Leu Asn Gly Leu Tyr Arg Val Arg Ile
                100                 105                 110

Pro Arg Arg Pro Gly Ala Leu Asp Gly Leu Glu Ala Gly Gly Tyr Val
            115                 120                 125

Ser Ser Phe Val Pro Ala Cys Ser Leu Val Glu Ser His Leu Ser Asp
130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Thr Thr
            180                 185                 190

Ala Pro Gly Pro Glu Thr Ala Ala Phe Ile Glu Arg Leu Glu Met Glu
            195                 200                 205

Gln Ala Gln Lys Ala Lys Asn Pro Gln Glu Gln Lys Ser Phe Phe Ala
210                 215                 220

Lys Tyr Trp His Ile Ile Leu Gly Gly Ala Val Leu Leu Thr Ala Leu
225                 230                 235                 240

Arg Pro Ala Ala Pro Gly Pro Ala Pro Pro Gln Glu Ala
                245                 250

<210> SEQ ID NO 5
<211> LENGTH: 262
<212> TYPE: PRT
<213> ORGANISM: Homo sapiens

<400> SEQUENCE: 5

Met Ala Ala Ala Ser Ala Gly Ala Thr Arg Leu Leu Leu Leu Leu
1               5                   10                  15

Met Ala Val Ala Ala Pro Ser Arg Ala Arg Gly Ser Gly Cys Arg Ala
            20                  25                  30

Gly Thr Gly Ala Arg Gly Ala Gly Ala Glu Gly Arg Glu Gly Glu Ala
            35                  40                  45

Cys Gly Thr Val Gly Leu Leu Leu Glu His Ser Phe Glu Ile Asp Asp
50                      55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
                85                  90                  95

Arg Leu Arg Asp Val Ala Ala Leu Asn Gly Leu Tyr Arg Val Arg Ile
                100                 105                 110
```

```
Pro Arg Arg Pro Gly Ala Leu Asp Gly Leu Glu Ala Gly Gly Tyr Val
        115                 120                 125

Ser Ser Phe Val Pro Ala Cys Ser Leu Val Glu Ser His Leu Ser Asp
    130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Thr Thr
                180                 185                 190

Ala Pro Gly Pro Glu Thr Ala Ala Phe Ile Glu Arg Leu Glu Met Glu
            195                 200                 205

Gln Ala Gln Lys Ala Lys Asn Pro Gln Glu Gln Lys Ser Phe Phe Ala
    210                 215                 220

Lys Tyr Trp Met Tyr Ile Ile Pro Val Val Leu Phe Leu Met Met Ser
225                 230                 235                 240

Gly Ala Pro Asp Thr Gly Gly Gln Gly Gly Gly Gly Gly Gly Gly Gly
                245                 250                 255

Gly Gly Gly Ser Gly Arg
            260

<210> SEQ ID NO 6
<211> LENGTH: 1067
<212> TYPE: DNA
<213> ORGANISM: Homo sapiens

<400> SEQUENCE: 6
ggcggacgct ccacgtgtcc ctcgccgcgc cccgtctacc cgcccctgcc ctgaggaccc      60
tagtccaaca tggcggcgcc cagcggaggg tggaacggcg tcggcgcgag cttgtgggcc     120
gcgctgctcc taggggccgt ggcgctgagg ccggcggagg cggtgtccga gcccacgacg     180
gtggcgtttg acgtgcggcc cggcggcgtc gtgcattcct tctcccataa cgtgggcccg     240
ggggacaaat atacgtgtat gttcacttac gcctctcaag gagggaccaa tgagcaatgg     300
cagatgagtc tggggaccag cgaagaccac cagcacttca cctgcaccat ctggaggccc     360
caggggaagt cctatctgta cttcacacag ttcaaggcag aggtgcgggg cgctgagatt     420
gagtacgcca tggcctactc taaagccgca tttgaaaggg aaagtgatgt ccctctgaaa     480
actgaggaat ttgaagtgac caaaacagca gtggctcaca ggcccggggc attcaaagct     540
gagctgtcca agctggtgat tgtggccaag gcatcgcgca ctgagctgtg accagcagcc     600
ctgttgcggg tggcaccttc tcatctccgg tgaagctgaa ggggcctgtg tccctgaaag     660
ggccagcaca tcactggttt tctaggaggg actcttaagt tttctacctg ggctgacgtt     720
gccttgtccg gaggggcttg cagggtggct gaagccctgg ggcagagaac agaggtccca     780
gggccctcct ggctcccaac agcttctcag ttcccacttc ctgctgagct cttctggact     840
caggatcgca gatccggggc acaaagaggg tggggaacat gggggctatg ctggggaaag     900
cagccatgct ccccccgacc tccagccgag catccttcat gagcctgcag aactgctttc     960
ctatgtttac ccaggggacc tcctttcaga tgaactggga agagatgaaa tgttttttca    1020
tatttaaata aataagaaca ttaaaaagca aaaaaaaaa  aaaaaaa                   1067

<210> SEQ ID NO 7
<211> LENGTH: 913
<212> TYPE: DNA
```

<213> ORGANISM: Mus musculus

<400> SEQUENCE: 7

| gagcgcctgc | gcattgcccc | ggaagcaaga | tggcagcccc | cagcggaggc | ttctggactg | 60 |
| cggtggtcct | ggcggccgca | gcgctgaaat | tggccgccgc | tgtgtccgag | cccaccaccg | 120 |
| tgccatttga | cgtgaggccc | ggaggggtcg | tgcattcgtt | ctcccaggac | gtaggacccg | 180 |
| ggaacaagtt | tacatgtaca | ttcacctacg | cttcccaagg | agggaccaac | gagcaatggc | 240 |
| agatgagcct | ggggacaagt | gaagacagcc | agcactttac | ctgtaccatc | tggaggcccc | 300 |
| aggggaaatc | ctacctctac | ttcacacagt | tcaaggctga | gttgcgaggt | gctgagatcg | 360 |
| agtatgccat | ggcctactcc | aaagccgcat | ttgagagaga | gagtgatgtc | ccctgaaaa | 420 |
| gtgaggagtt | tgaagtgacc | aagacagcag | tgtctcacag | gcctgggcc | ttcaaagctg | 480 |
| agctctccaa | gctggtgatc | gtagccaagg | cggcacgctc | ggagctgtga | ccctcgcctg | 540 |
| tcaagggcct | tcatgtccac | gttcctcagg | cacactgacc | gggactactt | gtctagggca | 600 |
| ctggttccca | taggagctgc | cctgccctgc | acaggtcaca | ctgtgtcact | ccgcagaact | 660 |
| ctctgagccc | ggtcacctgt | tttgccaggg | aagatgcagg | gcatgtgcgg | gggtgggatg | 720 |
| gaaggacttc | ctggctttcc | tgaagtcaag | atgtggtgtg | gtttcccctc | tgagccacag | 780 |
| atgagtgtcc | ccatcccagg | accactttct | aaccccatcc | agggcagctc | cactcagaag | 840 |
| gatgggaaag | gatagaaaaa | ataaataaat | aagtagccac | cttagtggtg | gctctgtggg | 900 |
| gtcaggactc | aga | | | | | 913 |

<210> SEQ ID NO 8
<211> LENGTH: 2048
<212> TYPE: DNA
<213> ORGANISM: Homo sapiens

<400> SEQUENCE: 8

| ttcctcccgg | cgtgctccgc | ggctcttggc | tcacagccgt | cccttcgctg | gtgggaagaa | 60 |
| gccgagatgg | cggcagccag | cgctggggca | accggctgc | tcctgctctt | gctgatggcg | 120 |
| gtagcagcgc | ccagtcgagc | ccggggcagc | ggctgccggg | ccgggactgg | tgcgcgaggg | 180 |
| gctggggcgg | aaggtcgaga | gggcgaggcc | tgtggcacgg | tggggctgct | gctggagcac | 240 |
| tcatttgaga | tcgatgacag | tgccaacttc | cggaagcggg | gctcactgct | ctggaaccag | 300 |
| caggatggta | ccttgtccct | gtcacagcgg | cagctcagcg | aggaggagcg | gggccgactc | 360 |
| cgggatgtgg | cagccctgaa | tggcctgtac | cgggtccgga | tcccaaggcg | acccggggcc | 420 |
| ctggatggcc | tggaagctgg | tggctatgtc | tcctcctttg | tccctgcgtg | ctccctggtg | 480 |
| gagtcgcacc | tgtcggacca | gctgaccctg | cacgtggatg | tggccggcaa | cgtggtgggc | 540 |
| gtgtcggtgg | tgacgcaccc | cggggctgc | cggggccatg | aggtggagga | cgtggacctg | 600 |
| gagctgttca | acacctcggt | gcagctgcag | ccgcccacca | cagccccagg | ccctgagacg | 660 |
| gcggccttca | ttgagcgcct | ggagatggaa | caggcccaga | aggccaagaa | ccccccaggag | 720 |
| cagaagtcct | tcttcgccaa | atactggcac | atcatcctgg | ggggggccgt | gttgctcaca | 780 |
| gccctgcgtc | ctgctgcgcc | agggcccgcg | ccaccgccac | aggaggcctg | atggatgtac | 840 |
| atcattcccg | tcgtcctgtt | cctcatgatg | tcaggagcgc | cagacaccgg | gggccagggt | 900 |
| gggggtgggg | gtgggggtgg | tggtgggggt | agtggccggt | gagggcccag | gctggtcagc | 960 |
| gtcccgtctt | gcacacccag | gggcctccct | ttctgctgga | gtccctgtg | tcctcagcca | 1020 |
| tcccaagaag | ggtttgctgg | tccctccttt | ccccccgtcc | cacgaggcca | cctgggccag | 1080 |

```
cccccttgtcc tctgccttct gctggcagag gagcagctgg actggggcct ttggcacagc    1140
agccggtgtc tcctgcgccc gcctccccca tggccccatg cagccccagg ggcttccccc    1200
ctgcccatgg agtagagccc gagatcctgg ccactatgcc agttctgacc tcgcatcccc    1260
ctaccccgag cccatgcagt ctgggaacat gccgccttct ctccagcctc tgtgcctttg    1320
ttccaggtgg tctcaccctc ctgtccctgg ctgggctagg tggtcctgtc caggctcctg    1380
cagcgccccc ctcactttga cactggacta ggatgcagcc tcccttctgt gtccccttga    1440
gggtaccctg gtcccctca tcaggggcag aggcatgaaa gagtcggggc tggatggccg    1500
ggggcttctg ggcccgacgc ctagtgcagc ccctgggggtc gtggtttgac atttgtctgc    1560
ctggtgcaaa caaggaatcc ttgcctttaa ggtgacaggc cctccacagg cttccagact    1620
tgaaggaaaa ggtttaagaa agaaaacaaa accaacagtt agtggagtca agcccagac     1680 actgtaaata gaaccccctc caccaccccc cgccgcccag catcctacct ggactgcggt    1740
gctacgaggg cctgcgggcc tttgctgtgt gccaccctcc ctgtaagtct atttaaaaac    1800
atcgacgata cattgaaatg tgtgaacgtt ttgaaaagct acagcttcca gcagccaaaa    1860
gcaactgttg ttttggcaag acggtcctga tgtacaagct tgattgaaat tcactgctca    1920
cttgatacgt tattcagaaa cccaaggaat ggctgtcccc atcctcatgt ggctgtgtgg    1980
agctcagctg tgttgtgtgg cagtttatta aactgtcccc cagatcgaca cgcaaaaaaa    2040
aaaaaaaa                                                             2048
```

<210> SEQ ID NO 9
<211> LENGTH: 1960
<212> TYPE: DNA
<213> ORGANISM: Homo sapiens

<400> SEQUENCE: 9

```
ttcctcccgg cgtgctccgc ggctcttggc tcacagccgt cccttcgctg gtgggaagaa      60
gccgagatgg cggcagccag cgctggggca accggctgc tcctgctctt gctgatggcg     120
gtagcagcgc ccagtcgagc ccggggcagc ggctgccggg ccgggactgg tgcgcgaggg    180 gctgggggcgg aaggtcgaga gggcgaggcc tgtggcacgg tggggctgct gctggagcac    240
tcatttgaga tcgatgacag tgccaacttc cggaagcggg gctcactgct ctggaaccag    300
caggatggta ccttgtccct gtcacagcgg cagctcagcg aggaggagcg gggccgactc    360
cgggatgtgg cagccctgaa tggcctgtac cgggtccgga tcccaaggcg acccggggcc    420
ctggatggcc tggaagctgg tggctatgtc tcctcctttg tccctgcgtg ctccctggtg    480
gagtcgcacc tgtcggacca gctgaccctg cacgtggatg tggccggcaa cgtggtgggc    540
gtgtcggtgg tgacgcaccc cggggggctgc cggggccatg aggtggagga cgtggacctg    600
gagctgttca acacctcggt gcagctgcag ccgcccacca cagccccagg ccctgagacg    660
gcggccttca ttgagcgcct ggagatgaaa caggcccaga aggccaagaa ccccccaggag    720 cagaagtcct tcttcgccaa atactggatg tacatcattc ccgtcgtcct gttcctcatg    780
atgtcaggag cgccagacac cggggggccag ggtgggggtg ggggtggggg tggtggtggg    840
ggtagtggcc ggtgagggcc caggctggtc agcgtcccgt cttgcacacc caggggcctc    900
cctttctgct ggagtcccct gtgtcctcag ccatcccaag aagggtttgc tggtccctcc    960 tttcccccg tccacgagg ccacctgggc cagcccttg tcctctgcct tctgctggca     1020
gaggagcagc tggactgggg cctttggcac agcagccggt gtctcctgcg cccgcctccc    1080
```

| | |
|---|---:|
| ccatggcccc atgcagcccc aggggcttcc cccctgccca tggagtagag cccgagatcc | 1140 |
| tggccactat gccagttctg acctcgcatc ccctaccc gagcccatgc agtctgggaa | 1200 |
| catgccgcct tctctccagc ctctgtgcct ttgttccagg tggtctcacc ctcctgtccc | 1260 |
| tggctgggct aggtggtcct gtccaggctc ctgcagcgcc ccctcactt tgacactgga | 1320 |
| ctaggatgca gcctcccttc tgtgtcccct tgagggtacc ctgggtcccc tcatcagggg | 1380 |
| cagaggcatg aaagagtcgg ggctggatgg ccggggggctt ctgggcccga cgcctagtgc | 1440 |
| agcccctggg gtcgtggttt gacatttgtc tgcctggtgc aaacaaggaa tccttgcctt | 1500 |
| taaggtgaca ggccctccac aggcttccag acttgaagga aaggttttaa gaaagaaaac | 1560 |
| aaaaccaaca gttagtggag tcaaagccca gacactgtaa atagaacccc ctccaccacc | 1620 |
| ccccgccgcc cagcatccta cctggactgc ggtgctacga gggcctgcgg gcctttgctg | 1680 |
| tgtgccaccc tccctgtaag tctatttaaa aacatcgacg atacattgaa atgtgtgaac | 1740 |
| gttttgaaaa gctacagctt ccagcagcca aaagcaactg ttgttttggc aagacggtcc | 1800 |
| tgatgtacaa gcttgattga aattcactgc tcacttgata cgttattcag aaacccaagg | 1860 |
| aatggctgtc cccatcctca tgtggctgtg tggagctcag ctgtgttgtg tggcagttta | 1920 |
| ttaaactgtc ccccagatcg acacgcaaaa aaaaaaaaaa | 1960 |

<210> SEQ ID NO 10
<211> LENGTH: 1627
<212> TYPE: DNA
<213> ORGANISM: Mus musculus

<400> SEQUENCE: 10

| | |
|---|---:|
| gggctgtatg gctctcggtt tttctcaacg ctcccgtatg gtggccgcgg gtgccggggt | 60 |
| gacccggctg ctagtgctct tgctgatggt agccgcggct cctagcagag cccgaggcag | 120 |
| cggctgccgg gtcggggcct ccgcgcgtgg gaccggggcc gatggccgtg aagctgaggg | 180 |
| ctgtggcacc gtggctttgc tgctggagca ttcatttgag ctcggtgatg gagccaactt | 240 |
| ccagaagcga ggcttgctgc tctggaacca gcaggatggc accctgtcgg caacacagcg | 300 |
| acagctcagt gaggaggagc gtggccgact ccgggatgtg gctgctgtca atggcctcta | 360 |
| cagggtccgg gtcccgaggc ggcctgggac acttgatggt tcagaagctg gcggccatgt | 420 |
| gtcttccttc gtcccagcgt gctccctggt ggagtcgcac ctttcggacc agctgacctt | 480 |
| gcacgtggat gtggctggca acgtggtggg cctgtctgtg gtggtgtacc ctggggggctg | 540 |
| ccggggctcc gaggtggaag atgaggacct ggagctgttc aatacatctg tgcagctgcg | 600 |
| gcctcccagc actgctccag gccccgagac tgcagccttc attgagcgcc tggagatgga | 660 |
| gcaggcccag aaggccaaga acccacagga gcagaagtct ttctttgcca aatactggca | 720 |
| cctcatcctg ggggggccg tgttgctcac agccctacgt cctgctgccc cagggcctgc | 780 |
| accagcgcca acgaggcct aatggatgta catcattcca gttgtgctgt tcctcatgat | 840 |
| gtcgggagcg ccggacgctg ggggccaggg cggcggtggg ggcggggggca gcagccggtg | 900 |
| agcagctgtg ccacctagag cccccccccag agccagccca agaaggagtt cctgtcccca | 960 |
| catttcccta ttgcatgaat atggaaggct gtcccttcag tgagccctct ggccttcctg | 1020 |
| taagcccctc tttctgtccc tgagcctctc tctcatcctg ttgactgaga gcttgggtgg | 1080 |
| acctccctgt agccagctca ctgcaactgt gtcccaccat gtggcactgt gctcctctgt | 1140 |
| ctgctaaaca cccaccagcc tgccccaccc caccccacca tacactttgg gaacttgcca | 1200 |
| agctctctcc agcctctgtg cctttgccct gcaggccccg tgcgcccctc actgtcactc | 1260 |

-continued

| | |
|---|---|
| tccagccctt tgccaaggat ctgtggccca gaggcctctg ctcttagtgg ctaggtcagc | 1320 |
| ctccagccca ctgtccaggt ggcatgctgt cttctttgcc ccctctctg gtgccccaga | 1380 |
| ataccatggt gacctaccac tatcctttct gcctttggat gtcatagcct ggatctgtca | 1440 |
| ccaggagagg attgtgggcc tccacgttag tctgtgaatg cacacttcga gtgacttgtg | 1500 |
| tgcaggtttt gagagccggt tttgcactag ctgctcgaca gctgctggca tggccgtgct | 1560 |
| cttgcacatg cgccgctgtg ggcatgggga ttgctgtgca gcctcagctg tgttgtgtgg | 1620 |
| ctgctga | 1627 |

<210> SEQ ID NO 11
<211> LENGTH: 1855
<212> TYPE: DNA
<213> ORGANISM: Mus musculus

<400> SEQUENCE: 11

| | |
|---|---|
| gagaaatggc cgccctgact gcgggagcag gcggacgggc gctagtgcgc aggcgcggcg | 60 |
| tgcggcgcag gcgcgtgagc ctcaggatga accctgtgtt tcctagcggg ctgtatggct | 120 |
| ctcggttttt ctcaacgctc ccgtatggtg gccgcgggtg ccggggtgac ccggctgcta | 180 |
| gtgctcttgc tgatggtagc cgcggctcct agcagagccc gaggcagcgg ctgccgggtc | 240 |
| ggggcctccg cgcgtgggac cggggccgat ggccgtgaag ctgagggctg tggcaccgtg | 300 |
| gctttgctgc tggagcattc atttgagctc ggtgatggag ccaacttcca gaagcgaggc | 360 |
| ttgctgctct ggaaccagca ggatggcacc ctgtcggcaa cacagcgaca gctcagtgag | 420 |
| gaggagcgtg gccgactccg ggatgtggct gctgtcaatg gcctctacag ggtccgggtc | 480 |
| ccgaggcggc ctgggacact tgatggttca gaagctggcg gccatgtgtc ttccttcgtc | 540 |
| ccagcgtgct ccctggtgga gtcgcacctt tcggaccagc tgaccttgca cgtggatgtg | 600 |
| gctggcaacg tggtgggcct gtctgtggtg gtgtaccctg ggggctgccg gggctccgag | 660 |
| gtggaagatg aggacctgga gctgttcaat acatctgtgc agctgcggcc tcccagcact | 720 |
| gctccaggcc ccgagactgc agccttcatt gagcgcctgg agatggagca ggcccagaag | 780 |
| gccaagaacc cacaggagca gaagtctttc tttgccaaat actggatgta catcattcca | 840 |
| gttgtgctgt tcctcatgat gtcgggagcg ccggacgctg ggggccaggg cggcggtggg | 900 |
| ggcggggca gcagccggtg agcagctgtg ccacctagag cccccccag agccagccca | 960 |
| agaaggagtt cctgtcccca catttcccta ttgcatgaat atggaaggct gtcccttcag | 1020 |
| tgagccctct ggccttcctg taagcccctc tttctgtccc tgagcctctc tctcatcctg | 1080 |
| ttgactgaga gcttgggtgg acctccctgt agccagctca ctgcaactgt gtcccaccat | 1140 |
| gtggcactgt gctcctctgt ctgctaaaca cccaccagcc tgcccacccc caccccacca | 1200 |
| tacactttgg gaacttgcca agctctctcc agcctctgtg cctttgccct gcaggccccg | 1260 |
| tgcgcccctc actgtcactc tccagccctt tgccaaggat ctgtggccca gaggcctctg | 1320 |
| ctcttagtgg ctaggtcagc ctccagccca ctgtccaggt ggcatgctgt cttctttgcc | 1380 |
| ccctctctg gtgccccaga ataccatggt gacctaccac tatcctttct gcctttggat | 1440 |
| gtcatagcct ggatctgtca ccaggagagg attgtgggcc tccacgttag tctgtgaatg | 1500 |
| cacacttcga gtgacttgtg tgcaggtttt gagagccggt tttgcactag ctgctcgaca | 1560 |
| gctgctggca tggccgtgct cttgcacatg cgccgctgtg ggcatgggga ttgctgtgca | 1620 |
| gcctcagctg tgttgtgtgg ctgctgatta aactgtcccc taaacagcca ctcttcagct | 1680 |

```
cacttcctgc cttctgtgct tgtgaatagt cctgagttgc cgctgtggtt tgcctggttt    1740
atgtttgaat ggcttttctta gggtatgtta cagaggggtg cctgagcaga ttaaagttgc    1800
tgtgagcaag gacgccttcc gaactctggg aggaggctgg ttcctgaccc tccta          1855
```

<210> SEQ ID NO 12
<211> LENGTH: 173
<212> TYPE: PRT
<213> ORGANISM: Macaca mulatta

<400> SEQUENCE: 12

```
Met Ala Ala Pro Ser Gly Gly Trp Asn Gly Val Gly Ala Ser Leu Trp
1               5                   10                  15

Ala Ala Leu Leu Leu Gly Ala Val Ala Leu Ser Pro Ala Glu Ala Val
            20                  25                  30

Ser Glu Pro Thr Thr Val Ala Phe Asp Val Arg Pro Gly Gly Val Val
        35                  40                  45

His Ser Phe Ser His Asn Val Gly Pro Gly Asp Lys Tyr Thr Cys Met
    50                  55                  60

Phe Thr Tyr Ala Ser Gln Gly Gly Thr Asn Glu Gln Trp Gln Met Ser
65                  70                  75                  80

Leu Gly Thr Ser Glu Asp His Gln His Phe Thr Cys Thr Ile Trp Arg
                85                  90                  95

Pro Gln Gly Lys Ser Tyr Leu Tyr Phe Thr Gln Phe Lys Ala Glu Val
            100                 105                 110

Arg Gly Ala Glu Ile Glu Tyr Ala Met Ala Tyr Ser Lys Ala Ala Phe
        115                 120                 125

Glu Arg Glu Ser Asp Val Pro Leu Lys Thr Glu Glu Phe Glu Val Thr
    130                 135                 140

Lys Thr Ala Val Ala His Arg Pro Gly Ala Phe Lys Ala Glu Leu Ser
145                 150                 155                 160

Lys Leu Val Ile Val Ala Lys Ala Ser Arg Thr Glu Leu
                165                 170
```

<210> SEQ ID NO 13
<211> LENGTH: 166
<212> TYPE: PRT
<213> ORGANISM: Mus musculus

<400> SEQUENCE: 13

```
Met Ala Ala Pro Ser Gly Gly Phe Trp Thr Ala Val Val Leu Ala Ala
1               5                   10                  15

Ala Ala Leu Lys Leu Ala Ala Ala Val Ser Glu Pro Thr Thr Val Pro
            20                  25                  30

Phe Asp Val Arg Pro Gly Gly Val Val His Ser Phe Ser Gln Asp Val
        35                  40                  45

Gly Pro Gly Asn Lys Phe Thr Cys Thr Phe Thr Tyr Ala Ser Gln Gly
    50                  55                  60

Gly Thr Asn Glu Gln Trp Gln Met Ser Leu Gly Thr Ser Glu Asp Ser
65                  70                  75                  80

Gln His Phe Thr Cys Thr Ile Trp Arg Pro Gln Gly Lys Ser Tyr Leu
                85                  90                  95

Tyr Phe Thr Gln Phe Lys Ala Glu Leu Arg Gly Ala Glu Ile Glu Tyr
            100                 105                 110

Ala Met Ala Tyr Ser Lys Ala Ala Phe Glu Arg Glu Ser Asp Val Pro
        115                 120                 125
```

```
Leu Lys Ser Glu Glu Phe Glu Val Thr Lys Thr Ala Val Ser His Arg
    130                 135                 140

Pro Gly Ala Phe Lys Ala Glu Leu Ser Lys Leu Val Ile Val Ala Lys
145                 150                 155                 160

Ala Ala Arg Ser Glu Leu
                165

<210> SEQ ID NO 14
<211> LENGTH: 174
<212> TYPE: PRT
<213> ORGANISM: Bos taurus

<400> SEQUENCE: 14

Met Ala Ala Pro Ser Gly Arg Arg Asn Gly Ser Gly Ala Asn Leu
1               5                   10                  15

Trp Val Ser Leu Leu Ala Ala Ala Leu Arg Pro Val Glu Thr
                20                  25                  30

Val Ser Glu Pro Thr Thr Val Ala Phe Asp Val Arg Pro Gly Gly Val
                35                  40                  45

Val His Ser Phe Ser Gln Asn Val Gly Pro Gly Asp Lys Tyr Thr Cys
            50                  55                  60

Val Phe Thr Tyr Ala Ser Gln Gly Gly Thr Asn Glu Lys Trp Gln Met
65                  70                  75                  80

Ser Leu Gly Thr Ser Glu Asp His Gln His Phe Thr Cys Thr Ile Trp
                85                  90                  95

Arg Pro Gln Gly Lys Ser Tyr Leu Tyr Phe Thr Gln Phe Lys Ala Glu
                100                 105                 110

Val Arg Gly Ala Glu Ile Glu Tyr Gly Met Ala Tyr Ser Lys Ala Ala
            115                 120                 125

Phe Glu Lys Glu Ser Asp Val Pro Leu Lys Asn Glu Glu Phe Glu Val
                130                 135                 140

Thr Lys Thr Ala Val Phe His Arg Pro Gly Ala Phe Lys Ala Glu Leu
145                 150                 155                 160

Ser Lys Leu Val Ile Val Ala Lys Ala Thr Arg Ser Glu Leu
                165                 170

<210> SEQ ID NO 15
<211> LENGTH: 174
<212> TYPE: PRT
<213> ORGANISM: Loxodonta africana

<400> SEQUENCE: 15

Met Ala Ala Pro Arg Gly Arg Arg Asn Gly Ser Ala Gly Ala Ser Met
1               5                   10                  15

Trp Gly Ala Leu Leu Leu Ala Ala Val Ala Leu Arg Ser Val Glu Ala
                20                  25                  30

Val Ser Glu Pro Thr Thr Val Ala Phe Asp Val Arg Pro Gly Gly Val
                35                  40                  45

Val His Ser Phe Ser His Ser Ala Gly Pro Gly Asp Arg Phe Thr Cys
            50                  55                  60

Thr Phe Thr Tyr Ala Ser Gln Gly Gly Thr Asn Glu Gln Trp Gln Met
65                  70                  75                  80

Ser Leu Gly Thr Ser Glu Asp His Gln His Phe Thr Cys Thr Ile Trp
                85                  90                  95

Arg Pro Gln Gly Lys Ser Tyr Leu Tyr Phe Thr Gln Phe Lys Ala Glu
                100                 105                 110
```

```
Val Arg Gly Ala Gln Ile Glu Tyr Gly Met Ala Tyr Ser Lys Ala Ala
        115                 120                 125

Ser Glu Arg Glu Ser Asp Val Pro Leu Lys Asn Glu Glu Phe Glu Val
130                     135                 140

Thr Lys Thr Thr Val Ala His Arg Pro Gly Ala Phe Lys Ala Glu Leu
145                 150                 155                 160

Ser Lys Leu Val Ile Val Ala Lys Ala Ser His Ser Glu Leu
            165                 170
```

<210> SEQ ID NO 16
<211> LENGTH: 173
<212> TYPE: PRT
<213> ORGANISM: Heterocephalus glaber

<400> SEQUENCE: 16

```
Met Ala Ala Pro Arg Gly Asn Ser Asp Gly Cys Gly Gly Ala Trp Phe
1               5                   10                  15

Ala Ala Leu Leu Leu Ala Ala Val Ala Leu Arg Pro Ala Glu Ala Val
            20                  25                  30

Ser Glu Pro Thr Thr Val Ala Phe Asp Val Arg Pro Gly Gly Val Val
        35                  40                  45

His Ser Phe Ser Gln Asn Val Gly Pro Gly Asp Lys Phe Thr Cys Thr
    50                  55                  60

Phe Thr Tyr Ala Ser Gln Gly Gly Thr Asn Glu Gln Trp Gln Met Ser
65                  70                  75                  80

Leu Gly Thr Ser Glu Asp His Gln His Phe Thr Cys Ile Ile Trp Arg
                85                  90                  95

Pro Gln Gly Lys Ser Tyr Leu Tyr Phe Thr Gln Phe Lys Ala Glu Val
                100                 105                 110

His Gly Ala Glu Ile Glu Tyr Ala Met Ala Tyr Ser Lys Ala Ala Phe
            115                 120                 125

Glu Arg Glu Ser Asp Val Pro Leu Lys Asn Glu Glu Phe Glu Val Thr
130                 135                 140

Lys Ala Ala Val Ala His Arg Pro Gly Ala Phe Arg Ala Glu Leu Ser
145                 150                 155                 160

Lys Leu Val Ile Val Ala Lys Glu Ala His Ser Glu Leu
            165                 170
```

<210> SEQ ID NO 17
<211> LENGTH: 173
<212> TYPE: PRT
<213> ORGANISM: Mustela putorius furo

<400> SEQUENCE: 17

```
Met Ala Ala Pro Ser Glu Arg Arg Asn Gly Gly Gly Ala Ser Leu Trp
1               5                   10                  15

Ala Ala Leu Leu Leu Ala Ala Ala Ala Leu Arg Pro Ala Glu Ala Val
            20                  25                  30

Ser Glu Pro Thr Thr Val Ala Phe Asp Val Arg Pro Gly Gly Val Val
        35                  40                  45

His Ser Phe Ser Gln Asn Val Gly Pro Gly Asp Lys Tyr Thr Cys Ala
    50                  55                  60

Phe Thr Tyr Ala Ser Gln Gly Gly Thr Asn Glu Lys Trp Gln Met Ser
65                  70                  75                  80

Leu Gly Ile Ser Glu Asp His Gln His Phe Thr Cys Thr Ile Trp Arg
                85                  90                  95
```

Pro Gln Gly Lys Ser Tyr Leu Tyr Phe Thr Gln Phe Arg Ala Glu Val
                100                 105                 110

Arg Gly Ala Glu Ile Glu Tyr Gly Met Ala Tyr Ser Lys Ala Ala Phe
            115                 120                 125

Glu Arg Glu Ser Asp Val Pro Leu Lys Ser Glu Glu Phe Glu Val Thr
130                 135                 140

Lys Thr Ala Val Ser His Arg Pro Gly Ala Phe Lys Ala Glu Leu Ser
145                 150                 155                 160

Lys Leu Val Ile Val Ala Lys Ala Ser Arg Ser Glu Leu
                165                 170

<210> SEQ ID NO 18
<211> LENGTH: 167
<212> TYPE: PRT
<213> ORGANISM: Gallus gallus

<400> SEQUENCE: 18

Met Ala Ala Pro Cys Gly Arg Ser Ser Arg Trp Leu Trp Ala Ala Val
1               5                   10                  15

Val Pro Ala Ala Val Leu Cys Leu Ala Val Arg Ala Ala Glu Glu Ala
                20                  25                  30

Ser Thr Ala Glu Phe Asp Val Arg Pro Gly Gly Val His Phe Phe
            35                  40                  45

Ser Arg Ser Leu Gly Asp Tyr Thr Cys Thr Phe Thr Tyr Ser Ala Gln
    50                  55                  60

Gly Gly Thr Asn Glu Gln Trp Gln Met Asn Ile Gly Val Ser Glu Asp
65                  70                  75                  80

Asn Leu Leu Phe Ser Cys Ser Val Trp Arg Pro Gln Gly Lys Ser Tyr
                85                  90                  95

Leu Phe Phe Thr Gln Phe Lys Ala Glu Val Lys Gly Ala Lys Ile Glu
                100                 105                 110

Tyr Ala Met Ala Tyr Ser Gln Ala Ala Val Gly Ala Gln Ser Asp Ile
            115                 120                 125

Pro Leu Lys Gln Glu Glu Phe Glu Ile Thr Glu Thr Thr Val Ser His
130                 135                 140

Arg Glu Gly Lys Phe Arg Phe Glu Leu Ser Lys Leu Met Ile Val Ala
145                 150                 155                 160

Lys Thr Pro His Asp Glu Leu
                165

<210> SEQ ID NO 19
<211> LENGTH: 169
<212> TYPE: PRT
<213> ORGANISM: Oreochromis niloticus

<400> SEQUENCE: 19

Met Ala Arg Gln Ser Asn Thr Cys Ala Gly Asn Leu Ala Phe Leu Phe
1               5                   10                  15

Ala Leu Ala Leu Ile Ala Ala Arg Val Pro Ala Glu Ala Ser Glu Glu
                20                  25                  30

Gln Ala Lys Thr Val Glu Phe Asn Val Lys Pro Gly Gly Val Val His
            35                  40                  45

Thr Phe Ser Glu Gly Ile Gly Glu Tyr Glu Cys Ser Phe Thr Tyr Ala
    50                  55                  60

Ser Gln Gly Gly Thr Asn Glu Gln Trp Leu Met Ser Val Gly Leu Thr
65                  70                  75                  80

Asp Asp Asn Arg Leu Phe Ser Cys Ser Val Trp Arg Pro Gln Gly Lys
            85                  90                  95

Ser Tyr Leu Phe Phe Thr Gln Phe Lys Ala Glu Leu Lys Gly Thr Lys
        100                 105                 110

Ile Glu Tyr Ala Asn Ala Tyr Ser Gln Ser Ala Ala Gly Gly Gln Ser
        115                 120                 125

Asp Val Pro Leu Lys Pro Glu Glu Phe Thr Ile Gly Glu Ser Thr Val
    130                 135                 140

Thr His Lys Asp Gly Lys Phe Ser Ala Gln Leu Ser Lys Leu Thr Val
145                 150                 155                 160

Ile Gly Arg Thr Gln Lys Asp Glu Leu
                165

<210> SEQ ID NO 20
<211> LENGTH: 158
<212> TYPE: PRT
<213> ORGANISM: Xenopus tropicalis

<400> SEQUENCE: 20

Met Ala Thr Tyr Gly Ile Ile Cys Ala Phe Leu Leu Leu Leu Ala Val
1               5                   10                  15

Cys Ser Ala Gln Glu Lys Ser Ser Thr Glu Glu Phe Asp Val Arg Pro
            20                  25                  30

Gly Gly Leu Gln His Ser Phe Thr Ser Lys Leu Gly Asp Tyr Ala Cys
        35                  40                  45

Thr Phe Thr Tyr Ala Ala Gln Gly Gly Thr Asn Glu Lys Trp His Met
    50                  55                  60

Ser Val Gly Leu Ser Asp Asp Asn Gln His Phe Ser Cys Ser Ile Trp
65                  70                  75                  80

Arg Pro Gln Gly Lys Ser Tyr Leu Phe Phe Thr Gly Phe Lys Ala Glu
                85                  90                  95

Val Thr Gly Gly Lys Ile Glu Phe Ser Glu Ala Tyr Ser Gln Ala Ser
            100                 105                 110

Ser Asp Gly Ser Ser Asp Val Lys Leu Lys Ser Ser Glu Tyr Asp Val
        115                 120                 125

Thr Asp Asn Val Val Ser His Arg Pro Gly Ser Phe Ser Ser Ser Leu
    130                 135                 140

Cys Lys Leu Val Leu Val Ala Arg Ser Glu His Asp Glu Leu
145                 150                 155

<210> SEQ ID NO 21
<211> LENGTH: 254
<212> TYPE: PRT
<213> ORGANISM: Macaca mulatta

<400> SEQUENCE: 21

Met Ala Ala Thr Ser Gly Gly Ala Thr Arg Leu Leu Leu Leu Leu Leu
1               5                   10                  15

Met Ala Val Ala Ala Pro Ser Arg Ala Arg Gly Ser Gly Cys Arg Ala
            20                  25                  30

Gly Thr Gly Ala Arg Gly Ala Gly Ala Glu Gly Arg Glu Gly Glu Ala
        35                  40                  45

Cys Gly Thr Val Gly Leu Leu Leu Glu His Ser Phe Glu Ile Asp Asp
    50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
            85                  90                  95

Arg Leu Arg Asp Val Ala Ala Leu Asn Gly Leu Tyr Arg Val Arg Val
        100                 105                 110

Pro Arg Arg Pro Gly Ala Leu Asp Gly Leu Glu Ala Ser Gly Tyr Val
        115                 120                 125

Ser Ser Phe Val Pro Ala Cys Ser Leu Val Glu Ser His Leu Ser Asp
        130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Ala Thr
                180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
        210                 215                 220

Lys Tyr Trp His Ile Ile Leu Gly Gly Ala Val Leu Leu Thr Ala Leu
225                 230                 235                 240

Arg Pro Ala Ala Pro Gly Pro Ala Pro Pro Gln Glu Ala
                245                 250

<210> SEQ ID NO 22
<211> LENGTH: 254
<212> TYPE: PRT
<213> ORGANISM: Cavia porcellus

<400> SEQUENCE: 22

Met Ala Ala Ala Gly Ala Gly Ala Pro Arg Leu Leu Leu Leu Leu Leu
1               5                   10                  15

Ile Val Ala Ala Ala Pro Ser Arg Ala Arg Gly Ser Ser Cys Arg Ala
                20                  25                  30

Gly Ala Ala Thr Arg Gly Val Gly Ala Glu Gly Arg Glu Gly Glu Ser
            35                  40                  45

Cys Gly Thr Val Gly Leu Leu Leu Glu His Ser Phe Glu Ile Asp Asp
        50                  55                  60

Thr Ala Gln Phe Arg Lys Arg Gly Ser Leu Leu Trp Asn Gln Gln Asp
65                  70                  75                  80

Gly Thr Leu Ser Leu Ser Gln Arg Gln Leu Asn Glu Glu Glu Arg Gly
            85                  90                  95

Arg Leu Arg Asp Val Ala Ala Leu Asn Gly Leu Tyr Arg Val Arg Val
        100                 105                 110

Pro Arg Arg Pro Gly Ala Leu Asp Ser Ala Glu Ala Gly Gly Tyr Val
        115                 120                 125

Ser Ser Phe Val Pro Ala Cys Ser Leu Val Glu Ser His Leu Ser Asp
        130                 135                 140

Gln Leu Thr Leu His Val Asp Val Ala Gly Asn Val Val Gly Val Ser
145                 150                 155                 160

Val Val Thr Tyr Pro Gly Gly Cys Arg Gly His Glu Val Glu Asp Val
                165                 170                 175

Asp Leu Glu Leu Phe Asn Thr Ser Val Arg Leu Arg Pro Pro Gly Thr
                180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
    210                 215                 220

Lys Tyr Trp His Leu Ile Leu Gly Gly Ala Val Leu Leu Thr Ala Leu
225                 230                 235                 240

Arg Pro Ala Ala Pro Gly Pro Thr Pro Pro Gln Glu Ala
                245                 250

<210> SEQ ID NO 23
<211> LENGTH: 254
<212> TYPE: PRT
<213> ORGANISM: Canis lupus familiaris

<400> SEQUENCE: 23

Met Ala Ala Ala Gly Ala Val Val Thr Arg Leu Phe Leu Leu Leu Leu
1               5                   10                  15

Met Ala Ala Ala Pro Ser Arg Ala Arg Gly Ser Gly Cys Arg Ser
                20                  25                  30

Gly Ala Ala Leu Arg Gly Ala Gly Ala Glu Gly Arg Glu Ser Glu Gly
            35                  40                  45

Cys Gly Thr Val Gly Leu Leu Leu Glu His Ser Phe Glu Ile Asp Asp
50                  55                  60

Ser Ala His Phe Arg Lys Arg Gly Ser Leu Leu Trp Asn Gln Gln Asp
65                  70                  75                  80

Gly Thr Leu Ser Leu Ser Gln Arg Gln Leu Asn Glu Glu Glu Arg Gly
                85                  90                  95

Arg Leu Arg Asp Val Ala Ala Leu Asn Gly Leu Tyr Arg Val Arg Val
            100                 105                 110

Pro Gln Arg Pro Gly Val Pro Asp Gly Ala Glu Ala Gly Gly Tyr Val
        115                 120                 125

Ser Ser Phe Val Pro Ala Cys Ser Leu Val Glu Ser His Leu Ser Asp
    130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val His Leu Gln Pro Pro Ala Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
    210                 215                 220

Lys Tyr Trp His Leu Val Leu Gly Gly Ala Val Leu Leu Thr Ala Leu
225                 230                 235                 240

Arg Pro Ala Ala Pro Gly Pro Thr Pro Pro Gln Glu Ala
                245                 250

<210> SEQ ID NO 24
<211> LENGTH: 254
<212> TYPE: PRT
<213> ORGANISM: Mus musculus

<400> SEQUENCE: 24

Met Val Ala Ala Gly Ala Gly Val Thr Arg Leu Leu Val Leu Leu Leu
1               5                   10                  15

Met Val Ala Ala Ala Pro Ser Arg Ala Arg Gly Ser Gly Cys Arg Val
                20                  25                  30

Gly Ala Ser Ala Arg Gly Thr Gly Ala Asp Gly Arg Glu Ala Glu Gly
            35                  40                  45

Cys Gly Thr Val Ala Leu Leu Leu Glu His Ser Phe Glu Leu Gly Asp
        50                  55                  60

Gly Ala Asn Phe Gln Lys Arg Gly Leu Leu Trp Asn Gln Gln Asp
65                  70                  75                  80

Gly Thr Leu Ser Ala Thr Gln Arg Gln Leu Ser Glu Glu Arg Gly
            85                  90                  95

Arg Leu Arg Asp Val Ala Ala Val Asn Gly Leu Tyr Arg Val Arg Val
            100                 105                 110

Pro Arg Arg Pro Gly Thr Leu Asp Gly Ser Glu Ala Gly Gly His Val
            115                 120                 125

Ser Ser Phe Val Pro Ala Cys Ser Leu Val Glu Ser His Leu Ser Asp
        130                 135                 140

Gln Leu Thr Leu His Val Asp Val Ala Gly Asn Val Val Gly Leu Ser
145                 150                 155                 160

Val Val Val Tyr Pro Gly Gly Cys Arg Gly Ser Glu Val Glu Asp Glu
                165                 170                 175

Asp Leu Glu Leu Phe Asn Thr Ser Val Gln Leu Arg Pro Pro Ser Thr
            180                 185                 190

Ala Pro Gly Pro Glu Thr Ala Ala Phe Ile Glu Arg Leu Glu Met Glu
            195                 200                 205

Gln Ala Gln Lys Ala Lys Asn Pro Gln Glu Gln Lys Ser Phe Phe Ala
        210                 215                 220

Lys Tyr Trp His Leu Ile Leu Gly Gly Ala Val Leu Leu Thr Ala Leu
225                 230                 235                 240

Arg Pro Ala Ala Pro Gly Pro Ala Pro Ala Pro Thr Glu Ala
            245                 250

<210> SEQ ID NO 25
<211> LENGTH: 254
<212> TYPE: PRT
<213> ORGANISM: Equus caballus

<400> SEQUENCE: 25

Met Ala Ala Ala Gly Ala Gly Ala Thr Arg Leu Leu Leu Leu Leu Leu
1               5                   10                  15

Met Ala Ala Ala Ala Pro Ser Arg Ala Arg Gly Ser Gly Cys Arg Pro
            20                  25                  30

Gly Thr Ala Ala Arg Gly Ala Gly Ala Glu Gly Arg Glu Gly Glu Gly
            35                  40                  45

Cys Gly Pro Val Gly Leu Leu Leu Glu His Ser Phe Glu Ile Asp Asp
        50                  55                  60

Asn Ala His Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Arg Gly
            85                  90                  95

Arg Leu Arg Asp Val Ala Ala Leu Asn Gly Leu Tyr Arg Val Arg Val
            100                 105                 110

Pro Arg Arg Pro Gly Thr Pro Asp Gly Leu Glu Ala Gly Gly Tyr Val
            115                 120                 125

Ser Ser Phe Val Pro Ala Cys Ser Leu Val Glu Ser His Leu Ser Asp
        130                 135                 140

Gln Leu Thr Leu His Val Asp Val Ala Gly Asn Val Val Gly Val Ser

```
145                 150                 155                 160
Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Val Thr
                180                 185                 190

Ala Pro Gly Pro Glu Thr Ala Ala Phe Ile Glu Arg Leu Glu Met Glu
                195                 200                 205

Gln Ala Gln Lys Ala Lys Asn Pro Gln Glu Gln Lys Ser Phe Phe Ala
        210                 215                 220

Lys Tyr Trp His Leu Ile Leu Gly Gly Ala Val Leu Leu Thr Ala Leu
225                 230                 235                 240

Arg Pro Ala Ala Pro Gly Pro Ala Pro Pro Gln Glu Ala
                245                 250
```

<210> SEQ ID NO 26
<211> LENGTH: 258
<212> TYPE: PRT
<213> ORGANISM: Xenopus laevis

<400> SEQUENCE: 26

```
Gly Gly Gln Arg Ala Gly Pro Leu Ser Ser Ile Val Thr Gly Asn Cys
1               5                   10                  15

Trp Val Trp Leu Ile Ala Leu Pro Phe Leu Ala Val Thr Ala Gln Gly
                20                  25                  30

Ser Val Cys Arg Leu Lys Thr Gly Asp Gly Arg Glu Ser Glu Ser Cys
            35                  40                  45

Gly Thr Asn Leu Glu Leu Glu His Ser Phe Glu Leu Asp Asp Ser Ile
        50                  55                  60

His Phe Thr Lys Arg Gly Ser Leu Phe Trp Ser Gly Thr Ala Glu Gln
65                  70                  75                  80

Ser Ile Ser Ile Leu Gln Lys Gln Leu Thr Glu Asp Glu Arg Asn Lys
                85                  90                  95

Leu Arg Asp Ile Ala Asn Leu Asn Gly Leu Tyr Arg Ile Arg Ile Pro
            100                 105                 110

Arg Lys Leu Gly Ile Thr Glu Glu Ala Asn Glu Tyr Val Thr Ser Phe
        115                 120                 125

Val Arg Ala Cys Ser Met Val Glu Ser His Leu Ser Asp Glu Ile Thr
130                 135                 140

Val His Thr Asp Leu Ser Gly Asn Val Ile Gly Val Ser Ile Val Thr
145                 150                 155                 160

Phe Pro Gly Ser Cys Asn Gly Ala Glu Val Asp Val Asp Leu Glu
                165                 170                 175

Met Phe Asn Thr Thr Val His Met Gln Gln Pro Ile Pro Ala Ala Val
                180                 185                 190

Pro Glu Thr Ala Ala Phe Ile Glu Arg Leu Glu Met Glu Gln Ala Gln
            195                 200                 205

Lys Ala Lys Asn Pro Gln Glu Gln Lys Ser Phe Phe Ala Lys Tyr Trp
        210                 215                 220

Met Tyr Ile Ile Pro Val Val Leu Phe Leu Met Met Ser Gly Ala Ser
225                 230                 235                 240

Asp Ala Gly Asn Gln Gly Gly Asn Gly Gly Gly Gly Gly Gly
                245                 250                 255

Gly Arg
```

<210> SEQ ID NO 27
<211> LENGTH: 251
<212> TYPE: PRT
<213> ORGANISM: Danio rerio

<400> SEQUENCE: 27

Met Ala Pro Ile Arg Val Leu Ser Leu Val Leu Pro Ile Leu Ser Thr
1               5                   10                  15

Val Pro Leu Leu Leu Thr Gln Phe Gly Glu Cys Asn Asn Gly Arg Arg
            20                  25                  30

Ser Gly Asp Ala Val Asp Thr Asp Phe Ser Gly Phe Ser Val Pro Leu
        35                  40                  45

Glu His Ser Phe Glu Val Asp Asp Val Pro Arg Phe Arg Leu Arg Gly
    50                  55                  60

Ala Leu Gln Phe Arg Gly Gly Arg Glu Asn Ser Val Tyr Leu Ser Gln
65                  70                  75                  80

Asn Gln Leu Ser Glu Lys Asp Arg Asn Thr Leu Lys Asp Val Ala Ala
                85                  90                  95

Val Asp Gly Leu Tyr Arg Ile Arg Val Pro Arg Val Ser Leu Gln Val
            100                 105                 110

Asp Arg Gln Thr Glu Arg Gln Tyr Glu Gly Tyr Leu Thr Ala Phe Val
        115                 120                 125

Arg Ala Cys Ala Leu Val Glu Ser His Leu Ser Asp Val Ile Thr Leu
130                 135                 140

His Thr Asp Val Ser Gly Tyr Val Ile Gly Ile Ser Ile Val Thr Ile
145                 150                 155                 160

Pro Gly Ser Cys Arg Gly Ile Glu Val Glu Asp Glu Val Asp Leu Glu
                165                 170                 175

Val Phe Asn Thr Thr Ile Ser Val Met Ala Pro Val Thr Ala Pro Val
            180                 185                 190

Pro Glu Thr Ala Pro Tyr Ile Glu Arg Met Glu Met Glu Met Glu Lys
        195                 200                 205

Lys Gly Lys Asn Pro Gln Glu Gln Lys Ser Phe Phe Ala Lys Tyr Trp
210                 215                 220

Tyr Leu Ile Leu Gly Gly Ala Val Phe Leu Met Ala Thr Ser Ser Ala
225                 230                 235                 240

Gln Thr Pro Pro Gly Gly Ala Arg Glu Gln Ser
                245                 250

<210> SEQ ID NO 28
<211> LENGTH: 262
<212> TYPE: PRT
<213> ORGANISM: Pan troglodytes

<400> SEQUENCE: 28

Met Ala Ala Ala Ser Ala Gly Ala Thr Arg Leu Leu Leu Leu Leu Leu
1               5                   10                  15

Met Ala Val Ala Ala Pro Ser Arg Ala Arg Gly Ser Ser Cys Arg Ala
            20                  25                  30

Gly Thr Gly Ala Arg Gly Ala Gly Ala Glu Gly Arg Glu Gly Glu Ala
        35                  40                  45

Cys Gly Thr Val Gly Leu Leu Leu Glu His Ser Phe Glu Ile Asp Asp
    50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly

```
                    85                  90                  95
Arg Leu Arg Asp Val Ala Ala Leu Asn Gly Leu Tyr Arg Val Arg Ile
            100                 105                 110

Pro Arg Arg Pro Gly Ala Leu Asp Gly Leu Glu Ala Gly Gly Tyr Val
            115                 120                 125

Ser Ser Phe Val Pro Ala Cys Ser Leu Val Glu Ser His Leu Ser Asp
130                 135                 140

Gln Leu Thr Leu His Val Asp Val Ala Gly Asn Val Val Gly Val Ser
145                 150                 155                 160

Val Val Thr Gln Pro Gly Gly Cys Arg Gly His Glu Val Glu Asp Val
                165                 170                 175

Asp Leu Glu Leu Phe Thr Thr Ser Val Gln Leu Gln Pro Pro Thr Thr
                180                 185                 190

Ala Pro Gly Pro Glu Thr Ala Ala Phe Ile Glu Arg Leu Glu Met Glu
                195                 200                 205

Gln Ala Gln Lys Ala Lys Asn Pro Gln Glu Gln Lys Ser Phe Phe Ala
            210                 215                 220

Lys Tyr Trp Met Tyr Ile Ile Pro Val Val Leu Phe Leu Met Met Ser
225                 230                 235                 240

Gly Ala Pro Asp Thr Gly Gly Gln Gly Gly Gly Gly Gly Gly Gly Gly
                245                 250                 255

Gly Gly Gly Ser Gly Arg
            260

<210> SEQ ID NO 29
<211> LENGTH: 258
<212> TYPE: PRT
<213> ORGANISM: Mus musculus

<400> SEQUENCE: 29

Met Val Ala Ala Gly Ala Gly Val Thr Arg Leu Leu Val Leu Leu Leu
1               5                   10                  15

Met Val Ala Ala Ala Pro Ser Arg Ala Arg Gly Ser Gly Cys Arg Val
                20                  25                  30

Gly Ala Ser Ala Arg Gly Thr Gly Ala Asp Gly Arg Glu Ala Glu Gly
            35                  40                  45

Cys Gly Thr Val Ala Leu Leu Leu Glu His Ser Phe Glu Leu Gly Asp
50                  55                  60

Gly Ala Asn Phe Gln Lys Arg Gly Ser Leu Leu Trp Asn Gln Gln Asp
65                  70                  75                  80

Gly Thr Leu Ser Ala Thr Gln Arg Gln Leu Ser Glu Glu Glu Arg Gly
                85                  90                  95

Arg Leu Arg Asp Val Ala Ala Val Asn Gly Leu Tyr Arg Val Arg Val
            100                 105                 110

Pro Arg Arg Pro Gly Thr Leu Asp Gly Ser Glu Ala Gly Gly His Val
            115                 120                 125

Ser Ser Phe Val Pro Ala Cys Ser Leu Val Glu Ser His Leu Ser Asp
130                 135                 140

Gln Leu Thr Leu His Val Asp Val Ala Gly Asn Val Val Gly Leu Ser
145                 150                 155                 160

Val Val Val Tyr Pro Gly Gly Cys Arg Gly Ser Glu Val Glu Asp Glu
                165                 170                 175

Asp Leu Glu Leu Phe Asn Thr Ser Val Gln Leu Arg Pro Pro Ser Thr
                180                 185                 190
```

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
    210                 215                 220

Lys Tyr Trp Met Tyr Ile Ile Pro Val Val Leu Phe Leu Met Met Ser
225                 230                 235                 240

Gly Ala Pro Asp Ala Gly Gly Gln Gly Gly Gly Gly Gly Gly Gly Ser
                245                 250                 255

Ser Arg

<210> SEQ ID NO 30
<211> LENGTH: 210
<212> TYPE: PRT
<213> ORGANISM: Heterocephalus glaber

<400> SEQUENCE: 30

Met Val Met Ala Ala Ser Gly Ala Ser Ala Ser Arg Leu Leu Leu Leu
1               5                   10                  15

Leu Leu Ile Val Ala Ala Ala Pro Ser Arg Ala Arg Gly Ser Gly Cys
            20                  25                  30

Arg Ala Gly Ala Ala Ala Arg Gly Val Gly Ala Glu Gly Arg Glu Gly
        35                  40                  45

Glu Ser Cys Gly Thr Val Gly Leu Leu Leu Glu His Ser Phe Glu Ile
    50                  55                  60

Asp Asp Ala Ala His Phe Arg Lys Arg Gly Ser Leu Leu Trp Asn Gln
65                  70                  75                  80

Gln Asp Gly Thr Leu Ser Pro Ser Gln Arg Gln Leu Ser Glu Glu Glu
                85                  90                  95

Arg Gly Arg Leu Arg Asp Val Ala Leu Asn Gly Leu Tyr Arg Val
            100                 105                 110

Arg Val Pro Arg Arg Pro Gly Ala Leu Asp Ser Ser Glu Ala Gly Gly
        115                 120                 125

Tyr Val Ser Ser Phe Val Pro Ala Cys Ser Leu Val Glu Ser His Leu
    130                 135                 140

Ser Asp Gln Leu Thr Leu His Val Asp Val Ala Gly Asn Val Val Gly
145                 150                 155                 160

Val Ser Val Val Thr Asp Pro Gly Gly Cys Arg Gly His Glu Val Glu
                165                 170                 175

Asp Val Asp Leu Glu Leu Phe Asn Thr Ser Val Gln Leu Gln Pro Pro
            180                 185                 190

Gly Thr Ala Pro Gly Pro Glu Thr Ala Ala Phe Ile Glu Arg Leu Glu
        195                 200                 205

Met Glu
    210

<210> SEQ ID NO 31
<211> LENGTH: 262
<212> TYPE: PRT
<213> ORGANISM: Loxodonta africana

<400> SEQUENCE: 31

Met Ala Ala Ala Gly Ala Gly Ala Thr Arg Leu Leu Leu Leu Leu Leu
1               5                   10                  15

Met Ala Ala Ala Ala Pro Ser Arg Ala Arg Gly Ser Ser Cys Arg Ala
            20                  25                  30

Gly Ala Ala Thr Arg Gly Ala Gly Ala Glu Gly Arg Glu Asn Glu Gly 35                  40                  45
Cys Gly Thr Val Gly Leu Leu Leu Glu His Ser Phe Glu Ile Asp Asp
 50                  55                  60

Ala Met His Phe Arg Lys Arg Gly Ser Leu Leu Trp Asn Gln Gln Asp
 65                  70                  75                  80

Gly Thr Leu Ser Leu Ser Gln Arg Gln Leu Ser Glu Glu Glu Arg Gly
                 85                  90                  95

Arg Leu Arg Asp Val Ala Ala Leu Asn Gly Leu Tyr Arg Val Arg Val
            100                 105                 110

Pro Arg Arg Pro Gly Ala Pro Glu Gly Pro Ala Gly Gly Tyr Val
            115                 120                 125

Ser Ser Phe Val Pro Ala Cys Ser Leu Val Glu Ser His Leu Ser Asp
130                 135                 140

Gln Leu Thr Leu His Val Asp Val Val Gly Asn Val Val Gly Val Ser
145                 150                 155                 160

Val Val Thr Leu Pro Gly Gly Cys Arg Gly Tyr Glu Val Glu Asp Val
                165                 170                 175

Asp Leu Glu Leu Phe Asn Thr Thr Val Gln Leu Gln Pro Pro Thr Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
210                 215                 220

Lys Tyr Trp Met Tyr Ile Ile Pro Val Val Leu Phe Leu Met Met Ser
225                 230                 235                 240

Gly Ala Pro Asp Thr Gly Gly Gln Gly Gly Gly Gly Gly Gly Gly Gly
                245                 250                 255

Gly Gly Gly Ser Gly Arg
            260

<210> SEQ ID NO 32
<211> LENGTH: 263
<212> TYPE: PRT
<213> ORGANISM: Xenopus tropicalis

<400> SEQUENCE: 32

Met Ala Ala Gly Cys Leu Val Gly Gln Arg Ala Gly Pro Leu Ser Asp
 1               5                  10                  15

Lys Leu Ser Gly Tyr Cys Trp Val Leu Pro Leu Leu Leu Val Ala
                20                  25                  30

Thr Ala Gln Ala Ser Val Cys Arg Leu Lys Thr Gly Asp Gly Arg Asp
            35                  40                  45

Ser Glu Ser Cys Gly Thr Asn Leu Glu Leu Glu His Ser Phe Glu Leu
 50                  55                  60

Asp Asp Ser Ile His Phe Lys Lys Arg Gly Ser Leu Ile Trp Ser Gly
 65                  70                  75                  80

Thr Ala Glu Gln Ser Ile Ser Ile Leu Gln Lys Gln Leu Thr Glu Asp
                85                  90                  95

Glu Arg Asn Lys Leu Arg Asp Ile Ala Asn Leu Asn Gly Leu Tyr Arg
            100                 105                 110

Ile Arg Val Pro Arg Lys Leu Gly Ile Thr Glu Glu Ala Asn Glu Tyr
            115                 120                 125

Val Thr Ser Phe Val Arg Ala Cys Ser Met Val Glu Ser His Leu Ser
130                 135                 140

-continued

Asp Gln Ile Ser Val His Thr Asp Ile Ser Gly Asn Val Val Gly Ile
145                 150                 155                 160

Ser Ile Val Thr Phe Pro Gly Ser Cys Asn Gly Ala Glu Val Glu Asp
            165                 170                 175

Val Asp Leu Glu Met Phe Asn Thr Thr Val Tyr Ile Gln Gln Pro Ile
        180                 185                 190

Ala Ala Ala Val Pro Glu Thr Ala Ala Phe Ile Glu Arg Leu Glu Met
    195                 200                 205

Glu Gln Ala Gln Lys Ala Lys Asn Pro Gln Gln Lys Ser Phe Phe
210                 215                 220

Ala Lys Tyr Trp Met Tyr Ile Ile Pro Val Val Leu Phe Leu Met Met
225                 230                 235                 240

Ser Gly Ala Ser Asp Ala Gly Asn Gln Gly Gly Asn Gly Gly Gly
            245                 250                 255

Gly Gly Ser Gly Gly Gly Arg
        260

<210> SEQ ID NO 33
<211> LENGTH: 251
<212> TYPE: PRT
<213> ORGANISM: Danio rerio

<400> SEQUENCE: 33

Met Ala Pro Ile Arg Val Leu Ser Leu Val Leu Pro Ile Leu Ser Thr
1               5                   10                  15

Val Pro Leu Leu Leu Thr Gln Phe Gly Glu Cys Asn Asn Gly Arg Arg
            20                  25                  30

Ser Gly Asp Ala Val Asp Thr Asp Phe Ser Gly Phe Ser Val Pro Leu
        35                  40                  45

Glu His Ser Phe Glu Val Asp Asp Val Pro Arg Phe Arg Leu Arg Gly
    50                  55                  60

Ala Leu Gln Phe Arg Gly Gly Arg Glu Asn Ser Val Tyr Leu Ser Gln
65                  70                  75                  80

Asn Gln Leu Ser Glu Lys Asp Arg Asn Thr Leu Lys Asp Val Ala Ala
                85                  90                  95

Val Asp Gly Leu Tyr Arg Ile Arg Val Pro Arg Val Ser Leu Gln Val
            100                 105                 110

Asp Arg Gln Thr Glu Arg Gln Tyr Glu Gly Tyr Leu Thr Ala Phe Val
        115                 120                 125

Arg Ala Cys Ala Leu Val Glu Ser His Leu Ser Asp Val Ile Thr Leu
130                 135                 140

His Thr Asp Val Ser Gly Tyr Val Ile Gly Ile Ser Ile Val Thr Ile
145                 150                 155                 160

Pro Gly Ser Cys Arg Gly Ile Glu Val Glu Asp Glu Val Asp Leu Glu
                165                 170                 175

Val Phe Asn Thr Thr Ile Ser Val Met Ala Pro Val Thr Ala Pro Val
            180                 185                 190

Pro Glu Thr Ala Pro Tyr Ile Glu Arg Met Glu Met Glu Met Glu Lys
        195                 200                 205

Lys Gly Lys Asn Pro Gln Glu Gln Lys Ser Phe Phe Ala Lys Tyr Trp
210                 215                 220

Tyr Leu Ile Leu Gly Gly Ala Val Phe Leu Met Ala Thr Ser Ser Ala
225                 230                 235                 240

Gln Thr Pro Pro Gly Gly Ala Arg Glu Gln Ser
                245                 250

<210> SEQ ID NO 34
<211> LENGTH: 269
<212> TYPE: PRT
<213> ORGANISM: Homo sapiens

<400> SEQUENCE: 34

Met Ala Ala Ala Ser Ala Gly Ala Thr Arg Leu Leu Leu Leu Leu Leu
1               5                   10                  15

Met Ala Val Ala Ala Pro Ser Arg Ala Arg Gly Ser Gly Cys Arg Ala
            20                  25                  30

Gly Thr Gly Ala Arg Gly Ala Gly Ala Glu Gly Arg Glu Gly Glu Ala
        35                  40                  45

Cys Gly Thr Val Gly Leu Leu Leu Glu His Ser Phe Glu Ile Asp Asp
    50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
                85                  90                  95

Arg Leu Arg Asp Val Ala Ala Leu Asn Gly Leu Tyr Arg Val Arg Ile
            100                 105                 110

Pro Arg Arg Pro Gly Ala Leu Asp Gly Leu Glu Ala Gly Gly Tyr Val
        115                 120                 125

Ser Ser Phe Val Pro Ala Cys Ser Leu Val Glu Ser His Leu Ser Asp
    130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Thr Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
    210                 215                 220

Lys Tyr Trp Met Tyr Ile Ile Pro Val Val Leu Phe Leu Met Met Ser
225                 230                 235                 240

Gly Ala Pro Asp Thr Gly Gly Gln Gly Gly Gly Gly Gly Gly Gly Gly
                245                 250                 255

Gly Gly Gly Ser Gly Leu Cys Cys Val Pro Pro Ser Leu
            260                 265

<210> SEQ ID NO 35
<211> LENGTH: 31
<212> TYPE: PRT
<213> ORGANISM: Homo sapiens

<400> SEQUENCE: 35

Met Ala Ala Pro Ser Gly Gly Trp Asn Gly Val Gly Ala Ser Leu Trp
1               5                   10                  15

Ala Ala Leu Leu Leu Gly Ala Val Ala Leu Arg Pro Ala Glu Ala
            20                  25                  30

<210> SEQ ID NO 36
<211> LENGTH: 6
<212> TYPE: PRT
<213> ORGANISM: Artificial Sequence

```
<220> FEATURE:
<223> OTHER INFORMATION: Hexahistidin-tag for purification of proteins

<400> SEQUENCE: 36

His His His His His His
1               5

<210> SEQ ID NO 37
<211> LENGTH: 27
<212> TYPE: PRT
<213> ORGANISM: Homo sapiens

<400> SEQUENCE: 37

Met Ala Ala Ala Ser Ala Gly Ala Thr Arg Leu Leu Leu Leu Leu Leu
1               5                   10                  15

Met Ala Val Ala Ala Pro Ser Arg Ala Arg Gly
            20                  25

<210> SEQ ID NO 38
<211> LENGTH: 16
<212> TYPE: PRT
<213> ORGANISM: Homo sapiens

<400> SEQUENCE: 38

Cys Thr Ile Trp Arg Pro Gln Gly Lys Ser Tyr Leu Tyr Phe Thr Gln
1               5                   10                  15

<210> SEQ ID NO 39
<211> LENGTH: 16
<212> TYPE: PRT
<213> ORGANISM: Homo sapiens

<400> SEQUENCE: 39

Cys Glu Gln Ala Gln Lys Ala Lys Asn Pro Gln Glu Gln Lys Ser Phe
1               5                   10                  15
```

FACTOR 1 PROTEIN, FACTOR 2 PROTEIN AND INHIBITORS THEREOF FOR USE IN TREATING OR PREVENTING DISEASES

CROSS-REFERENCE TO RELATED APPLICATION

This application is a U.S. national phase of International Application No. PCT/EP2014/050788, filed on Jan. 16, 2014, which claims priority to European Patent Application No. 13151593.4, filed Jan. 17, 2013, both of which are incorporated by reference herein in their entireties.

TECHNICAL FIELD OF THE INVENTION

The present invention relates to proteins comprising amino acid sequences encoded by nucleic acids derived from the human chromosomal region C19Orf10 termed Factor 1 and/or C19Orf63 termed Factor 2 for use in enhancing proliferation and/or healing and/or inhibiting apoptosis of none-transformed tissue or none-transformed cells. Also provided are inhibitors of Factor 1 and Factor 2 for medical use, in particular for use in treating or preventing a disease in which angiogenesis contributes to disease development or progression.

BACKGROUND OF THE INVENTION

Acute myocardial infarction (AMI) is a leading cause of morbidity and mortality worldwide. In Germany alone the incidence is about 280.000 cases per year. The treatment of a patient who has an AMI comprises the opening of the occluded coronary artery by reperfusion therapy combined with the administration of thrombocyte aggregation inhibitors and coagulation inhibitors to prevent the reclosure of the vessel. Further the pulse and blood pressure can be lowered through administration of beta-blockers and ACE inhibitors. Also common is the use of statins for lowering of the cholesterol level. The medical approach for a direct repair of the heart muscle is currently limited to the experimental use of body's own bone marrow cells. There is a great need for drugs with a similar effect without the use of bone marrow cells.

The tissue necrosis sustained during AMI triggers a wound healing response that leads to a replacement of the necrotic area with granulation tissue and eventually a collagen-rich scar. Monocytes are recruited from the bone marrow into the infarcted myocardium and play important roles during wound healing after AMI. The monocyte response in the myocardium is temporally biphasic. Pro-inflammatory monocytes appear earlier and promote digestion of infarcted tissue and removal of necrotic debris, whereas reparative monocytes dominate later and propagate angiogenesis and repair. Cell surface expression of the chemokine receptor CXCR4 identifies a reparative monocyte subset in mice and humans. Pro-angiogenic and pro-healing effects of CXCR4+ myeloid cells are thought to be mediated via secreted proteins acting in a paracrine manner, but the identity of these Factors was largely unknown. Therefore, the inventors conducted a bioinformatic secretome analysis in human CXCR4+ bone marrow cells to identify novel secreted proteins controlling infarct healing and showing therapeutic potential after AMI.

These studies identified two different polypeptides exhibiting pro-angiogenic and/or cytoprotective effects which were named Factor 1 and Factor 2 proteins by the Inventors.

Both Factors were described in several scientific publications referring to a biological context which does not comprise the pro-angiogenic and/or cytoprotective effects of these Factors in non-transformed cells or non-transformed tissues. None of the studies discloses evidence for or even a hint at a function of these Factors or a significant correlation of one of the Factors with a disease or condition associated exclusively with non-transformed cells or non-transformed tissue.

The amino acid sequence of human Factor 1 is encoded in open reading frame 10 on human chromosome 19 (C19Orf10). The Protein was described in 2007 in a proteom-analysis of the so called fibroblast-like synoviocytes (FLS-cells) as a new secreted Factor in the synovium. A correlation between the secretion of the protein and inflammatory diseases of the joint has been supposed without any experimental or statistical evidence (Weiler et al., Arthritis Research and Therapy 2007, The identification and characterization of a novel protein, c19orf10, in the synovium). A corresponding patent application claims the protein as therapeutic agent for the treatment of joint and for the diagnosis of a tissue undergoing altered growth as well as monitoring changes in a tissue (US 2008/0004232 A1, Characterization of c19orf10, a novel synovial protein). Another scientific publication describes an enhanced expression of the protein in hepatocellar carcinoma cells (Sunagozaka et al., International Journal of Cancer, 2010, Identification of a secretory protein c19orf10 activated in hepatocellular carcinoma). Recombinant produced protein showed a proliferation enhancing effect on cultured hepatocellar carcinoma cells. It is noted that C19Orf10 has also been referred to as IL-25, IL-27 and IL-27W as it was originally considered an interleukin. However, the terms "IL-25" and "IL-27" have been used inconsistently in the art and have been used to designate a variety of different proteins. For example, US 2004/0185049 refers to a protein as IL-27 and discloses its use in modulating the immune response. This protein is structurally distinct from Factor 1 (compare Factor 1 amino acid sequence according to SEQ ID NO: 1 to the amino acid sequence of "IL-27" according to UniProt: Q8NEV9). Similarly, EP 2 130 547 A1 refers to a protein as IL-25 and discloses its use in treating inflammation. This protein has also been referred to in the art as IL-17E and is structurally distinct from Factor 1 (compare the amino acid sequence of Factor 1 according to SEQ ID NO: 1 to the amino acid sequence of "IL-25" according to UniProt: Q9H293).

The amino acid sequence of human Factor 2 is encoded in open reading frame 63 on human chromosome 19 (C19Orf63). The protein was described in 2009 as new secreted Factor INM02 (Wang et al., Journal of Endocrinology 2009, Molecular cloning of a novel secreted peptide, INM02, and regulation of its expression by glucose). The presence of the protein was shown in human serum with polyclonal antibodies. Further, a correlation between the expression of the protein in cultured MIN6 (beta-cells) as well as in isolated pancreatic rat islets and the glucose concentration in the medium was shown. An analysis of the correlation between diabetes and the expression of INM2 provided no significant results. A corresponding patent application claims the production of polyclonal antibodies against the protein and the use for the treatment of diabetes mellitus (CN 200910055490, Novel polyclonal antibody of secretive peptide INM02 and preparation method thereof).

Another scientific publication described the protein as a new secreted Factor hHSS1 (human Hematopoietic Signal peptide-containing Secreted 1) (Junes-Gill et al., J Neurooncol, 2011, hHSS1: a novel secreted factor and suppressor of glioma growth located at chromosome 19q13.33). The published data shows an expression of hHSS1 in stem cells of the hematopoietic system and suggest a function as tumor-suppressor in the genesis of particular brain tumors (gliomas). A corresponding patent application claims the use of hHSS1 in the treatment of brain tumors (WO2011/094446 A1, A method for treating brain cancer using a novel tumor suppressor gene and secreted factor).

SUMMARY OF THE INVENTION

The invention provides in a first aspect a protein comprising the amino acid sequence according to SEQ ID NO: 1 or a fragment or a variant thereof, which has at least 80% sequence identity to SEQ ID NO: 1 for use in enhancing proliferation and/or healing and/or inhibiting apoptosis of non-transformed tissue or non-transformed cells.

In a second aspect, the invention provides a protein comprising the amino acid sequence according to SEQ ID NO: 3 or a fragment or a variant thereof, which has at least 80% sequence identity to SEQ ID NO: 3 for use in enhancing proliferation and/or healing and/or inhibiting apoptosis of non-transformed tissue or non-transformed cells.

In a third aspect, the invention provides nucleic acids encoding the proteins according to the first and the second aspect for the use in enhancing proliferation and/or healing and/or inhibiting apoptosis of non-transformed tissue or non-transformed cells.

In a fourth aspect, the invention provides vectors comprising the nucleic acid of the third aspect for use in enhancing proliferation and/or healing and/or inhibiting apoptosis of non-transformed tissue or non-transformed cells.

In a fifth aspect, the invention provides pharmaceutical compositions comprising the protein of the first and/or the second aspect and/or the nucleic acid of the third aspect and/or the vector of the fourth aspect and optionally a suitable pharmaceutical excipient for the use in enhancing proliferation and/or healing and/or inhibiting apoptosis of non-transformed tissue or non-transformed cells.

In a sixth aspect, the invention provides inhibitors of Factor 1 and Factor 2, respectively for medical use, preferably in treating or preventing a disease in which angiogenesis contributes to disease development or progression.

In a seventh aspect the invention provides nucleic acids encoding such inhibitors for use in treating or preventing a disease in which angiogenesis contributes to disease development or progression.

In an eight aspect the invention provides vectors comprising nucleic acids of the seventh aspect encoding such inhibitors for use in treating or preventing a disease in which angiogenesis contributes to disease development or progression.

In a ninth aspect the invention provides pharmaceutical compositions comprising the inhibitors of the sixth aspect and/or the nucleic acid of the seventh aspect and/or the vector of the eight aspect and optionally a suitable pharmaceutical excipient in treating or preventing a disease in which angiogenesis contributes to disease development or progression. The above summary does not necessarily describe all aspects of the present invention.

BRIEF DESCRIPTION OF THE DRAWINGS

FIG. 6: Sequences homologues to the protein encoded by human C19Orf10 were searched with the BLASTP algorithm. From the identified sequences, examples from different vertebrate species mainly mammalian but also one example from amphibian, bird and fish were chosen. The selected amino acid sequences were aligned using the CLUSTALW2 algorithm. Identities among all aligned species are marked by "*", most highly conserved amino acid positions, i.e. which only show conservative substitutions are marked by ":", highly conserved amino acid positions are marked by ".".

FIG. 7: Sequences homologues to the protein encoded by human C19Orf10 were searched for with the BLASTP algorithm. From the identified sequences, examples from different vertebrate species mainly mammalian but also one example from amphibian, bird and fish were chosen. The selected mammalian amino acid sequences were aligned using the CLUSTALW2 algorithm. Identities among all aligned species are marked by "*", most highly conserved amino acid positions, i.e. which only show conservative substitutions are marked by ":", highly conserved amino acid positions are marked by ".".

FIG. 8: Sequences homologues to the protein encoded by human C19Orf63 splice variant HSS1 were searched for with the BLASTP algorithm. From the identified sequences, examples from different vertebrate species mainly mammalian but also one sequence from amphibian and fish were chosen. The selected amino acid sequences were aligned using the CLUSTALW2 algorithm. Identities among all aligned species are marked by "*", most highly conserved amino acid positions, i.e. which only show conservative substitutions are marked by ":", highly conserved amino acid positions are marked by ".".

FIG. 9: Sequences homologues to the protein encoded by human C19Orf63 splice variant HSS1 were searched for with the BLASTP algorithm. From the identified sequences, examples from different vertebrate species mainly mammalian but also one sequence from amphibian and fish species were chosen. The selected mammalian amino acid sequences were aligned using the CLUSTALW2 algorithm. Identities among all aligned species are marked by "*", most highly conserved amino acid positions, i.e. which only show conservative substitutions are marked by ":", highly conserved amino acid positions are marked by ".".

FIG. 10: Sequences homologues to the protein encoded by human C19Orf63 splice variant HSM1 were searched for with the BLASTP algorithm From the identified sequences, examples from different vertebrate species mainly mammalian but also one sequence from amphibian and fish were chosen. The selected amino acid sequences were aligned using the CLUSTALW2 algorithm. Identities among all aligned species are marked by "*", most highly conserved amino acid positions, i.e. which only show conservative substitutions are marked by ":", highly conserved amino acid positions are marked by ".".

FIG. 11: Sequences homologues to the protein encoded by human C19Orf63 splice variant HSM1 were searched for with the BLASTP algorithm From the identified sequences, examples from different vertebrate species mainly mammalian but also one sequence from amphibian and fish were chosen. The selected mammalian amino acid sequences were aligned using the CLUSTALW2 algorithm. Identities among all aligned species are marked by "*", most highly conserved amino acid positions, i.e. which only show conservative substitutions are marked by ":", highly conserved amino acid positions are marked by ".".

FIG. 12: Shows the effect of Factor 1 and 2 specific antibodies on proliferation of HCAECs stimulated with recombinant Factor 1 (panel A) and recombinant Factor 2 (panel B). Data are mean±SEM from 3-6 experiments. Panel A: #P<0.05, ##P<0.01 vs. unstimulated control (column on the left) *P<0.05, **P<0.01 vs. Factor 1 without antibody; Panel B: ##P<0.01 vs. unstimulated control (column on the far left) *P<0.05, **P<0.01 vs. Factor 2 without antibody.

DETAILED DESCRIPTION OF THE INVENTION

Figure 1:
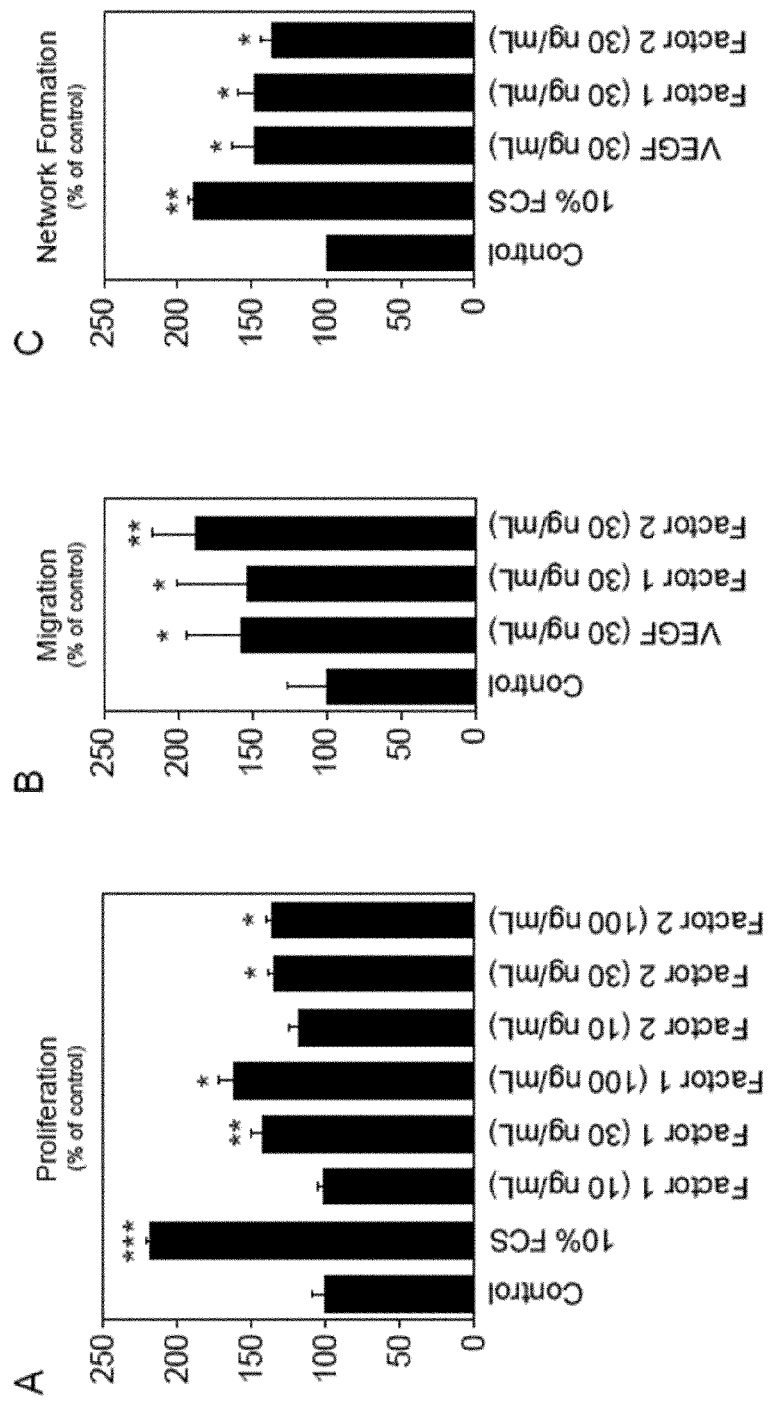
FIG. 1: Human coronary artery endothelial cells (HCAEC) and human umbilical vein endothelial cells (HUVEC) were cultured for 24 hours in minimal medium in the absence (control) or presence of 10% FCS, human recombinant VEGF-A (R&D Systems), or different concentrations of recombinant human Factor 1 (amino acid sequence according to SEQ ID NO: 2) or Factor 2 (amino acid sequence according to SEQ ID NO: 4), as indicated. (A) HCAEC proliferation was measured by bromodeoxyuridine incorporation. (B) HCAEC migration was assessed after wounding a confluent endothelial cell monolayer with a pipette tip. (C) HUVEC network formation was assessed in cells cultured on growth Factor-reduced Matrigel. N=3-5 independent experiments per condition; *P<0.05, P<0.01, *P<0.001 vs. control.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Definitions

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, cell biology, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989). Furthermore, conventional methods of clinical cardiology are employed which are also explained in the literature in the field (cf., e.g., *Braunwald's Heart Disease. A* Textbook of Cardiovascular Medicine, $9^{th}$ Edition, P. Libby et al. eds., Saunders Elsevier Philadelphia, 2011).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

Nucleic acid molecules are understood as polymeric macromolecules made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention referred to nucleic acid molecules include but are not limited to ribonucleic acid (RNA) and deoxyribonucleic acid (DNA). The terms "polynucleotide" and "nucleic acid" are used interchangeably herein.

The term "open reading frame" (ORF) refers to a sequence of nucleotides, that can be translated into amino acids. Typically, such an ORF contains a start codon, a subsequent region usually having a length which is a multiple of 3 nucleotides, but does not contain a stop codon (TAG, TAA, TGA, UAG, UAA, or UGA) in the given reading frame. Typically, ORFs occur naturally or are constructed artificially, i.e. by gene-technological means. An ORF codes for a protein where the amino acids into which it can be translated form a peptide-linked chain.

The terms "protein" and "polypeptide" are used interchangeably herein and refer to any peptide-bond-linked chain of amino acids, regardless of length or post-translational modification. Proteins usable in the present invention (including protein derivatives, protein variants, protein fragments, protein segments, protein epitops and protein domains) can be further modified by chemical modification. This means such a chemically modified polypeptide comprises other chemical groups than the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility. Chemical modifications applicable to the variants usable in the present invention include without limitation: PEGylation, glycosylation of non-glycosylated parent polypeptides, covalent coupling to therapeutic small molecules, like glucagon-like peptide 1 agonists, including exenatide, albiglutide, taspoglutide, DPP4 inhibitors, incretin and liraglutide, or the modification of the glycosylation pattern present in the parent polypeptide. Such chemical modifications applicable to the variants usable in the present invention may occur co- or post-translational.

The term "amino acid" encompasses naturally occurring amino acids as well as amino acid derivatives. A hydrophobic non-aromatic amino acid in the context of the present invention, is preferably any amino acid which has a Kyte-Doolittle hydropathy index of higher than 0.5, more preferably of higher than 1.0, even more preferably of higher than 1.5 and is not aromatic. Preferably, a hydrophobic non-aromatic amino acid in the context of the present invention, is selected from the group consisting of the amino acids alanine (Kyte Doolittle hydropathy index 1.8), methionine (Kyte Doolittle hydropathy index 1.9), isoleucine (Kyte Doolittle hydropathy index 4.5), leucine Kyte Doolittle hydropathy index 3.8), and valine (Kyte Doolittle hydropathy index 4.2), or derivatives thereof having a Kyte Doolittle hydropathy index as defined above.

The term "post-translational" used herein refers to events that occur after the translation of a nucleotide triplet into an amino acid and the formation of a peptide bond to the proceeding amino acid in the sequence. Such post-translational events may occur after the entire polypeptide was formed or already during the translation process on those parts of the polypeptide that have already been translated. Post-translational events typically alter or modify the chemical or structural properties of the resultant polypeptide. Examples of post-translational events include but are not limited to events such as glycosylation or phosphorylation of amino acids, or cleavage of the peptide chain, e.g. by an endopeptidase.

The term "co-translational" used herein refers to events that occur during the translation process of a nucleotide triplet into an amino acid chain. Those events typically alter or modify the chemical or structural properties of the resultant amino acid chain. Examples of co-translational events include but are not limited to events that may stop the translation process entirely or interrupted the peptide bond formation resulting in two discreet translation products.

The term "variant" is used herein to refer to a polypeptide which differs in comparison to the polypeptide or fragment thereof from which it is derived by one or more changes in the amino acid sequence. The polypeptide from which a protein variant is derived is also known as the parent polypeptide. Likewise, the fragment from which a protein fragment variant is derived from is known as the parent fragment. Typically, a variant is constructed artificially, preferably by gene-technological means. Typically, the parent polypeptide is a wild-type protein or wild-type protein domain. Further, the variants usable in the present invention may also be derived from homologs, orthologs, or paralogs of the parent polypeptide or from artificially constructed variant, provided that the variant exhibits at least one biological activity of the parent polypeptide. The changes in the amino acid sequence may be amino acid exchanges, insertions, deletions, N-terminal truncations, or C-terminal truncations, or any combination of these changes, which may occur at one or several sites. In preferred embodiments, a variant usable in the present invention exhibits a total number of up to 100 (up to 1, 2, 3, 4, 5, 6, 7, 8, 9, 10, 15, 20, 25, 30, 35, 40, 45, 50, 55, 60, 65, 70, 75, 80, 85, 90, 95, or 100) changes in the amino acid sequence (i.e. exchanges, insertions, deletions, N-terminal truncations, and/or C-terminal truncations). The amino acid exchanges may be conservative, and/or semi-conservative, and/or non-conservative. In preferred embodiments, a variant usable in the present invention differs from the protein or domain from which it is derived by up to 1, 2, 3, 4, 5, 6, 7, 8, 9, 10, 11, 12, 13, 14, 15, 16, 17, 18, 19, 20, 25, 30, 35, 40, 45, or 50, amino acid exchanges, preferably conservative amino acid changes.

Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino acid | Conservative substitution | Semi-conservative |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

Alternatively or additionally, a "variant" as used herein, can be characterized by a certain degree of sequence identity to the parent polypeptide or parent polynucleotide from which it is derived. More precisely, a protein variant in the context of the present invention exhibits at least 80% sequence identity to its parent polypeptide. Preferably, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide. Preferably, the polynucleotide in question and the reference polynucleotide exhibit the indicated sequence identity over a continuous stretch of 60, 90, 120, 135, 150, 180, 210, 240, 270, 300 or more nucleotides or over the entire length of the reference polypeptide.

The term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

Fragments of proteins comprise deletions of amino acids, which may be N-terminal truncations, C-terminal truncations or internal deletions or any combination of these. Such variants comprising N-terminal truncations, C-terminal truncations and/or internal deletions are referred to as "fragments" in the context of the present application. A fragment may be naturally occurring (e.g. splice variants) or it may be constructed artificially, preferably by gene-technological means. Preferably, a fragment (or deletion variant) has a deletion of up to 1, 2, 3, 4, 5, 6, 7, 8, 9, 10, 15, 20, 25, 30, 35, 40, 45 or 50 amino acids at its N-terminus and/or at its C-terminus and/or internally as compared to the parent polypeptide, preferably at its N-terminus, at its N- and C-terminus, or at its C-terminus.

In case where two sequences are compared and the reference sequence is not specified in comparison to which the sequence identity percentage is to be calculated, the sequence identity is to be calculated with reference to the longer of the two sequences to be compared, if not specifically indicated otherwise.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) or the CLUSTALW2 algorithm (Larkin M A, Blackshields G, Brown N P, Chenna R, McGettigan P A, McWilliam H, Valentin F, Wallace I M, Wilm A, Lopez R, Thompson J D, Gibson T J, Higgins D G. (2007). Clustal W and Clustal X version 2.0. Bioinformatics, 23, 2947-2948.) which are available e.g. on http://npsa-pbil.ibcp.fr/cgi-bin/npsa_automat.pl?page=/NPSA/npsa_clustalw.html or on http://www.ebi.ac.uk/Tools/clustalw2/index.html. Preferably, the CLUSTALW2 algorithm on http://www.ebi.ac.uk/Tools/clustalw2/index.html is used wherein the parameters used are the default parameters as they are set on http://www.ebi.ac.uk/Tools/clustalw2/index.html: Alignment type=Slow, protein weight matrix=Gonnet, gap open=10, gap extension=0, 1 for slow pairwise alignment options and protein weight matrix=Gonnet, gap open=10, gap extension=0, 20, gap distances=5, No end gaps=no, Output options: format=Aln w/numbers, Order=aligned.

The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST protein searches are performed with the BLASTP program available e.g. on http://blast.ncbi.nlm.nih.gov/
Blast.cgi?PROGRAM=blastp&BLAST_PROGRAMS=blastp&PAGE_TYPE=BlastSearch&SHOW_DEFAULTS=on&LINK_LOC=blasthome. Preferred algorithm parameters used are the default parameters as they are set on http://blast.ncbi.nlm.nih.gov/
Blast.cgi?PROGRAM=blastp&BLAST_PROGRAMS=blastp&PAGE_TYPE=BlastSearch&SHOW_DEFAULTS=on&LINK_LOC=blasthome: Expect threshold=10, word size=3, max matches in a query range=0, matrix=BLOSUM62, gap costs=Existence: 11 Extension: 1, compositional adjustments=conditional compositional score matrix adjustment together with the database of non-redundant protein sequences (nr) to obtain amino acid sequences homologous to the Factor 1 and Factor 2 polypeptides.

To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

The term "host cell" as used herein refers to a cell that harbours a nucleic acid of the invention (e.g. a plasmid or virus). Such host cell may either be a prokaryotic (e.g. a bacterial cell) or a eukaryotic cell (e.g. a fungal, plant or animal cell). The cell can be transformed or non-transformed. The cell can be an isolated cell for example in a cell culture or part of a tissue, which itself can be isolated or part of a more complex organization structure such as an organ or an individual.

The terms "Factor 1", "Factor 1 protein" or "Factor 1 polypeptide" are used interchangeably and refer to the protein indicated in NCBI reference sequence NM_019107.3 (human homologue) as well as it mammalian homologues, in particular from mouse or rat. The amino acid sequence of the human homologue is encoded in open reading frame 10 on human chromosome 19 (C19Orf10). Preferably, Factor 1 protein refers to a protein, which comprises, essentially consists or consists of a core segment of human Factor 1 having an amino acid sequence according to SEQ ID NO: 1. In a more preferred embodiment Factor 1 protein has the amino acid sequence according to SEQ ID NO: 2.

The terms "Factor 2", "Factor 2 protein" or "Factor 2 polypeptide" are used interchangeably and refer to the protein indicated in NCBI reference sequence NM_175063.4 (human homologue) as well as it mammalian homologues, in particular from mouse or rat. The amino acid sequence of human Factor 2 is encoded in open reading frame 63 on human chromosome 19 (C19Orf63). Preferably, Factor 2 protein refers to a protein, which comprises, essentially consists or consists of a core segment of human Factor 2 having an amino acid sequence according to SEQ ID NO: 3. In a more preferred embodiment Factor 2 protein has the amino acid sequence according to SEQ ID NO: 4 and 5, respectively. In the most preferred embodiment the Factor 2 protein is the secreted form, preferably having an amino acid sequence according to SEQ ID NO: 4.

The terms "non-transformed tissue" or "non-transformed cells" refers to tissue and cells which show the physiological parameters of a comparable non cancerous or tumorigenic cell or tissue. Such parameters are, for example but not limited to, cell cycle control, cell-division rate, contact inhibition, anchor-independent growth or metabolism. A comparable non cancerous or tumorigenic cell or tissue can be healthy, damaged or diseased.

The term "healing" comprises the regeneration and repair of living cells, tissue, organs and the biological system as a whole and the partial or complete resumption of normal functioning. In the case of tissue, organs or a biological system as a whole, it comprises the process by which the cells in the body regenerate and repair to reduce the size of a damaged or necrotic area and replace it with new living tissue. The replacement can happen, for example, by regeneration in which the necrotic cells are replaced by new cells that form similar tissue as was originally there; or by repair in which injured tissue is replaced with scar tissue. As the regeneration is the process which results in partial or complete resumption of normal functioning, it is the preferred variant in the healing process. Therefore, the term healing in the context of the invention comprises all processes, a person of skill in the art would combine with this term but preferably the regenerative processes should be promoted instead of the processes leading to the production of non functional tissue as for example scar tissue. The term healing in the context of the present invention is also preferably directed to the promotion of proliferation, migration, network formation and angiogenesis.

The term "enhancing proliferation" refers to an increase of the cell division rate of a cell or group of cells, if compared to cells or group of cells not treated with the proteins, nucleic acids, vectors or pharmaceutical compositions of the invention. It is well known in the art how to measure cell division rate of cells, e.g. by counting mitotic cells using FACS.

The term "inhibiting apoptosis" refers to the ability of proteins, nucleic acids, vectors or pharmaceutical compositions of the invention to prevent a cell or group of cells to enter apoptosis under conditions, in which control cells or groups of cells enter apoptosis. It is well known to the skilled person how to measure whether a cell undergoes apoptosis, e.g. by TUNEL assay.

The description of the embodiments comprises further definitions and explanations of terms used throughout the application. These descriptions and definitions are valid for the whole application unless it is otherwise stated.

Embodiments

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

In a first aspect, the invention provides a protein comprising, consisting essentially or consisting of a Factor 1 protein, preferably with the amino acid sequence according to SEQ ID NO: 1 or a fragment or a variant thereof, which has at least 80% sequence identity to SEQ ID NO: 1 for use in enhancing proliferation and/or healing and/or inhibiting apoptosis of non-transformed tissue or non-transformed cells, in particular enhancing proliferation of non-transformed tissue, enhancing proliferation of non-transformed cells, inhibiting apoptosis of non-transformed tissue or inhibiting apoptosis of non-transformed cells. In a particularly preferred embodiment of the invention, the protein comprises the amino acid sequence SEQ ID NO: 1 or a fragment thereof. Preferably, the protein has at least 85%, 90%, 91%, 92%, 93%, 94%, 95%, 96%, 97%, 98%, 99% identity to SEQ ID NO: 1.

In a preferred embodiment of this aspect of the invention, the protein comprises the amino acid sequence SEQ ID NO: 2, a fragment or a variant thereof, which has at least 80% sequence identity to SEQ ID NO: 2. Preferred fragments of SEQ ID NO: 2 lack the N-terminal signal sequence MAAPSGGWNGVGASLWAALLLGAVALRPAEA (SEQIDNO:35). A person skilled in the art is able to decide without undue burden, which positions in the parental polypeptide can be mutated to which extent and which positions have to be maintained to preserve the functionality of the polypeptide. Such information can, for example, be gained from homologues sequences which can be identified, aligned and analyzed by bioinformatic methods well known in the art. Such analyses are exemplarily described in example 7 and the results are shown in FIGS. 6 and 7. Mutations are preferably introduced in those regions of the protein, which are not fully conserved between species, preferably mammals, i.e. one or more of those amino acid positions are mutated that are not marked with "*". In a more preferred embodiment only amino acids are altered, which are neither fully conserved (indicated with "*") or conserved to a lesser extent (indicated with either ":" or "."). In a particularly preferred embodiment of the invention, a Factor 1 protein comprises, essentially consists or consists of the amino acid sequence SEQ ID NO: 2 or a fragment thereof. Preferably, the protein has at least 85%, 90%, 91%, 92%, 93%, 94%, 95%, 96%, 97%, 98%, 99% sequence identity to SEQ ID NO: 2.

Such mutations may be present in the full length protein according to SEQ ID NO: 2 or in the protein lacking the N-terminal signal sequence according to SEQ ID NO: 1.

N-terminal deletion variants in addition to the N-terminal signal may lack one or more amino acids from amino acid position 32 to 55 (based on SEQ ID NO: 2), i.e. from the N-terminally conserved region. Accordingly, the N-terminus of a deleted Factor 1 protein may be at position 32, 33, 34, 35, 36, 37, 38, 39, 40, 41, 42, 43, 44, 45, 46, 47, 48, 49, 50, 51, 52, 53, 54, 55, or 56 additionally, or alternatively the deleted Factor 1 protein may lack one or more of amino acid positions 146 to 173 (based on SEQ ID NO: 2, i.e. from the C-terminally conserved region. Accordingly, the C-terminus of a deleted Factor 1 protein may be at position 145, 146, 147, 148, 149, 150, 151, 152, 153, 154, 155, 156, 157, 158, 159, 160, 161, 162, 163, 164, 165, 166, 167, 168, 169, 170, 171, or 172.

The protein of the first aspect of the present invention may further comprise additional amino acid sequences, e.g. for stabilizing or purifying the resulting protein. Examples of such amino acids are $His_6$-tags (SEQ ID NO: 36), myc-tags, or FLAG-tags.

In some embodiments it is preferred to mutate protease cleavage sites within the protein of the first aspect of the present invention to stabilize the protein (see Segers et al. Circulation 2007, 2011). The skilled person knows how to determine potential proteolytic cleavage sites within a protein. For example, protein sequences can be submitted to websites providing such analysis as, e.g. http://web.expasy-.org/peptide_cutter/or http://pmap.burnham.org/proteases. If the protein sequence according to SEQ ID NO: 2 is submitted to http://web.expasy.org/peptide_cutter/the following cleavage sites with lower frequency (less then 10) are determined:

TABLE 1

| Protease | Frequency | Position (with reference to SEQ ID NO: 2) |
| --- | --- | --- |
| Arg-C proteinase | 7 | 27 43 96 113 130 151 170 |
| Asp-N endopeptidase | 4 | 40 58 85 132 |
| Clostripain | 7 | 27 43 96 113 130 151 170 |
| LysN | 9 | 59 99 108 124 136 144 155 160 166 |
| Proline-endopeptidase | 4 | 28 44 97 152 |

These sites may be altered to remove the recognition/cleavage sequence of the respectively identified protease to increase the serum half-life of the protein.

Factor 1 and Factor 2 have shown proliferation enhancing activity, in particular in enhancing angiogenesis. In a preferred embodiment, the protein according to the first aspect is used for enhancing the proliferation of non-transformed tissue or non-transformed cells, preferably angiogenesis. Accordingly, it is preferred that Factor 1 or Factor 2 are used to treat diseases, which can benefit from enhanced angiogenesis. Several examples of such diseases are further exemplified below.

Enhancing of proliferation involves in the context of the invention every grade of enhancement of proliferation of a cell or a tissue in comparison to a control cell or control tissue without administration of a protein of the invention. The proliferation of a cell can, for example, be measured through the incorporation of bromdeoxyuridine as described in example 2. The enhanced proliferation of a tissue can, for example, be determined by measuring the increase of weight or size of the respective tissue as well as with histological methods. Such methods are well known in the art as many of them are standard methods for clinical applications.

In another preferred embodiment, the protein according to the first aspect is used for the healing of non-transformed tissue or non-transformed cells. In another preferred embodiment, the protein according to the first aspect is used for the healing and enhancing of the proliferation of non-transformed tissue or non-transformed cells. In a particularly preferred embodiment, the protein according to the first aspect is used for the healing and enhancing of the proliferation and inhibiting apoptosis of non-transformed tissue or non-transformed cells.

In another preferred embodiment, the protein according to the first aspect is used for inhibiting apoptosis of non-transformed tissue or non-transformed cells. Thus, the protein of the present invention exhibits anti-apoptotic potential and protects the cells or tissue from apoptotic cell death. "Protecting" or "cytoprotective effect" in this context means that the extent of apoptotic cell death is reduced in the cells treated with the Factor 1 protein according to the present invention compared to a control by at least 20%, preferably by at least 30%, more preferably by at least 40%, and even more preferably by at least 50%, and most preferably by at least 60%. The skilled person is able to assess cell death, for example by in situ TdT-mediated dUTP nick end-labeling (TUNEL) as described in example 3. Other indicators for apoptosis are, for example, a fragmented genome which can be examined, e.g., by DNA laddering (Liu et al., 2005, Circulation 111:90-96), cytochrom-c release, or caspase 3 activity (Most et al., 2003, J. Biol. Chem. 278:48404-48412). The anti-apoptotic effect of a peptide may be assessed in vivo in an experimental heart failure animal model. For example, mice with postischemic contractile dysfunction may be treated with the protein and cardiac tissue of treated and control mice may be assessed for the extent of apoptotic cardiomyocytes. The peptide may be administered preferably parenterally, such as intraperitoneally, intravenously, or subcutaneously. In a particularly preferred embodiment, a protein of the present invention exhibits two and preferably all of the above functions, i.e., enhancing proliferation and healing and inhibiting apoptosis of non-transformed tissue or non-transformed cells. The fragments and variants of the Factor 1 protein included in this invention exhibit anti-apoptotic potential and protect the cells or tissue from apoptotic cell death that is at least 50%, preferably 60%, preferably 70%, preferably 80%, preferably 90% and more preferably at least 100% of that of a protein with the amino acid sequence according to SEQ ID NO: 1 or SEQ ID NO: 2, more preferably of SEQ ID NO: 1.

In a second aspect, the invention provides a protein comprising, consisting essentially of or consisting of a Factor 2 protein, with the amino acid sequence according to SEQ ID NO: 3 or a fragment or a variant thereof, which has at least 80% sequence identity to SEQ ID NO: 3 for use in enhancing proliferation and/or healing of non-transformed tissue or non-transformed cells. In a preferred embodiment of the invention, a Factor 2 protein comprises the amino acid sequence SEQ ID NO: 3, a fragment or a variant thereof, which has at least 80% identity to SEQ ID NO: 3. A person skilled in the art is able to decide without undue burden, which positions in the polypeptide can be mutated to what extent and which positions have to be maintained to preserve the functionality of the polypeptide. Such information can, for example, be gained from homologues sequences which can be identified, aligned and analyzed by bioinformatic methods well known in the art. In a particularly preferred embodiment of the invention, a protein of the second aspect of the invention comprises the amino acid sequence SEQ ID NO: 3 or a fragment thereof. Preferably, the protein has at least 85%, 90%, 91%, 92%, 93%, 94%, 95%, 96%, 97%, 98%, 99% sequence identity to SEQ ID NO: 3.

The protein of the second aspect of the present invention may further comprise additional amino acid sequences, e.g. for stabilizing or purifying the resulting protein.

In some embodiments it is preferred to mutate protease cleavage sites within the protein of the first aspect of the present invention to stabilize the protein. Suitable proteolytic cleavage sites can be identified as described above.

In another preferred embodiment of the invention, a protein of the second aspect of the invention comprises, essentially consists of or consists of the amino acid sequence SEQ ID NO: 4, a fragment or a variant thereof, which has at least 80% identity to SEQ ID NO: 4. Preferred fragments lack the N-terminal signal sequence MAAASAGATRLLLLLLMAVAAPSRARG' (SEQIDNO:37). A person skilled in the art is able to decide without undue burden, which positions in the polypeptide can be mutated to what extent and which positions have to be maintained to preserve the functionality of the polypeptide. Such information can, for example, be gained from homologues sequences which can be identified, aligned and analyzed by bioinformatic methods well known in the art. Such analyses are exemplarily described in example 8 and the results are shown in FIGS. 8 and 9. Mutations are preferably introduced only in those regions of the protein, which are not fully conserved between species, preferably mammals, i.e. one or more of those amino acid positions are mutated that are not marked with "*". In a more preferred embodiment only amino acids are altered, which are neither fully conserved (indicated with "*") or conserved to a lesser extent (indicated with either ":" or "."). In a particularly preferred embodiment of the invention, a Factor 2 protein comprises the amino acid sequence SEQ ID NO: 4 or a fragment thereof. Preferably, the protein has at least 85%, 90%, 91%, 92%, 93%, 94%, 95%, 96%, 97%, 98%, 99% identity to SEQ ID NO: 4.

Such mutations may be present in the full length protein according to SEQ ID NO: 4 or in the protein lacking the N-terminal signal sequence.

N-terminal deletion variants in addition to the N-terminal signal may lack one or more amino acids from amino acid position 27 to 73 (based on SEQ ID NO: 4), i.e. from the N-terminally conserved region. Accordingly, the N-terminus of a deleted Factor 2 protein may be at position 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 additionally, or alternatively the deleted Factor 1 protein may lack one or more from amino acid positions 190 to 254 (based on SEQ ID NO: 4, i.e. from the C-terminally conserved region. Accordingly, the C-terminus of a deleted Factor 2 protein may be at position 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, or 253.

In another preferred embodiment of the invention, a protein of the second aspect of the invention comprises, essentially consists of or consists of the amino acid sequence of SEQ ID NO: 5, a fragment or a variant thereof, which has at least 80% identity to SEQ ID NO: 5. Preferred fragments lack the N-terminal signal sequence MAAASAGATRLLLLLLMAVAAPSRARG (SEQIDNO:37). A person skilled in the art is able to decide without undue burden, which positions in the polypeptide can be mutated to what extent and which positions have to be maintained to preserve the functionality of the polypeptide. Such information can, for example, be gained from homologues sequences which can be identified, aligned and analyzed by bioinformatic methods well known in the art. Such analyses are exemplarily described in example 9 and the results are shown in FIGS. 10 and 11. Mutations are preferably introduced only in those regions of the protein, which are not fully conserved between species, preferably mammals, i.e. one or more of those amino acid positions are mutated that are not marked with "*". In a more preferred embodiment only amino acids are altered, which are neither fully conserved (indicated with "*") or conserved to a lesser extent (indicated with either ":" or "."). In a particularly preferred embodiment of the invention, a Factor 2 protein comprises the amino acid sequence SEQ ID NO: 5 or a fragment thereof. Preferably, the protein has at least 85%, 90%, 91%, 92%, 93%, 94%, 95%, 96%, 97%, 98%, 99% identity to SEQ ID NO: 5.

Such mutations may be present in the full length protein according to SEQ ID NO: 5 or in the protein according to SEQ ID NO: 5 lacking the N-terminal signal sequence.

N-terminal deletion variants in addition to the N-terminal signal may lack one or more amino acids from amino acid position 27 to 73 (based on SEQ ID NO: 4), i.e. from the N-terminally conserved region. Accordingly, the N-terminus of a deleted Factor 2 protein may be at position 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 additionally, or alternatively the deleted Factor 1 protein may lack one or more from amino acid positions 190 to 262 (based on SEQ ID NO: 4, i.e. from the C-terminally conserved region. Accordingly, the C-terminus of a deleted Factor 2 protein may be at position 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, or 261.

The fragments and variants of the protein of the second aspect of the invention exhibit anti-apoptotic potential and protect the cells or tissue from apoptotic cell death that is at least 50%, preferably 60%, preferably 70%, preferably 80%, preferably 90% and more preferably at least 100% of that of a protein with the amino acid sequence according to SEQ ID NO: 3, SEQ ID NO: 4 or SEQ ID NO: 5, most preferably SEQ ID NO: 3.

In a preferred embodiment, the protein according to the second aspect is used for enhancing the proliferation of non-transformed tissue or non-transformed cells. Enhancing of proliferation involves every grade of enhancement in comparison to a control cell or tissue without administration of a protein. The experimental methods for the measurement of proliferation are described above. A respective proliferation measurement for a protein according to the second aspect of the invention assessed by incorporation of bromdeoxyuridine what is also described in example 2.

In another preferred embodiment, the protein according to the second aspect is used for the healing of non-transformed tissue or non-transformed cells. In a particularly preferred embodiment, a protein according to the second aspect of the invention exhibits both of the above functions, i.e., enhancing proliferation and healing of non-transformed tissue or non-transformed cells.

In another embodiment of the invention, the proteins of aspects one and/or two are administered in vivo, ex vivo or in vitro, preferably in vivo. An exemplary embodiment, where a protein of the first aspect of the invention and/or a protein of the second aspect of the invention is administered ex vivo or in vitro is the enhancement of proliferation and/or healing and/or inhibiting apoptosis for the purpose of tissue engineering wherein a tissue is produced for the transplantation into an individual. The cells which are used for the tissue engineering can be derived from the same individual but also from another individual of the same species or of another species. The process of removing said cells or tissue and the transplantation of the new tissue into an individual is not comprised by the invention.

In a preferred embodiment of the invention, the non-transformed cells are stem cells. Such stem cells can be embryonic stem cells or adult stem cells as well as progenitor cells. The invention comprises omnipotent stem cells as well as pluripotent stem cells.

In a preferred embodiment, the non-transformed cells or the non-transformed tissue are diseased. In another preferred embodiment, the non-transformed cells or the non-transformed tissue are damaged. In another preferred embodiment, the non-transformed cells or the non-transformed tissue are damaged and diseased.

In a preferred embodiment, the non-transformed cells or the non-transformed tissue are muscle cells or muscle tissue. Muscle comprises all types of muscle known by a person of skill in the art. Such muscles are, for example, skeletal, smooth or cardiac muscle. In a more particular preferred embodiment, the muscle is a cardiac muscle. In another preferred embodiment, the non-transformed cells or the non-transformed tissue are epithelial cells or epithelial tissue. In another preferred embodiment, the non-transformed cells or the non-transformed tissue are nervous cells or nervous tissue.

In a preferred embodiment, the non-transformed cells or the non-transformed tissue belong to the circulatory system of an individual.

In another preferred embodiment, the non-transformed cells or the non-transformed tissue belong to or are derived from a defined system of the body of an individual selected from the group comprising the: digestive, endocrine, excretory, immune, integumentary, muscular, nervous, reproductive, respiratory or skeletal system. In another preferred embodiment of the invention, the cells belong to two, three, four, five, six, seven, eight, nine, ten or to all of the listed systems of an individual.

In another preferred embodiment, the non-transformed cells or the non-transformed tissue belong to or are derived from a defined part or organ of the body of an individual selected from the group comprising: skin, bone, heart, cartilage, vessel, oesophagus, stomach, intestine, gland, liver, kidney, lung, brain, and spleen. In a particularly preferred embodiment, the non-transformed cells or the non-transformed tissue belong to or are derived from the heart.

It is further preferred, that in case of a damaged non-transformed cell or of non-transformed tissue, the damage is caused through a genetic/inherited disease or an acquired disease resulting for example from ischemia, reperfusion injury, inflammation, infection, trauma, mechanical overload, intoxication or surgery. In a particularly preferred embodiment, the damage is caused through ischemia. In another particularly preferred embodiment, the damage is caused through a reperfusion injury.

In the context of the present invention, it is preferred that in case of a diseased or a damaged cell or tissue, wherein the damage is caused through a disease which is associated with atrophy, hypoplasy, inflammation, injury, or wounding. It is particularly preferred that the disease is associated with injury. It is also particularly preferred that the disease is associated with wounding.

In a preferred embodiment of the present invention, the disease is a skeletal muscle disorder selected from the group consisting of muscular dystrophy, muscle weakness, muscular atrophy, myositis, central core disease, nemaline (rod) myopathy, centronuclear myopathy, myotubular myopathy, centronuclear myotubular myopathy, ophthalmoplegia of the eye, and mitochondrial myopathy. The muscular dystrophy may be selected from the group consisting of Becker's muscular dystrophy, congenital muscular dystrophy, Duchenne muscular dystrophy, distal muscular dystrophy, Emery-Dreifuss muscular dystrophy, facioscapulohumeral muscular dystrophy, Limb-girdle muscular dystrophy, myotonic muscular dystrophy, and oculopharyngeal muscular dystrophy. The myositis may be selected from the group consisting of myositis ossificans, fibromyositis, idiopathic inflammatory myopathies (such as dermatomyositis, polymyositis, and inclusion body myositis), and pyomyositis.

In another preferred embodiment of the invention, the disease is primary or acquired cardiomyopathy. The primary cardiomyopathy is selected from inherited cardiomyopathy and cardiomyopathy caused by spontaneous mutations. Cardiomyopathies are for example but not limited to Hypertrophic cardiomyopathy (HCM or HOCM), Arrhythmogenic right ventricular cardiomyopathy (ARVC), Isolated ventricular non-compaction Mitochondrial myopathy, Dilated cardiomyopathy (DCM), Restrictive cardiomyopathy (RCM), Takotsubo cardiomyopathy, Loeffler endocarditis, diabetic cardiomyopathy, Alcoholic cardiomyopathy, Obesity-associated cardiomyopathy.

In the context of the invention, the acquired cardiomypathy is preferably selected from ischemic cardiomyopathy caused by atherosclerotic or other coronary artery diseases, cardiomyopathy caused by infection or intoxication of the myocardium, hypertensive heart disease caused by pulmonary arterial hypertension and/or arterial hypertension and diseases of the heart valves, wherein the ischemic cardiomyopathy caused by atherosclerotic or other coronary artery diseases is particularly preferred.

In a most preferred embodiment of the invention, the non-transformed cells or the non-transformed tissue which is damaged through ischemia or reperfusion injury belong to the heart. Accordingly, it is preferred that the resulting disease to be treated is selected from the group consisting of myocardial infarction, angina pectoris and heart failure, wherein the myocardial infarction is particularly preferred. The term "myocardial infarction" as used in the context of the invention comprises the acute myocardial infarction (AMI).

In a particularly preferred embodiment the use of the protein according to the first aspect of the invention or the protein according to the second aspect of the invention, comprises the application to an individual after myocardial infarction and the healing comprises the improvement of left ventricular systolic function and may be associated with an increase in capillary density in the infarct border zone. Additionally, the protein according to the first aspect of the invention or the protein according to the second aspect of the invention may reduce the mortality after a myocardial infarction. The methods which can be used to determine parameters like the improvement of left ventricular systolic function, increase in capillary density in the infarct border zone and the reduction of mortality after a myocardial infarction are well known in the art and exemplarily described in examples 4-6.

The Factor 1 and Factor 2 proteins, fragments, or variants described above are used in treating or ameliorating atrophy; hypoplasy; inflammation, injury; wounding, ischemia; reperfusion injury; inflammation; infection; trauma; mechanical overload; intoxication; primary or acquired cardiomyopathy, preferably inherited cardiomyopathy and cardiomyopathy caused by spontaneous mutations. Cardiomyopathies are for example but not limited to Hypertrophic cardiomyopathy (HCM or HOCM), Arrhythmogenic right ventricular cardiomyopathy (ARVC), Isolated ventricular non-compaction Mitochondrial myopathy, Dilated cardiomyopathy (DCM), Restrictive cardiomyopathy (RCM), Takotsubo cardiomyopathy, Loeffler endocarditis, diabetic cardiomyopathy, Alcoholic cardiomyopathy, or Obesity-associated cardiomyopathy; myocardial infarction or in improving left ventricular systolic function.

The Factor 1 and Factor 2 proteins, fragments, or variants described above may also be used in methods of treating the respectively indicated conditions and diseases.

In a third aspect the invention provides nucleic acids encoding the proteins according to the first and the second aspect for the use in enhancing proliferation and/or healing and/or inhibiting apoptosis of non-transformed tissue or non-transformed cells.

The terms "enhancing proliferation and/or healing and/or inhibiting apoptosis of non-transformed tissue or non-transformed cells" have the meaning and preferred meanings defined above.

Nucleic acid sequences can be optimized in an effort to enhance expression in a host cell. Parameters to be considered include C:G content, preferred codons, and the avoidance of inhibitory secondary structure. These Factors can be combined in different ways in an attempt to obtain nucleic acid sequences having enhanced expression in a particular host (cf. e.g. Donnelly et al., International Publication Number WO 97/47358). The ability of a particular sequence to have enhanced expression in a particular host involves some empirical experimentation. Such experimentation involves measuring expression of a prospective nucleic acid sequence and, if needed, altering the sequence. Starting with a particular amino acid sequence and the known degeneracy of the genetic code, a large number of different encoding nucleic acid sequences can be obtained. The degeneracy of the genetic code arises because almost all amino acids are encoded by different combinations of nucleotide triplets or "codons". The translation of a particular codon into a particular amino acid is well known in the art (see, e.g., Lewin GENES IV, p. 119, Oxford University Press, 1990).

In a preferred embodiment of the invention, the nucleic acid further comprises a transcriptional control element or expression control sequences positioned to control expression of the protein. Such a nucleic acid together with control elements is often termed as an expression system. The term "expression system" as used herein refers to a system designed to produce one or more gene products of interest. Typically, such system is designed "artificially", i.e. by gene-technological means usable to produce the gene product of interest in vivo, in vitro or ex vivo. The term "expression system" further encompasses the expression of the gene product of interest comprising the transcription of the polynucleotides, mRNA splicing, translation into a polypeptide, co- and post-translational modification of a polypeptide or protein as well as the targeting of the protein to one or more compartments inside of the cell, the secretion from the cell and the uptake of the protein in the same or another cell. This general description refers to expression systems for the use in eukaryotic cells, tissues or organisms. Expression systems for prokaryotic systems may differ, wherein it is well known in the art, how an expression system for prokaryotic cells is constructed.

Regulatory elements present in a gene expression cassette generally include: (a) a promoter transcriptionally coupled to a nucleotide sequence encoding the polypeptide, (b) a 5' ribosome binding site functionally coupled to the nucleotide sequence, (c) a terminator joined to the 3' end of the nucleotide sequence, and (d) a 3' polyadenylation signal functionally coupled to the nucleotide sequence. Additional regulatory elements useful for enhancing or regulating gene expression or polypeptide processing may also be present. Promoters are genetic elements that are recognized by an RNA polymerase and mediate transcription of downstream regions. Preferred promoters are strong promoters that provide for increased levels of transcription. Examples of strong promoters are the immediate early human cytomegalovirus promoter (CMV), and CMV with intron A (Chapman et al, Nucl. Acids Res. 19:3979-3986, 1991). Additional examples of promoters include naturally occurring promoters such as the EF1 alpha promoter, the murine CMV promoter, Rous sarcoma virus promoter, and SV40 early/late promoters and the [beta]-actin promoter; and artificial promoters such as a synthetic muscle specific promoter and a chimeric muscle-specific/CMV promoter (Li et al., Nat. Biotechnol. 17:241-245, 1999, Hagstrom et al., Blood 95:2536-2542, 2000).

The ribosome binding site is located at or near the initiation codon. Examples of preferred ribosome binding sites include CCACCAUGG, CCGCCAUGG, and ACCAUGG, where AUG is the initiation codon (Kozak, Cell 44:283-292, 1986). The polyadenylation signal is responsible for cleaving the transcribed RNA and the addition of a poly (A) tail to the RNA. The polyadenylation signal in higher eukaryotes contains an AAUAAA sequence about 11-30 nucleotides from the polyadenylation addition site. The AAUAAA sequence is involved in signalling RNA cleavage (Lewin, Genes IV, Oxford University Press, NY, 1990). The poly (A) tail is important for the processing, export from the nucleus, translation and stability of the mRNA.

Polyadenylation signals that can be used as part of a gene expression cassette include the minimal rabbit [beta]-globin polyadenylation signal and the bovine growth hormone polyadenylation (BGH) (Xu et al., Gene 272:149-156, 2001, Post et al., U.S. Pat. No. 5,122,458).

Examples of additional regulatory elements useful for enhancing or regulating gene expression or polypeptide processing that may be present include an enhancer, a leader sequence and an operator. An enhancer region increases transcription. Examples of enhancer regions include the CMV enhancer and the SV40 enhancer (Hitt et al., Methods in Molecular Genetics 7:13-30, 1995, Xu, et al., Gene 272:149-156, 2001). An enhancer region can be associated with a promoter.

The expression of the protein according to the second aspect of the invention or the protein according to the second aspect of the invention may be regulated. Such regulation can be accomplished in many steps of the gene expression. Possible regulation steps are, for example but not limited to, initiation of transcription, promoter clearance, elongation of transcription, splicing, export from the nucleus, mRNA stability, initiation of translation, translational efficiency, elongation of translation and protein folding. Other regulation steps, which influence the concentration of a Factor 1 or Factor 2 polypeptide inside a cell affect the half-life of the protein. Such a regulation step is, for example, the regulated degeneration of proteins. As the proteins of the invention comprise secreted proteins, the protein can be directed to a secretory pathway of the host cell. The efficiency of secretion regulates together with the regulatory steps referring to the expression and protein stability the concentration of the respective protein outside of the cell. Outside of the cell can refer to, for example but not limited to, a culture medium, a tissue, intracellular matrix or space or a body fluid such as blood or lymph.

The control of the regulatory steps mentioned above can be, for example, cell-type or tissue-type independent or cell-type or tissue-type specific. In a particularly preferred embodiment of the invention, the control of the regulatory steps is cell-type or tissue-type specific. Such a cell-type or tissue-type specific regulation is preferably accomplished through the regulation steps referring to the transcription of a nucleic acid. This transcriptional regulation can be accomplished through the use of cell-type or tissue-type specific promoter sequences. The result of this cell-type or tissue-type specific regulation can have different grades of specificity. This means, that the expression of a respective polypeptide is enhanced in the respective cell or tissue in comparison to other cell- or tissue-type or that the expression is limited to the respective cell- or tissue-type. Cell- or tissue-type specific promoter sequences are well known in the art and available for a broad range of cell- or tissue-types.

In another preferred embodiment, the expression is not cell-type or tissue-type specific but depends from physiological conditions. Such conditions are for example an inflammation or a wound. Such a physiological condition-specific expression can also be accomplished through regulation at all above mentioned regulation steps. The preferred way of regulation for a physiological condition-specific expression is the transcriptional regulation. For this purpose a wound or inflammation specific promoter can be used. Respective promoters are, for example, natural occurring sequences, which can be, for example, derived from genes, which are specifically expressed during an immune reaction and/or the regeneration of wounded tissue. Another possibility is the use of artificial promoter sequences, which are, for example constructed through combination of two or more naturally occurring sequences. In another preferred embodiment, the regulation is cell-type or tissue-type specific and physiological condition-specific. In a particularly preferred embodiment, the expression is a heart specific expression. In another particularly embodiment, the expression is heart specific and wound specific.

Another possibility for a regulation of expression of the protein according to the second aspect of the invention or the protein according to the second aspect of the invention is the conditional regulation of the gene expression. To accomplish conditional regulation, an operator sequence can be used. For example, the Tet operator sequence can be used to repress gene expression. The conditional regulation of gene expression by means of the Tet operator together with a Tet repressor is well known in the art and many respective systems have been established for a broad range of prokaryotic and eukaryotic organisms. A person of skill in the art knows how to choose a suitable system and adapt it to the special needs of the respective application.

In a particularly preferred embodiment the use of a nucleic acid according to the invention comprises the application to an individual after myocardial infarction and the healing comprises the improvement of left ventricular systolic function and may be associated with an increase in capillary density in the infarct border zone. Additionally, it may reduce the mortality after a myocardial infarction. The methods which can be used to determine parameters like the improvement of left ventricular systolic function, increase in capillary density in the infarct border zone and the reduction of mortality after a myocardial infarction are well known in the art and exemplarily described in examples 4-6.

Nucleic acids encoding the Factor 1 and Factor 2 proteins, fragments, or variants described above are preferably used in treating or ameliorating atrophy; hypoplasy; inflammation, injury; wounding, ischemia; reperfusion injury; inflammation; infection; trauma; mechanical overload; intoxication; primary or acquired cardiomyopathy, preferably inherited cardiomyopathy and cardiomyopathy caused by spontaneous mutations. Cardiomyopathies are for example but not limited to Hypertrophic cardiomyopathy (HCM or HOCM), Arrhythmogenic right ventricular cardiomyopathy (ARVC), Isolated ventricular non-compaction Mitochondrial myopathy, Dilated cardiomyopathy (DCM), Restrictive cardiomyopathy (RCM), Takotsubo cardiomyopathy, Loeffler endocarditis, diabetic cardiomyopathy, Alcoholic cardiomyopathy, or Obesity-associated cardiomyopathy; myocardial infarction or in improving left ventricular systolic function.

In a fourth aspect, the invention provides vectors comprising the nucleic acid or the expression system of the third aspect for use in enhancing proliferation and/or healing and/or inhibiting apoptosis of non-transformed tissue or non-transformed cells.

The terms "enhancing proliferation and/or healing and/or inhibiting apoptosis of non-transformed tissue or non-transformed cells" have the meaning and preferred meanings defined above.

As used herein, the term "vector" refers to a protein or a polynucleotide or a mixture thereof which is capable of being introduced or of introducing the proteins and/or nucleic acid comprised therein into a cell. In the context of the present invention it is preferred that the genes of interest encoded by the introduced polynucleotide are expressed within the host cell upon introduction of the vector or the vectors. Examples of suitable vectors include but are not limited to plasmid vectors, cosmid vectors, phage vectors such as lambda phage, filamentous phage vectors, viral vectors, viral like particles, and bacterial spores.

In a preferred embodiment of the invention, the vector is a viral vector. Suitable viral vectors include but are not limited to adenoviral vectors, adeno-associated viral (AAV) vectors, alphaviral vectors, herpes viral vectors, measles viral vectors, pox viral vectors, vesicular stomatitis viral vectors, retroviral vector and lentiviral vectors.

In a particularly preferred embodiment of the invention, the vector is an adenoviral or an adeno-associated viral (AAV) vector.

Nucleic acid encoding one or more proteins of the first aspect of the invention and/or one or more proteins of the second aspect of the invention can be introduced into a host cell, a tissue or an individual using vectors suitable for therapeutic administration. Suitable vectors can preferably deliver nucleic acids into a target cell without causing an unacceptable side effect.

In a particularly preferred embodiment the use of a vector according to the invention, comprises the application to an individual after myocardial infarction and the healing comprises the improvement of left ventricular systolic function and may be associated with an increase in capillary density in the infarct border zone. Additionally, it may reduce the mortality after a myocardial infarction. The methods which can be used to determine parameters like the improvement of left ventricular systolic function, increase in capillary density in the infarct border zone and the reduction of mortality after a myocardial infarction are well known in the art and exemplarily described in examples 4-6.

Vectors comprising nucleic acids encoding the Factor 1 and Factor 2 proteins, fragments, or variants described above are preferably used in treating or ameliorating atrophy; hypoplasy; inflammation, injury; wounding, ischemia; reperfusion injury; inflammation; infection; trauma; mechanical overload; intoxication; primary or acquired cardiomyopathy, preferably inherited cardiomyopathy and cardiomyopathy caused by spontaneous mutations. Cardiomyopathies are for example but not limited to Hypertrophic cardiomyopathy (HCM or HOCM), Arrhythmogenic right ventricular cardiomyopathy (ARVC), Isolated ventricular non-compaction Mitochondrial myopathy, Dilated cardiomyopathy (DCM), Restrictive cardiomyopathy (RCM), Takotsubo cardiomyopathy, Loeffler endocarditis, diabetic cardiomyopathy, Alcoholic cardiomyopathy, or Obesity-associated cardiomyopathy; myocardial infarction or in improving left ventricular systolic function.

In a fifth aspect, the invention provides pharmaceutical compositions comprising the protein of the first and/or the second aspect and/or the nucleic acid of the third aspect and/or the vector of the fourth aspect and optionally a carrier, for use in enhancing proliferation and/or healing and/or inhibiting apoptosis of non-transformed tissue or non-transformed cells.

The terms "enhancing proliferation and/or healing and/or inhibiting apoptosis of non-transformed tissue or non-transformed cells" have the meaning and preferred meanings defined above.

The term "carrier", as used herein, refers to a pharmacologically inactive substance such as but not limited to a diluent, excipient, surfactants, stabilizers, physiological buffer solutions or vehicles with which the therapeutically active ingredient is administered. Such pharmaceutical carriers can be liquid or solid. Liquid carrier include but are not limited to sterile liquids, such as saline solutions in water and oils, including but not limited to those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin. In a preferred embodiment of the invention, the carrier is a suitable pharmaceutical excipient. Suitable pharmaceutical "excipients" comprise starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. Such suitable pharmaceutical excipients are preferably pharmaceutically acceptable.

"Pharmaceutically acceptable" means approved by a regulatory agency of the Federal or a state government or listed in the U.S. Pharmacopeia or other generally recognized pharmacopeia for use in animals, and more particularly in humans.

The term "composition" is intended to include the formulation of the active compound with encapsulating material as a carrier providing a capsule in which the active component with or without other carriers, is surrounded by a carrier, which is thus in association with the active compound.

The term "active ingredient" refers to the substance in a pharmaceutical composition or formulation that is biologically active, i.e. that provides pharmaceutical value. In the context of the invention, the active ingredient is a protein of the first and/or the second aspect and/or a nucleic acid of the third aspect and/or a vector of the fourth aspect. A pharmaceutical composition may comprise one or more active ingredients which may act in conjunction with or independently of each other. The active ingredient can be formulated as neutral or salt forms. The salt form is preferably a pharmaceutically acceptable salt.

The term "pharmaceutically acceptable salt" refers to, for example but not limited to, a salt of the polypeptides of the present invention. Suitable pharmaceutically acceptable salts include acid addition salts which may, for example, be formed by mixing a solution of the polypeptide of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the peptide carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (cf. e.g. S. M. Berge et al., "Pharmaceutical Salts", J. Pharm. Sci., 66, pp. 1-19 (1977)).

The active ingredient is administered to a cell, a tissue or an individual in an effective amount. An "effective amount" is an amount of an active ingredient sufficient to achieve the intended purpose. The active ingredient may be a therapeutic agent. The effective amount of a given active ingredient will vary with parameters such as the nature of the ingredient, the route of administration, the size and species of the individual to receive the active ingredient, and the purpose of the administration. The effective amount in each individual case may be determined empirically by a skilled artisan according to established methods in the art. As used in the context of the invention, "administering" includes in vivo administration to an individual as well as administration directly to cells or tissue in vitro or ex vivo.

In a preferred embodiment of the invention, the pharmaceutical compositions are customized for the treatment of a disease or disorder. As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); (e) limiting or preventing recurrence of symptoms in patients that were previously symptomatic for the disorder(s); (f) reduction of mortality after occurrence of a disease or a disorder; (g) healing; and (h) prophylaxis of a disease. As used herein, "prevent", "preventing", "prevention", or "prophylaxis" of a disease or disorder means preventing that such disease or disorder occurs in patient.

In a particularly preferred embodiment of the invention, a treatment with a pharmaceutical composition according to the invention the healing comprises the treatment of an individual after myocardial infarction and the healing comprises the improvement of left ventricular systolic function and may be associated with an increase in capillary density in the infarct border zone. Additionally, it may reduce the mortality after a myocardial infarction. The methods which can be used to determine parameters like the improvement of left ventricular systolic function, increase in capillary density in the infarct border zone and the reduction of mortality after a myocardial infarction are well known in the art and exemplarily described in examples 4-6.

The pharmaceutical composition contemplated by the present invention may be formulated in various ways well known to one of skill in the art. For example, the pharmaceutical composition of the present invention may be in liquid form such as in the form of solutions, emulsions, or suspensions. Preferably, the pharmaceutical composition of the present invention is formulated for parenteral administration, preferably for intravenous, intraarterial, intramuscular, subcutaneous, transdermal, intrapulmonary, intraperitoneal intracoronary, intracardiac administration, or administration via mucous membranes, preferably for intravenous, subcutaneous, or intraperitoneal administration. A preparation for oral or anal administration is also possible. Preferably, the pharmaceutical composition of the present invention is in the form of a sterile aqueous solution which may contain other substances, for example, enough salts or glucose to make the solution isotonic with blood. The aqueous solutions should be suitably buffered (preferably to a pH of from 3 to 9, more preferably to a pH of from 5 to 7), if necessary. The pharmaceutical composition is preferably in unit dosage form. In such form the pharmaceutical composition is subdivided into unit doses containing appropriate quantities of the active component. The unit dosage form can be a packaged preparation, the package containing discrete quantities of pharmaceutical composition such as vials or ampoules.

The administration of the pharmaceutical composition is preferably administered through the intravenous, intraarterial, intramusculuar, subcutaneous, transdermal, intrapulmonary, intraperitoneal, intracoronary or intracardiac route wherein other routes of administration known in the art are also comprised.

In the case, the pharmaceutical composition is used as a treatment for an individual, the use of the pharmaceutical composition can replace the standard treatment for the respective disease or condition or can be administered additionally to the standard treatment. In the case of an additionally use of the pharmaceutical composition, the pharmaceutical composition can be administered before, simultaneously or after a standard therapy. In a preferred embodiment, the standard therapy is a reperfusion therapy and the pharmaceutical composition can be administered before, simultaneously or after the reperfusion therapy.

It is further preferred that the pharmaceutical composition is administered once or more than once. This comprises 2, 3, 4, 5, 6, 7, 8, 9, 10, 11, 12, 13, 14, 15, 16, 17, 18, 19, 20, 25, 30, 35, 40, 45 or 50 times. The time span for the administration of the pharmaceutical is not limited. Preferably, the administration does not exceed 1, 2, 3, 4, 5, 6, 7 or 8 weeks.

A single dose of the pharmaceutical composition, can independently from the overall amount of administered doses or the respective time span of administration be administered as one or more bolus injection(s) and/or infusion(s).

The first through fifth aspect of the present invention is based on the observation of the present inventors that Factor 1 and Factor 2 are potent pro-angiogenic molecules in vitro and in vivo. Accordingly, the proteins, nucleic acids and vectors described above are also contemplated for ex vivo use, which may be therapeutic, e.g. for ex vivo stimulation of the cells indicated above or for use in cell culture applications.

However, the observation of the pro-angiogenic activity of Factor 1 and 2 led the present inventors to investigate whether Factor 1 and Factor 2, respectively are targets for anti-angiogenic therapy. The inventors were successful in proving that inhibition of Factor 1 or inhibition of Factor 2 can be used to inhibit angiogenesis.

Anti-angiogenic strategies are used to treat cancerous conditions and other disorders, such as age-related macular degeneration, where angiogenesis contributes to disease progression (see, e.g. Ferrara N and Kerbel R S (2005) Nature: 438:967-974 or Potente M, et al. (2011) Cell. 146(6):873-887). Accordingly, in further aspects the present invention relates to the anti-angiogenic properties of inhibitors of Factor 1 and Factor 2. In these aspects the definitions provided above in the definition section equally apply. Additionally, specific definitions provided in the description of the first to fifth aspect as well as preferred embodiments, e.g. of the term "vector" and of preferred vectors also apply to the following aspects of the invention unless the context of its use clearly indicates otherwise.

In a sixth aspect the present invention provides an inhibitor of Factor 1 and/or 2 protein for medical use, preferably in treating or preventing a disease in which angiogenesis contributes to disease development or progression. The term "inhibitor" is used broadly to refer to compounds that interfere with the pro-angiogenic activity of Factor 1 or Factor 2. An inhibitor may act on the transcription and/or translation of mRNA encoding Factor 1 or Factor 2 thereby preventing its cellular production and, thus secretion into the circulation and/or at the site of disease development or progression. An inhibitor may also act by specifically binding to Factor 1 or Factor 2 protein or to cellular proteins to which Factor 1 or Factor 2 proteins specifically bind, preferably their cellular receptors. Such binding may prevent or disrupt the natural interaction of Factor 1 or Factor 2 with other cellular proteins, preferably their respective cellular receptors. The skilled person is well aware of how to interfere with the binding between a receptor and its agonist and can use this knowledge to design suitable inhibitors of Factor 1 and Factor 2. Furthermore an inhibitor can be derived from Factor 1 or Factor 2 protein itself by deleting or mutating those parts of Factor 1 and Factor 2 protein, respectively that exert the pro-angiogeneic function of Factor 1 and Factor 2. Such inactive mutated or deleted Factor 1 or Factor 2 will compete with wild-type Factor 1 and Factor 2 for its natural binding partners. A compound that interferes with the pro-angiogenic activity of Factor 1 or Factor 2 reduces the activity by at least 20%, preferably by at least 30%, more preferably by at least 40%. In the context of inhibitors that specifically bind to Factor 1 or Factor 2 or that comprise, essentially consist or consist of mutants or fragments of Factor 1 and Factor 2, respectively, it is preferred that they exert this level of inhibition of Factor 1 protein or Factor 2 protein at an equimolar concentration. A preferred assay, which can be used to determine inhibition of pro-angiogenic activity is described in Example 10 herein. To determine whether a given inhibitor has this activity at an equimolar amount the molar amounts of Factor 1 and 2, respectively and of the respective inhibitor has to be determined. Factor 1 according to SEQ ID NO: 1 has a MW of 15.84 kD and Factor 2 according to SEQ ID NO: 3 has a MW of 21.57 kD and an IgG has a molecular weight of approx. 150 kD. Thus, 100 ng Factor 1 and 947 ng Factor 1 specific IgG are approx., equimolar and 100 ng Factor 2 and 695 ng Factor 2-specific IgG are approx. equimolar. It is apparent from FIG. 12 Panel A and B, respectively, that the Factor 1 and Factor 2 specific antibodies provided herein are inhibitors of Factor 1 protein or Factor 2 protein in that sense. If the context of inhibitors that interfere with transcription and/or translation of mRNA encoding Factor 1 or Factor 2 the level of inhibition is preferably measured on the basis of the protein produced in a cell naturally producing Factor 1 or Factor 3. The skilled person is well aware of a large number of methods to measure the amounts of mRNA encoding Factor 1 or Factor 3 as well as of Factor 1 or Factor 2 proteins, which can be used when assessing the ability of a compound to interfere with transcription and/or translation of Factor 1 or Factor 2 encoding mRNA. Preferably, the Factor 1 protein comprises, essentially consists or consists of the amino acid sequence according to SEQ ID NO: 1 and Factor 2 comprises, essentially consists or consists of the amino acid sequence according to SEQ ID NO: 3 or a variant thereof, which has at least 80% sequence identity to SEQ ID NO: 1 or 3.

It preferred that the inhibitor used in the context of the present invention is a protein comprising, essentially consisting or consisting of an inhibitory fragment or inhibitory mutant of the amino acid sequence according to SEQ ID NO: 1 or 3 or of a variant thereof, which has at least 80% sequence identity to the amino acid sequence according to SEQ ID NO: 1 or 3. It is well known in the art that proteins that exert their function by protein-protein interaction via a receptor comprise domains that are necessary for binding to the receptor, and domains that elicit the receptor to transmit a signal into the cell. Thus, the skilled person is well aware how to generate inhibitory fragments or mutants of such receptor binding proteins. For example, a series of N- and/or C-terminally truncated Factor 1 or Factor 2 proteins can be generated and tested for their pro-angiogenic activity in an assay as outlined in Example 2. Those fragments which no longer show pro-angiogenic activity are then tested in an assay as outlined in Example 10 for their ability to inhibit the pro-angiogenic activity of Factor 1 or 2 protein. Mutants of Factor 1 and 2 can be generated as known in the art, e.g. by alanine scanning mutagenesis. In alanine scanning a series of mutants is generated in which each mutant comprises 1, 2, 3 or more amino acids, which have been mutated to alanine (so-called cassettes) and wherein the mutants differ in the positions of the cassettes within Factor 1 or 2. Factor 1 or 2 mutants that have lost their pro-angiogenic activity can again be identified as outlined in Example 2. Inhibitory mutants can subsequently be identified by using an assay as outlined in Example 10.

In another preferred embodiment the inhibitor is a ligand, specifically binding to the amino acid sequence according to SEQ ID NO: 1 or 3 or a variant thereof, which has at least 80% sequence identity to the amino acid sequence according to SEQ ID NO: 1 or 3 or to the receptor that naturally interact with Factor 1 or 3 or a variant thereof, which has at least 80% sequence identity to the amino acid sequence according to SEQ ID NO: 1 or 3. The term "ligand" is used in the present invention to refer to a chemical moiety that specifically binds to the specified antigen. Preferred ligands are amino acid based ligands, like immunoglobulins, preferably antibodies or antigen-binding fragments thereof and antibody-like proteins. Alternatively, ligands may be peptidomimetics.

The term "immunoglobulin (Ig)" is used herein to refer to immunity conferring glycoproteins of the immunoglobulin superfamily. "Surface immunoglobulins" are attached to the membrane of effector cells by their transmembrane region and encompass molecules such as but not limited to B-cell receptors, T-cell receptors, class I and II major histocompatibility complex (MHC) proteins, beta-2 microglobulin (β2M), CD3, CD4 and CD8. Typically, the term "antibody" as used herein refers to secreted immunoglobulins which lack the transmembrane region and can thus, be released into the bloodstream and body cavities. Antibodies are grouped into different isotypes based on the heavy chain they possess. There are five types of human Ig heavy chains denoted by the Greek letters: α, δ, ε, γ, and μ. The type of heavy chain present defines the class of antibody, i.e. these chains are found in IgA, IgD, IgE, IgG, and IgM antibodies, respectively, each performing different roles, and directing the appropriate immune response against different types of antigens. Distinct heavy chains differ in size and composition; α and γ comprise approximately 450 amino acids, while μ and ε have approximately 550 amino acids (Janeway et al. (2001) Immunobiology, Garland Science). Antibodies comprise four polypeptide chains, namely two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. CDRs for heavy and light chains can be determined as known in the art. For example, the following set of rules may be used to find the CDRs within an antibody light and heavy chain sequence, respectively:

Light chain CDR-1: Start: Approx. residue 24, Residue before the CDR-1 always a Cys, Residue after the CDR1 always a Trp. Typically Trp-Tyr-Gln, but also, Trp-Leu-Gln, Trp-Phe-Gln, Trp-Tyr-Leu; Length: 10 to 17 residues Light chain CDR-2: Start: always 16 residues after the end of L1, residues before generally Ile-Tyr, but also, Val-Tyr, Ile-Lys, Ile-Phe, Length always 7 residues;

Light chain CDR-3: Start:always 33 residues after end of CDR-2; residue before always Cys, Residues after always Phe-Gly-XXX-Gly, Length: 7 to 11 residues Heavy chain CDR-1: Start: Approx. residue 26 always 4 after a Cys (based on the Chothia AbM definition, Kabat definition starts 5 residues later); residues before always Cys-XXX-XXX-XXX; residues after always a Trp. Typically Trp-Val, but also, Trp-Ile, Trp-Ala, Length: 10 to 12 residues [AbM definition, Chothia definition excludes the last 4 residues);

Heavy chain CDR-2: Start: always 15 residues after the end of Kabat/AbM definition, of heavy chain CDR-1; residues before: typically Leu-Glu-Trp-Ile-Gly, but a number of variations, residues after Lys/Arg-Leu/Ile/Val/Phe/Thr/Ala-Thr/Ser/Ile/Ala, Length Kabat definition 16 to 19 residues (definition according to AbM; Chothia definition ends 7 residues earlier)

Heavy chain CDR-3: Start: always 33 residues after end of heavy chain CDR-2 (always 2 amino acid residues after a Cys); Residues before always Cys-XXX-XXX (typically Cys-Ala-Arg); Residues after always Trp-Gly-XXX-Gly;

Length: 3 to 25 residues. This set of rules is known to the skilled person and can also be found on http://www.bioinf.orguk/abs/#cdrid.

The term "human antibody", as used herein, is intended to include antibodies having variable and constant regions derived from human germline immunoglobulin sequences. The human mAbs may include amino acid residues not encoded by human germline immunoglobulin sequences (e.g., mutations introduced by random or site-specific mutagenesis in vitro or by somatic mutation in vivo), for example in the CDRs. However, the term "human antibody", as used herein, is not intended to include "humanized antibodies" in which the CDR sequences derived from the germline of another mammalian species (e.g., mouse), have been grafted onto human FR sequences. Human antibodies also include antibodies isolated from human immunoglobulin libraries or from animals transgenic for one or more human immunoglobulin and that do not express endogenous immunoglobulins.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell. The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences. As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism. As used herein, a "heterohybrid antibody" refers to an antibody having light and heavy chains originating of different organism. For example, an antibody having a human heavy chain associated with a murine light chain is a heterohybrid antibody.

The term "antigen-binding fragments" refers to fragments of an antibody which retain the function of specifically binding an antigen or antigenic protein but which lack some or all other structural features of an antibody or artificial constructs that comprise parts of antibodies. Preferred examples of antigen-binding fragments include but are not limited to the following Fab fragments, Fc fragment, Fab' fragment, F(ab')2, single domain antibodies (sdAb), Nanobodies, single chain Fv, Divalent single-chain variable fragments (di-scFvs), tandem scFvs, diabodies, single-chain diabodies (scDB), triabodies, Bi-specific T-cell engagers (BiTEs), or dual affinity retargeting molecules (DART molecules).

"Fab fragments" (also referred to as "Fab portion" or "Fab region") each with a single antigen binding site, and a residual "Fc fragment" (also referred to as "Fc portion" or "Fc region") whose name reflects its ability to crystallize readily. "Fab' fragment", which refers to a Fab fragment additionally comprising the hinge region of an Ig molecule whilst "F(ab')$_2$ fragments" are understood to comprise two Fab' fragments being either chemically linked or connected via a disulfide bond. Whilst sdAb (Desmyter et al. 1996) and "Nanobodies" only comprise a single $V_H$ domain, "single chain Fv (scFv)" fragments comprise the heavy chain variable domain joined via a short linker peptide to the light chain variable domain (Huston et al. 1988). di-scFvs can be engineered by linking two scFvs (scFvA-scFvB). This can be done by producing a single peptide chain with two $V_H$ and two $V_L$ regions, yielding "tandem scFvs" ($V_H$A-$V_L$A-$V_H$B-$V_L$B). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a $V_H$ and $V_L$ domain lead to the formation of monospecific trimers, so-called "triabodies" or "tribodies". Bispecific diabodies are formed by expressing to chains with the arrangement $V_H$A-$V_L$B and $V_H$B-$V_L$A or $V_L$A-$V_H$B and $V_L$B-$V_H$A, respectively. Single-chain diabodies (scDb) comprise a $V_H$A-$V_L$B and a $V_H$B-$V_L$A fragment which are linked by a linker peptide (P) of 12-20 amino acids, preferably 14 amino acids, ($V_H$A-$V_L$B-P-$V_H$B-$V_L$A). "Bi-specific T-cell engagers (BiTEs)" are fusion proteins consisting of two scFvs of different antibodies wherein one of the scFvs binds to T cells via the CD3 receptor, and the other to a tumor cell via a tumor specific molecule (Kufer et al. 2004)). Dual affinity retargeting molecules ("DART" molecules) are diabodies additionally stabilized through a C-terminal disulfide bridge.

The term "antibody-like protein" refers to a protein having similar properties as an antibody in that it binds to an antigen or antigenic protein without necessarily having the structural features of an antibody. Antibody-like proteins may occur naturally or may be designed artificially, e.g. biotechnologically. Examples of naturally occurring antibody-like proteins include but are not limited to antigen-binding proteins such as e.g. the family of lipocalins, which represent a family of diverse proteins which normally serve for the storage or transport of physiologically important compounds. They share a conserved barrel of eight antiparallel β-strands as their central folding motif and comprise at one end of this barrel structure six hypervariable loops which are connect to each pair of β-strands. These loops form the entrance to the binding pocket. The structural diversity among the members of the lipocalin family reflects the differing shapes and chemical properties of their binding partner. Thus, although being composed of a single polypeptide chain and being much smaller than immunoglobulins, they exhibit a vast potential to bind antigens of differing specificities. Examples of artificially designed antibody-like protein include scaffold-based proteins which are generated by fusing peptides with known affinity towards a certain target or by inserting said peptides into, a scaffold protein to combine the binding properties of the peptide with the desired favorable characteristics of the scaffold carrier. The skilled person is aware of a large number of such scaffold-based proteins. The term "scaffold protein" as used herein refers to a protein which possesses structural rigidity, i.e. folds into a stable tertiary structure. The amino acids of a scaffold protein are likely to occupy a defined three-dimensional position within the scaffold protein. Thus, if one or more of the amino acids of a scaffold protein are replaced by a polypeptide of a suitable length the polypeptide will occupy similar positions as those replaced. This allows positioning a given polypeptide at a defined three-dimensional location and/or orientation within the scaffold protein. Accordingly, scaffold proteins can be used as an alternative to antibodies for molecular recognition (see, e.g. Skerra A.: (2007) Curr. Opin. Biotechnol. 2007, 18:295-304 or Skerra A. (2000) J. Mol. Recognit. 2000, 13:167-187). An example of such a scaffold protein is the Fyn SH3 domain, which comprises two domains that may be mutated to transfer novel binding specificity to the SH3 domain. Methods to select Fyn SH3 domains that specifically bind to a given antigen are disclosed in, e.g. WO 2000/072742 or WO 2008/022759.

In the context of the present invention the term "peptidomimetics" is used to refer to any molecule whose essential elements (pharmacophore) mimic a natural peptide or protein in 3D space and which retain the ability to interact with the biological target and produce the same biological effect. Peptidomimetics include small protein-like chain designed to mimic a peptide which may typically be obtained either by modifying an existing peptide, or by designing similar systems that mimic peptides, such as e.g. peptoids and β-peptides. Irrespective of the approach, the altered chemical structure is designed to adjust the molecular properties advantageously in that e.g. the stability or biological activity is increased or decreased. According modifications involve changes to the peptide that will not occur naturally including but not limited to altered backbones and the incorporation of non-natural amino acids.

The terms "specific binding" or "specifically binding" to an antigen, e.g. Factor 1 or Factor 2, refers to the ability of a ligand to bind to an antigenic determinant of an antigen with high affinity. In that context "high affinity" means that the $K_d$ for the interaction is below $1 \times 10^{-5}$ M, preferably below $1 \times 10^{-6}$ M, more preferably below $1 \times 10^{-7}$, even more preferably below $1 \times 10^{-8}$ M and most preferably below $1 \times 10^{-9}$ M.

Preferred antibodies for use in the context of the sixth aspect of the present invention are monoclonal antibodies, preferably human or humanized antibodies.

In another preferred embodiment the inhibitor is a nucleic acid inhibiting or preventing transcription and/or translation of a mRNA encoding a protein comprising the amino acid sequence according to SEQ ID NO: 1 or 3 or a variant thereof, which has at least 80% sequence identity to the amino acid sequence according to SEQ ID NO: 1 or 3. The skilled person is well aware how to determine the sequence of such nucleic acids based on the genomic sequence encoding the protein comprising the amino acid sequence according to SEQ ID NO; 1 or 3. An example of such inhibitory nucleic acids are siRNAs specific to Factor 1 or Factor 2 encoding mRNA.

In those cases in which the inhibitor of the sixth aspect of the present invention is a protein that can be encoded by a nucleic acid it is envisioned that the inhibitor is administered by providing a nucleic acid encoding the inhibitor. Accordingly, in a seventh aspect the present invention provides a nucleic acid encoding the inhibitor of the sixth aspect of the present invention, for use in treating or preventing a disease in which angiogenesis contributes to disease development or progression. The nucleic acid may further comprise any of the elements described in the context of the third aspect of the present invention.

Accordingly, in an eight aspect the present invention provides a vector comprising the nucleic acid of the sixth aspect of the present invention for use in treating or preventing a disease in which angiogenesis contributes to disease development or progression. The term "vector" in the context of the seventh aspect has the same meaning as described above in the context of the fourth aspect of the invention.

In a preferred embodiment of this aspect of the invention, the vector is a viral vector. Suitable viral vectors include but are not limited to adenoviral vectors, adeno-associated viral (AAV) vectors, alphaviral vectors, herpes viral vectors, measles viral vectors, pox viral vectors, vesicular stomatitis viral vectors, retroviral vector and lentiviral vectors. metastasization Furthermore in an ninth aspect the present invention provides a pharmaceutical composition comprising the inhibitor of the sixth aspect, the nucleic acid of the seventh aspect or the vector of the eight aspect and optionally a suitable pharmaceutical excipient, for use in treating or preventing a disease in which angiogenesis contributes to disease development or progression. This pharmaceutical composition may also comprise any of the ingredients taught above-regarding the fifth aspect of the invention.

The term "a disease in which angiogenesis contributes to disease development or progression" as used in the sixth to ninth aspect of the invention refers to diseases in which proliferation of cells that form blood vessels occurs at the onset, during development and/or during progression of the disease. The cells that form blood vessels and which may proliferate include endothelial cells lining the interior of the blood vessel and smooth muscle cells forming the blood vessel wall. Neither endothelial cells nor smooth muscle cells proliferate in a healthy vessel. These cells proliferate, e.g. in response to injury or chemical cues like, e.g. VEGF. Angiogenesis is also referred to as neovascularization and characterizes the process of forming new blood vessels from pre-existing vessels. In some disease like ocular angiogenesis diseases the aberrant formation of blood vessels is the cause of the disease and in some diseases like benign or malignant tumors angiogenesis occurs during disease progression and supports the growing tumor mass with oxygen and nutrients. In those disease angiogenesis is not the cause of the disease but facilitates disease progression. Neovascularization of malignant tumors also contributes to disease progression by providing tumor cells with an escape route from the tumor mass thereby aiding metastasization.

Preferably the disease in which angiogenesis contributes to disease development or progression is a proliferative disease. Preferred proliferative diseases are selected from the group consisting of benign tumors, malignant tumors, rheumatoid arthritis, psoriasis, ocular angiogenesis diseases, Osier-Webber Syndrome, plaque neovascularization, graft and post-angioplasty stenosis, telaniectasia, hemophiliac joints, angiofibroma, wound granulation, intestinal adhesions, atheriosclerosis, scleroderma, hypertrophic scars, cat scratch disease, and ulcers, in particular macular degeneration, adrenocortical cancer, bladder cancer, bone cancer, brain cancer, breast cancer, cervical cancer, colon cancer, colorectal cancer, endometrial cancer, esophogeal cancer, eye cancer, gallbladder cancer, gastric cancer, head and neck cancer, laryngeal cancer, liver cancer, lung cancer, melanoma, myeloproliferative disorders, neck cancer, nonmelanoma skin cancer, ovarian cancer, prostate cancer, benign prostatic hyperplasia, pancreatic cancer, rectal cancer, and testicular cancer. Preferred diseases to be treated are benign tumors, malignant tumors, and ocular angiogenesis diseases.

The present inventors have identified that antibodies directed against certain epitops of Factor 1 and Factor 2 interfere with the pro-angiogenic function of Factor 1 and Factor 2, respectively, i.e. are antagonistic antibodies. Accordingly, the present invention in a tenth aspect is directed at ligands of Factor 1 and Factor 2, respectively, that inhibit the pro-angiogenic activity of Factor 1 and Factor 2, respectively. Particularly preferred are antibodies or fragments thereof, that inhibit the pro-angiogenic activity of Factor 1 and Factor 2, respectively. The present inventors have successfully provided examples of such inhibitory antibodies by raising the antibodies that specifically bind to surface exposed domains of Factor 1 and 2. In a preferred embodiment of this aspect of the invention it relates to ligands that are capable of specific binding to these fragments of Factor 1 and 2, respectively. In the context of this aspect of the invention the definitions provided in the general definition section and the specific definition in the context of the sixth aspect of the invention equally applies.

Accordingly, in a preferred embodiment the present invention relates to a ligand, preferably an antibody or fragment thereof, or an antibody-like protein specifically binding to an epitope of human Factor 1 protein comprised in or consisting of amino acids 61 to 76 of SEQ ID NO: 1 or a region from another Factor 1 protein corresponding to this epitope.

In a further preferred embodiment the present invention relates to a ligand, preferably an antibody or fragment thereof, or an antibody-like protein specifically binding to an epitope of human Factor 2 protein comprised in or consisting of amino acids 181 to 195 of SEQ ID NO: 3 or to a region from another Factor 2 protein corresponding to this epitope.

The term "region from another Factor 1 or 2 protein corresponding to this epitope" in the context of above preferred aspects of the invention refers to an amino acid sequence from another Factor 1 or 2 protein which aligns with the indicated amino acid sequences of Factor 1 or 2 when using standard alignment tools, like e.g. ClustalW, and standard parameters as outlined above. FIGS. 6 to 11 show several of such alignments of Factor 1 and 2 proteins. The skilled person can easily identify the segment of SEQ ID NO: 2 that has the amino acid sequence CTIWRPQGKSY-LYFTQ (SEQ ID NO: 38) and determine the corresponding amino acids of another Factor 1 protein.

EXAMPLES

The Examples are designed in order to further illustrate the present invention and serve a better understanding. They are not to be construed as limiting the scope of the invention in any way.

Example 1

In a multi-centre, placebo-controlled clinical trial the effects of an intracoronary infusion of autologous bone marrow cells in patients with AMI were tested by one of the inventors (BOOST-2, Controlled Trials Identification No. ISRCTN17457407). Within the trial, bone marrow aspirates were obtained from AMI patients for research purposes. CXCR4+ bone marrow cells were isolated by magnetic cell separation (MiniMACS™, Miltenyi Biotec). After two subsequent purification steps, a CXCR4+ enriched cell population was obtained (>95% purity as confirmed by flow cytometry). Next RNA was isolated from these cells and the RNA was used in a microarray analysis (Affymetrix GeneChip HG_U133 Plus 2.0). In a subsequent bioinformatic analysis, the 4000 expressed sequence tags (ESTs) that were most strongly expressed by CXCR4+ bone marrow cells in the microarray were examined. A series of bioinformatic tools was used to identify putative secreted Factors among those ESTs that were characterised by an N-terminal signal peptide, absence of mitochondrial or nuclear signal peptides, absence of an endoplasmic retention sequence and absence of transmembrane domains. In total, 283 putative secreted Factors were identified; 117 of those were found in NCBI Blast to have a mouse homologue. The cDNAs of the human homologues were cloned into expression plasmids which were then individually transfected into human embryonic kidney (HEK) cells. The transfected HEK cells were cultured in serum-free medium to obtain conditioned culture supernatants after 30 hours. The conditioned HEK cell supernatants were individually tested for pro-angiogenic effects in miniaturized angiogenesis assays and cytoprotective effects in cardiomyocyte cell death assays. This screen resulted in the identification of 2 secreted proteins; 'Factor 1' showed pro-angiogenic effects and cytoprotective effects in the above assays; 'Factor 2' showed pro-angiogenic effects in the above assays.

The sequences identified in the screen and the respective mouse or human homologues are:

Factor 1:

The Human Factor 1 was Identified in the Screen and Used in Example 2 and FIG. 1:

*Homo sapiens* chromosome 19 open reading frame 10 (C19orf10)

The nucleic acid sequence encoding human Factor 1 is available under NCBI Reference Sequence: NM_019107.3 (SEQ ID NO: 6). The amino acid of human Factor 1 is depicted in FIG. 6 (SEQ ID NO: 2).

The Mouse Homologue was Used in Examples 3-6 and FIGS. 2-5:

*Mus musculus* DNA segment, Chr 17, Wayne State University 104, expressed (D17Wsu104e)

The nucleic acid sequence encoding mouse Factor 1 is available under NCBI Reference Sequence: NM_080837.2 (SEQ ID NO: 7). The amino acid sequence of mouse Factor 1 is depicted in FIG. 6 (SEQ ID NO: 13).

Factor 2:

The Human Factor 2 in its Secreted Form was Identified in the Screen and Used in Example 2 and FIG. 1:

*Homo sapiens* chromosome 19 open reading frame 63 (C19orf63), transcript variant HSS1.

The nucleic acid sequence encoding human Factor 2 is available under NCBI Reference Sequence: NM_175063.4 (SEQ ID NO: 8). The amino acid sequence of the secreted form of human Factor 2 is depicted in FIG. 8 (SEQ ID NO: 4).

The Human Factor 2 in its Transmembrane Forms:

*Homo sapiens* chromosome 19 open reading frame 63 (C19orf63), transcript variant HSM1.

The nucleic acid sequence encoding the transmembrane form of human Factor 2 is available under NCBI Reference Sequence: NM_206538.2 (SEQ ID NO: 9). The amino acid sequence of the transmembrane form of human Factor 2 is depicted in FIG. 10 (SEQ ID NO: 5).

The amino acid sequence of a variant of the transmembrane form of human Factor 2 is available in GenBank: AY358710.1 (SEQ ID NO: 34).

Figure 3:
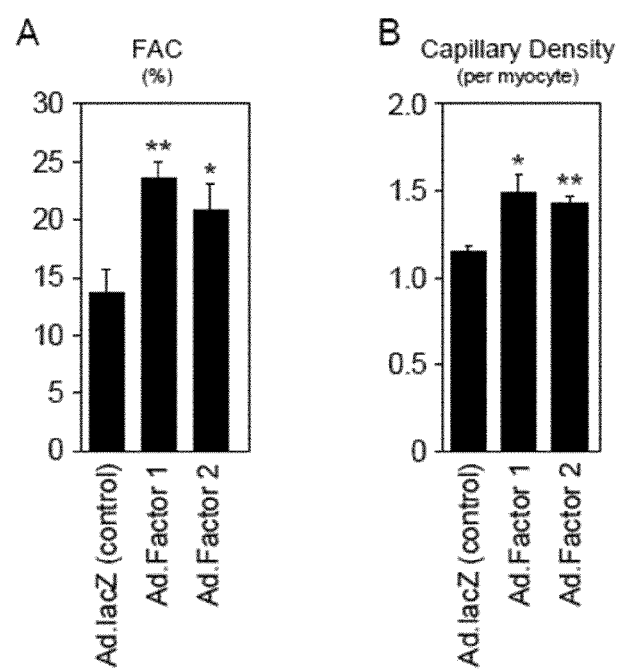
FIG. 3: Mouse Factor 1 or Factor 2 cDNAs (nucleic acids according to SEQ ID NO: 7 and 10) were cloned into replication-deficient adenoviruses. A replication-deficient adenovirus encoding-galactosidase (lacZ) was used as control. 10 to 12-week-old male C57BL/6 mice were anesthetized and ventilated with isoflurane and subjected to permanent left anterior descending coronary artery (LAD) ligation. Viruses were injected into the left ventricular (LV) cavity immediately after LAD ligation. (A) Left ventricular systolic function (fractional area change, FAC) was assessed by transthoracic echocardiography 28 days after LAD ligation. (B) Isolectin-positive capillary density in the infarct border zone was quantified by fluorescent microscopy 28 days after LAD ligation. *P<0.05, **P<0.01 vs. Ad. lacZ control.
Figure 4:
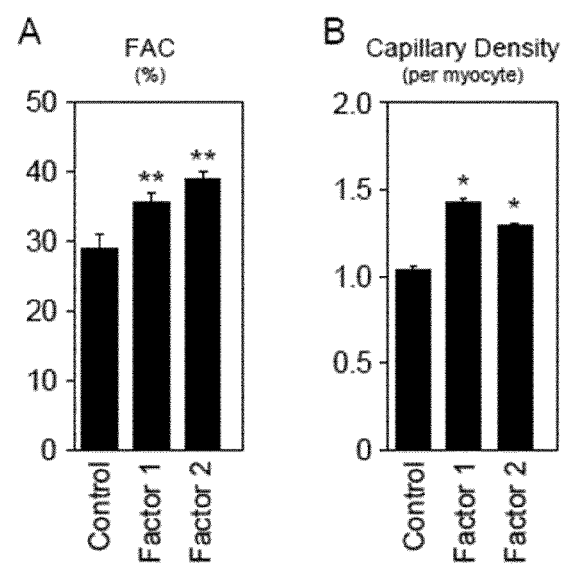
FIG. 4: 10 to 12-week-old male C57BL/6 mice were anesthetized and ventilated with isoflurane and subjected to transient left anterior descending coronary artery ligation for 1 hour followed by reperfusion for 28 days. Mice received a single s.c. injection of recombinant mouse Factor 1 (amino acid sequences according to SEQ ID NO: 13) or Factor 2 (amino acid sequence according to SEQ ID NO: 24) at the time of reperfusion. This was followed by a 7 day continuous s.c. infusion of recombinant Factor 1 or Factor 2. Control mice were infused with PBS. (A) Left ventricular systolic function (fractional area change, FAC) was assessed by transthoracic echocardiography 28 days after reperfusion. (B) Isolectin-positive capillary density in the infarct border zone was quantified by fluorescent microscopy 28 days after reperfusion. *P<0.05, **P<0.01 vs. PBS control.
Figure 5:
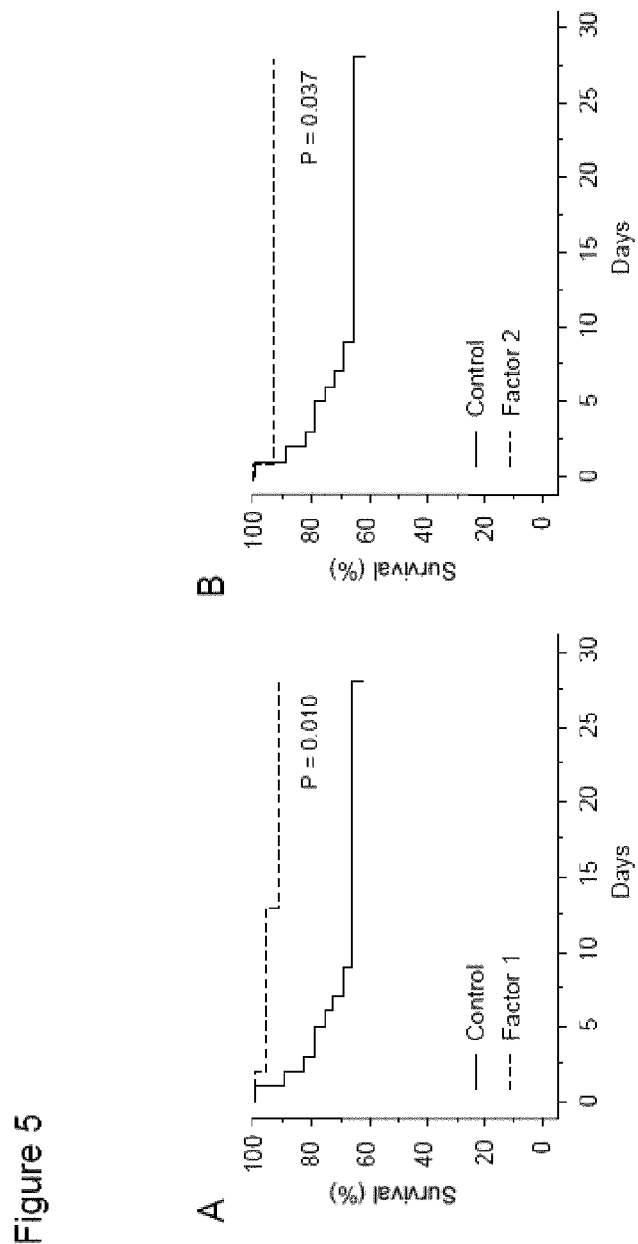
FIG. 5: 10 to 12-week-old male C57BL/6 mice were anesthetized and ventilated with isoflurane (1-2%) and subjected to transient left anterior descending coronary artery ligation for 1 hour followed by reperfusion for 28 days. Mice received a single s.c. injection of recombinant mouse Factor 1 or Factor 2 (SEQ ID NO: 13 and 24, respectively) at the time of reperfusion (PBS was injected in control mice). This was followed by a 7 day continuous s.c. infusion of recombinant Factor 1 or Factor 2. Control mice were infused with PBS. Mice were inspected daily for 28 days to assess post-infarct survival.

The Mouse Homologue of the Secreted Form was Used in Examples 4-6 and FIGS. 3-5:

*Mus musculus* hematopoietic signal peptide-containing secreted 1 (2310044H10Rik) mRNA, complete cds, alternatively spliced. The nucleic acid sequence encoding the transmembrane form of mouse Factor 2 is available under GenBank: AY761096.1 (SEQ ID NO: 10) The amino acid sequence of the secreted form of mouse Factor 2 is depicted in FIG. 8 (SEQ ID NO: 24).

The Mouse Homologue of the Transmembrane Form:

Mus musculus RIKEN cDNA 2310044H10 gene (2310044H10Rik). The nucleic acid sequence encoding the transmembrane form of mouse Factor 2 is available under NCBI Reference Sequence: NM_197991.2 (SEQ ID NO: 11). The amino acid sequence of the transmembrane form of mouse Factor 2 is depicted in FIG. 10 (SEQ ID NO: 29).

Example 2

To confirm the pro-angiogenic activities observed in the screen, both Factors (human homologues encoded by the nucleic acid sequences shown in SEQ ID NOs: 6 and 8) were produced in COS7 cells as His-tagged recombinant proteins. As shown in FIG. 1, recombinant Factor 1 and recombinant Factor 2 promoted dose-dependent pro-angiogenic effects in cultured human endothelial cells.

Human coronary artery endothelial cells (HCAEC) and human umbilical vein endothelial cells (HUVEC) were purchased from Provitro (Berlin, Germany). Cells were cultured for 24 hours in minimal medium in the absence (control) or presence of 10% fetal calf serum (FCS), human recombinant VEGF-A (R&D Systems), or different concentrations of recombinant human Factor 1 (SEQ ID NO: 2) or Factor 2 (SEQ ID NO: 4), as indicated. (A) HCAEC proliferation was measured by bromodeoxyuridine incorporation. (B) HCAEC migration was assessed after wounding a confluent endothelial cell monolayer with a pipette tip. (C) HUVEC network formation was assessed in cells cultured on growth Factor-reduced Matrigel. N=3-5 independent experiments per condition; *P<0.05, P<0.01, *P<0.001 vs. control (see FIG. 1).

Example 3

Figure 2:
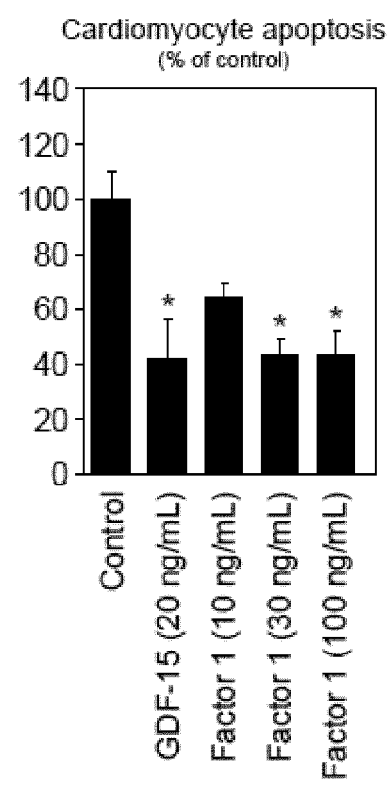
FIG. 2: Ventricular cardiomyocytes were isolated from 1 to 3-day-old Sprague-Dawley rats by Percoll density gradient centrifugation. Cardiomyocytes were exposed to simulated ischemia for 180 min (glucose-free medium containing 2-deoxyglucose in 5% $CO_2$/95% N2 atmosphere) followed by simulated reperfusion for 60 min (back to glucose-containing medium in 5% $CO_2$/95% room air) in the absence (control) or presence of recombinant human GDF-15 or different concentrations of recombinant mouse Factor 1 (amino acid sequence according to SEQ ID NO: 13), as indicated. Cell death was assessed by in situ TdT-mediated dUTP nick end-labeling (TUNEL). N=3 independent experiments per condition; *P<0.05 vs. control.

To confirm the cardiomyocyte-protective effects of Factor 1 observed in the screen, neonatal rat ventricular cardiomyocytes were subjected to simulated ischemia-reperfusion injury in the presence or absence of recombinant Factor 1. Factor 1 (mouse homologue encoded by the nucleic acid sequence shown in SEQ ID NO: 7) was produced in COS7 cells as a His-tagged recombinant protein. As shown in FIG. 2, recombinant Factor 1 promoted dose-dependent anti-apoptotic effects in cultured cardiomyocytes.

Ventricular cardiomyocytes were isolated from 1 to 3-day-old Sprague-Dawley rats by Percoll density gradient centrifugation. Cardiomyocytes were exposed to simulated ischemia for 180 min (glucose-free medium containing 2-deoxyglucose in 5% $CO_2$/95% N2 atmosphere) followed by simulated reperfusion for 60 min (back to glucose-containing medium in 5% CO2/95% room air) in the absence (control) or presence of recombinant human GDF-15 (R&D Systems, known anti-apoptotic cytokine) or different concentrations of recombinant mouse Factor 1, as indicated. Cell death was assessed by in situ TdT-mediated dUTP nick end-labeling (TUNEL). N=3 independent experiments per condition; *P<0.05 vs. control.

Example 4

To explore the therapeutic potential of Factor 1 and Factor 2 in the setting of AMI, adenoviruses encoding the murine homologues of Factor 1 or Factor 2 (the nucleic acid sequences shown in SEQ ID NOs: 7 and 10) were generated and tested in a mouse model of AMI. Adenoviral expression of both Factors resulted in an improvement in left ventricular systolic function 28 days after the infarct. This was associated with an increase in capillary density in the infarct border zone (FIG. 3).

Mouse Factor 1 or Factor 2 cDNAs were cloned into replication-deficient adenoviruses using the AdEasy XL Vector System (Stratagene). A replication-deficient adenovirus encoding-galactosidase (lacZ) was used as control. Viruses were purified with the Adeno-X Virus Purification Kit (BD Biosciences). 10 to 12-week-old male C57BL/6 mice were anesthetized and ventilated with isoflurane (1-2%) and subjected to permanent left anterior descending coronary artery (LAD) ligation. Viruses ($5 \times 10^9$ p.f.u.) were injected into the left ventricular (LV) cavity immediately after LAD ligation. (A) Left ventricular systolic function (fractional area change, FAC) was assessed by transthoracic echocardiography (Visualsonics) 28 days after LAD ligation (N=10-12 mice per group). (B) Isolectin-positive capillary density in the infarct border zone was quantified by fluorescent microscopy 28 days after LAD ligation (N=3 mice per group). *P<0.05, **P<0.01 vs. Ad. lacZ control.

Example 5

To investigate the therapeutic potential of Factor 1 and Factor 2 when applied as recombinant proteins in the setting of reperfused AMI (mimicking the clinical situation in AMI patients receiving reperfusion therapy), 10 to 12-week-old male C57BL/6 mice underwent coronary ligation for 1 hour (ischemia) followed by reperfusion for 28 days. Mice were treated s.c. with both Factors during the first 7 days after reperfusion. Factor 1 and Factor 2 (mouse homologues; amino acid sequences according to SEQ ID NOs: 13 and 24) were produced in HEK293 cells as His-tagged recombinant proteins. Treatment with recombinant Factor 1 or recombinant Factor 2 resulted in a significant improvement in left ventricular systolic function 28 days after the infarct. This was associated with a significant increase in capillary density in the infarct border zone (FIG. 4).

10 to 12-week-old male C57BL/6 mice were anesthetized and ventilated with isoflurane (1-2%) and subjected to transient left anterior descending coronary artery ligation for 1 hour followed by reperfusion for 28 days. Mice received a single s.c. injection of recombinant Factor 1 or Factor 2 (10 µg each) at the time of reperfusion (PBS was injected in control mice). This was followed by a 7 day continuous s.c. infusion of recombinant Factor 1 or Factor 2 using Alzet minipumps (10 µg/day). Control mice were infused with PBS. (A) Left ventricular systolic function (fractional area change, FAC) was assessed by transthoracic echocardiography 28 days after reperfusion (N=10-13 mice per group). (B) Isolectin-positive capillary density in the infarct border zone was quantified by fluorescent microscopy 28 days after reperfusion (N=6 mice per group). *P<0.05, **P<0.01 vs. PBS control.

Example 6

To investigate if Factor 1 and Factor 2, when applied as recombinant proteins, can enhance survival after reperfused AMI, mice underwent coronary ligation for 1 hour followed by reperfusion for 28 days. Mice were treated s.c. with both Factors during the first 7 days after reperfusion. Factor 1 and Factor 2 (mouse homologues; SEQ ID NOs: 7 and 10) were produced in HEK293 cells as His-tagged recombinant proteins. Treatment with recombinant Factor 1 or recombinant Factor 2 resulted in a significant improvement in survival during the first 28 days after the infarct (FIG. 5).

10 to 12-week-old male C57BL/6 mice were anesthetized and ventilated with isoflurane (1-2%) and subjected to transient left anterior descending coronary artery ligation for 1 hour followed by reperfusion for 28 days. Mice received a single s.c. injection of recombinant Factor 1 or Factor 2 (10 µg each) at the time of reperfusion (PBS was injected in control mice). This was followed by a 7 day continuous s.c. infusion of recombinant Factor 1 or Factor 2 using Alzet minipumps (10 µg/day). Control mice were infused with PBS. Mice were inspected daily for 28 days to assess post-infarct survival. N=29 PBS-treated mice; N=25 Factor 1-treated mice; N=15 Factor 2-treated mice.

Example 7

Homologues sequences to the protein encoded by human C19Orf10 were identified with the BLASTP algorithm on http://blast.ncbi.nlm.nih.gov/Blast.cgi?PROGRAM=blastp&BLAST_PROGRAMS=blastp&PAGE_TYPE=BlastSearch&SHOW_DEFAULTS=on&LINK_LOC=blasthome. SEQ ID NO: 2 served as matrix.

The parameters used are the default parameters: 11 Extension: 1, compositional adjustments=conditional compositional score matrix adjustment together with the database of non-redundant protein sequences (nr).

From the identified sequences, examples from different vertebrate mainly mammalian but also one sequence from amphibian, bird and fish were chosen. The respective sequences are listed in Table 1.

The selected amino acid sequence were aligned using the CLUSTALW2 algorithm on http://www.ebi.ac.uk/Tools/clustalw2/index.html. The respective parameters used are the default parameters: Alignment type=Slow, protein weight matrix=Gonnet, gap open=10, gap extension=0, 20, gap distances=5, No end gaps=no, Output options: format=Aln w/numbers, Order=aligned. The obtained multiple alignments are shown in FIG. 6 for all sequences and in FIG. 7 for the mammalian sequences.

TABLE 1

Homologous amino acid sequences of human Factor 1 identified with the BLASTP algorithm. The *Homo sapiens* sequence served as matrix.

| Accession | Origin | Total Score | Query coverage | Max ident | SEQ ID NO |
|---|---|---|---|---|---|
| NP_061980.1 | Homo sapiens | 359 | 100% | 100% | 2 |
| EHH29500.1 | Macaca mulatta | 357 | 100% | 99% | 12 |
| NP_543027.1 | Mus musculus | 280 | 100% | 84% | 13 |
| NP_001001164.1 | Bos taurus | 305 | 100% | 89% | 14 |
| XP_003421710.1 | Loxodonta africana | 296 | 100% | 87% | 15 |
| EHB15128.1 | Heterocephalus glaber | 294 | 100% | 87% | 16 |
| AES10565.1 | Mustela putorius furo | 289 | 100% | 91% | 17 |
| NP_001006342.1 | Gallus gallus | 209 | 100% | 60% | 18 |
| XP_003440079.1 | Oreochromis niloticus | 185 | 100% | 53% | 19 |
| NP_001093679.1 | Xenopus (Silurana) tropicalis | 182 | 91% | 55% | 20 |

Example 8

Homologues sequences to the protein encoded by human C19Orf63 splice variant HSS1 were searched with the BLASTP algorithm on http://blast.ncbi.nlm.nih.gov/Blast.cgi?PROGRAM=blastp&BLAST_PROGRAMS=blastp&PAGE_TYPE=BlastSearch&SHOW_DEFAULTS=on&LINK_LOC=blasthome. SEQ ID NO: 4 served as matrix.

The parameters used are the default parameters: 11 Extension: 1, compositional adjustments=conditional compositional score matrix adjustment together with the database of non-redundant protein sequences (nr).

From the identified sequences, examples from different vertebrate species mainly mammalian but also one sequence from amphibian and fish were chosen. The respective sequences are listed in table 2.

The selected amino acid sequence were aligned using the CLUSTALW2 algorithm on http://www.ebi.ac.uk/Tools/clustalw2/index.html. The respective parameters used are the default parameters: Alignment type=Slow, protein weight matrix=Gonnet, gap open=10, gap extension=0, 20, gap distances=5, No end gaps=no, Output options: format=Aln w/numbers, Order=aligned. The obtained multiple alignments are shown in FIG. 8 for all sequences and in FIG. 9 for the mammalian sequences.

TABLE 2

Homologous amino acid sequences of the secreted form of human Factor 2 identified with the BLASTP algorithm. The *Homo sapiens* sequence served as matrix.

| Accession | Origin | Total Score | Query coverage | Max ident | SEQ ID NO: |
|---|---|---|---|---|---|
| NP_778233.4 | Homo sapiens | 511 | 100% | 100% | 4 |
| AFE66256.1 | Macaca mulatta | 503 | 100% | 98% | 21 |
| XP_003465531.1 | Cavia porcellus | 434 | 100% | 91% | 22 |
| XP_863321.1 | Canis lupus familiaris | 427 | 100% | 91% | 23 |
| AAV30544.1 | Mus musculus | 401 | 93% | 86% | 24 |
| XP_001494158.1 | Equus caballus | 429 | 100% | 95% | 25 |
| AAI41719.1 | Xenopus laevis | 275 | 89% | 61% | 26 |
| NP_001157390.1 | Danio rerio | 233 | 80% | 55% | 27 |

Example 9

Homologues sequences to the protein encoded by human C19Orf63 splice variant HSM1 were searched with the BLASTP algorithm on http://blast.ncbi.nlm.nih.gov/Blast.cgi?PROGRAM=blastp&BLAST_PROGRAMS=blastp&PAGE_TYPE=BlastSearch&SHOW_DEFAULTS=on&LINK_LOC=blasthome. SEQ ID NO: 5 served as matrix.

The parameters used are the default parameters: 11 Extension: 1, compositional adjustments=conditional compositional score matrix adjustment together with the database of non-redundant protein sequences (nr).

From the identified sequences, examples from different vertebrate species mainly mammalian but also one sequence from amphibian and fish were chosen. The respective sequences are listed in table 3.

The selected amino acid sequence were aligned using the CLUSTALW2 algorithm on http://www.ebi.ac.uk/Tools/clustalw2/index.html. The respective parameters used are the default parameters: Alignment type=Slow, protein weight matrix=Gonnet, gap open=10, gap extension=0, 20, gap distances=5, No end gaps=no, Output options: format=Aln w/numbers, Order=aligned. The obtained multiple alignments are shown in FIG. 10 for all sequences and in FIG. 11 for the mammalian sequences.

TABLE 3

Homologous amino acid sequences of the transmembrane form of human Factor 2 identified with the BLASTP algorithm. The *Homo sapiens* sequence served as matrix.

| Accession | Origin | Total Score | Query coverage | Max ident | SEQ ID NO: |
|---|---|---|---|---|---|
| NP_996261.1 | *Homo sapiens* | 527 | 100% | 100% | 5 |
| XP_001173798.1 | *Pan troglodytes* | 520 | 100% | 99% | 28 |
| AAH20179.1 | *Mus musculus* | 421 | 93% | 87% | 29 |
| EHB05689.1 | *Heterocephalus glaber* | 426 | 93% | 92% | 30 |
| XP_003406885.1 | *Loxodonta africana* | 380 | 93% | 92% | 31 |
| NP_988902.1 | *Xenopus (Silurana) tropicalis* | 310 | 89% | 64% | 32 |
| NP_001157390.1 | *Danio rerio* | 223 | 77% | 54% | 33 |

Example 10

Human coronary artery endothelial cells (HCAECs, from Provitro) were grown in T75 flasks in EGM-2 medium (Lonza) supplemented with 10% FCS (Biochrom). Cells from passages 3-6 were used. Prior to stimulation with various agents, cells were cultured overnight in MCDB131 (Life Technologies) containing 2% FCS. HCAECs were then seeded in 96 well plates ($5 \times 10^3$ cells per well), and stimulated with recombinant human Factor 1, recombinant human Factor 2, or VEGF (positive control) in the presence or absence of different concentrations of rabbit anti-Factor 1 antibody, rabbit anti-Factor 2 antibody, or control IgG for 16 h. The antibodies were generated by Eurogentec and were raised against polypeptides contained in human Factor 1 (CTIWRPQGKSYLYFTQ, SEQ ID NO: 38, i.e. amino acids 61 to 76 of SEQ ID NO: 1) or Factor 2 (CEQAQKAKNPQEQKSF; SEQ ID NO: 39, i.e. amino acids 181 to 195 of SEQ ID NO: 3 plus an N-terminal Cys). Cell proliferation was measured with a colorimetric BrdU incorporation immunoassay (Roche). Data are presented in FIG. 12 (panel A Factor 1; panel B Factor 2; data are mean±SEM from 3-6 experiments).

---

The invention claimed is:

1. A method for treating myocardial infarction in a subject, comprising: administering to the subject an effective amount of a protein comprising the amino acid sequence according to SEQ ID NO: 1.

2. The method of claim 1, wherein the protein is administered through the oral, intravenous, intramucosal, intraarterial, intramuscular, subcutaneous, or intracoronary route.

3. The method of claim 2, wherein the protein is administered before, simultaneously, or after a reperfusion therapy.

4. The method of claim 3, wherein the administration is through one or more bolus injection(s) and/or infusion(s).

5. A method of treating myocardial infarction in a subject, comprising: administering to the subject an effective amount of a pharmaceutical composition comprising a protein comprising the amino acid sequence according to SEQ ID NO: 1.

6. The method of claim 5, wherein the pharmaceutical composition is administered through the oral, intravenous, intramucosal, intraarterial, intramuscular, subcutaneous, or intracoronary route.

7. The method of claim 6, wherein the pharmaceutical composition is administered before, simultaneously, or after a reperfusion therapy.

8. The method of claim 7, wherein the administration is through one or more bolus injection(s) and/or infusion(s).

9. A method for treating a disease or disorder excluding myocardial infarction, comprising administering to a subject in need thereof an amount effective to treat the disease of a protein comprising the amino acid sequence according to SEQ ID NO: 1;
wherein the disease or disorder is a heart-related disease selected from the group consisting of inherited cardiomyopathy, cardiomyopathy caused by spontaneous mutations, acquired cardiomyopathy, cardiomyopathy caused by infection of the myocardium, hypertensive heart disease caused by pulmonary arterial hypertension, arterial hypertension, diseases of the heart valves, ischemia reperfusion injury, inflammation, infection, trauma, mechanical overload, angina pectoris, and heart failure.

* * * * *